(12) United States Patent
Mukerji et al.

(10) Patent No.: US 7,208,297 B2
(45) Date of Patent: Apr. 24, 2007

(54) Δ4-DESATURASE GENES AND USES THEREOF

(75) Inventors: Pradip Mukerji, Gahanna, OH (US); Jennifer Thurmond, Columbus, OH (US); Yung-Sheng Huang, Upper Arlington, OH (US); Tapas Das, Worthington, OH (US); Amanda Eun-Yeong Leonard, Gahanna, OH (US); Suzette L. Pereira, Westerville, OH (US)

(73) Assignee: Abbott Laboratories, Abbott Park, IL (US)

( * ) Notice: Subject to any disclaimer, the term of this patent is extended or adjusted under 35 U.S.C. 154(b) by 363 days.

(21) Appl. No.: 10/913,226

(22) Filed: Aug. 6, 2004

(65) Prior Publication Data

US 2005/0005328 A1 Jan. 6, 2005

Related U.S. Application Data

(60) Division of application No. 10/120,637, filed on Apr. 11, 2002, now Pat. No. 7,045,683, which is a continuation-in-part of application No. 09/849,199, filed on May 4, 2001, now abandoned.

(51) Int. Cl.
| | |
|---|---|
| *C12P 7/64* | (2006.01) |
| *C12N 9/02* | (2006.01) |
| *C12N 5/00* | (2006.01) |
| *C07H 21/04* | (2006.01) |

(52) U.S. Cl. .................. 435/134; 435/136; 435/189; 435/410; 435/320.1; 536/23.2; 536/23.1

(58) Field of Classification Search .................. None
See application file for complete search history.

(56) References Cited

U.S. PATENT DOCUMENTS

| | | | |
|---|---|---|---|
| 4,666,701 A | 5/1987 | Horrobin et al. | |
| 4,758,592 A | 7/1988 | Horrobin et al. | |
| 4,826,877 A | 5/1989 | Stewart et al. | |
| 5,116,871 A | 5/1992 | Horrobin et al. | |
| 5,196,198 A | 3/1993 | Shaw et al. | |
| 5,340,742 A | 8/1994 | Barclay | |
| 5,443,974 A | 8/1995 | Hitz et al. | |
| 5,547,699 A | 8/1996 | Iizuka et al. | |
| 5,552,306 A | 9/1996 | Thomas et al. | |
| 6,140,365 A | 10/2000 | Kiy et al. | |
| 6,177,108 B1 | 1/2001 | Barclay | |
| 6,207,441 B1 | 3/2001 | Shin et al. | |
| 2002/0138874 A1 | 9/2002 | Mukerji et al. | |
| 2002/0156254 A1 | 10/2002 | Qiu et al. | |

FOREIGN PATENT DOCUMENTS

| | | |
|---|---|---|
| WO | WO 93/11245 | 6/1993 |
| WO | WO 94/11516 | 5/1994 |
| WO | WO 95/24494 | 9/1995 |
| WO | WO 96/13591 | 5/1996 |
| WO | WO 00/12720 | 3/2000 |
| WO | WO 02/26946 | 4/2002 |

OTHER PUBLICATIONS

Brenner et al., *Adv. Exp. Med. Biol.*, 83, 85-101 (1976).
Cho, H.P., et al., "Experimental Biology 98, San Francisco, CA, Apr. 18-22, Abstracts, Part I, Abstract 3093", *The FASEB Journal*, A532 (1998).
Horrobin et al., *Am. J. Clin. Nutr.*, (Suppl.) 57:732S-737S.
Sprecher, H., *Curr. Opin. Clin. Nutr. Metab. Care*, 2:135-138 (1999).
Xia Qiu, et al., "Identification of a Δ4 Fatty Acid Desaturase from *Thraustochytrium* sp. Involved in the Biosynthesis of Docosahexanoic Acid by Heterologous Expression in *Saccharomyces cerevisia* and *Brassica juncea*," *The Journal of Biological Chemistry*, vol. 276, No. 34, Aug. 24, 2001, pp. 31561-31566.

*Primary Examiner*—Nashaat T. Nashed
(74) *Attorney, Agent, or Firm*—Cheryl L. Becker

(57) ABSTRACT

The subject invention relates to the identification of genes involved in the desaturation of polyunsaturated fatty acids at carbon 4 (i.e., "Δ4-desaturase"). In particular, Δ4-desaturase may be utilized, for example, in the conversion of adrenic acid to ω6-docosapentaenoic acid and in the conversion of ω3-docosapentaenoic acid to docosahexaenoic acid. The polyunsaturated fatty acids produced by use of the enzyme may be added to pharmaceutical compositions, nutritional compositions, animal feeds, as well as other products such as cosmetics.

11 Claims, 36 Drawing Sheets

Amino Acid Comparison of Delta-4 Desaturases

```
              1                                                    50
    prta6   MTVGFDETVT MDTVRNHNMP DDAWCAIHGT VYDITKFSKV HPGGDIIMLA
    prta8   MTVGFDETVT MDTVRNHNMP DDAWCAIHGT VYDITKFSKV HPGGDIIMLA
    prta7   MTVGFDETVT MDTVRNHNMP DDAWCAIHGT VYDITKFSKV HPGGDIIMLA
    prta5   MTVGFDETVT MDTVRNHNMP DDAWCAIHGT VYDITKFSKV HPGGDIIMLA 51                                                   100
    prta6   AGKEATILFE TYHIKGVPDA VLRKYKVGKL PQGKKGETSH MPTGLDSAFY
    prta8   AGKEATILFE TYHIKGVPDA VLRKYKVGKL PQGKKGETSH MPTGLDSASY
    prta7   AGKEATILFE TYHIKGVPDA VLRKYKVGKL PQGKKGETSH MPTGLDSASY
    prta5   AGKEATILFE TYHIKGVPDA VLRKYKVGKL PQGKKGETSH MPTGLDSASY 101                                                  150
    prta6   YSWDSEFYRV LRERVAKKLA EPGLMQRARM ELWAKAIFLL AGFWGSLYAM
    prta8   YSWDSEFYRV LRERVAKKLA EPGLMQRARM ELWAKAIFLL AGFWGSLYAM
    prta7   YSWDSEFYRV LRERVAKKLA EPGLMQRARM ELWAKAIFLL AGFWGSLYAM
    prta5   YSWDSEFYRV LRERVAKKLA EPGLMQRARM ELWAKAIFLL AGFWGSLYAM 151                                                  200
    prta6   CVLDPHGGAM VAAVTLGVFA AFVGTCIQHD GSHGAFSKSR FMNKAAGWTL
    prta8   CVLDPHGGAM VAAVTLGVFA AFVGTCIQHD GSHGAFSKSR FMNKAAGWTL
    prta7   CVLDPHGGAM VAAVTLGVFA AFVGTCIQHD GSHGAFSKSR FMNKAAGWTL
    prta5   CVLDPHGGAM VAAVTLGVFA AFVGTCIQHD GSHGAFSKSR FMNKAAGWTL 201                                                  250
    prta6   DMIGASAMTW EMQHVLGHHP YTNLIEMENG LAKVKGADVD PKKVDQESDP
    prta8   DMIGASAMTW EMQHVLGHHP YTNLIEMENG LAKVKGADVD PKKVDQESDP
    prta7   DMIGASAMTW EMQHVLGHHP YTNLIEMENG LAKVKGADVD PKKVDQESDP
    prta5   DMIGASAMTW EMQHVLGHHP YTNLIEMENG LAKVKGADVD PKKVDQESDP 251                                                  300
    prta6   DVFSTYPMLR LHPWHRQRFY HKFQHLYAPF IFGFMTINKV ISQDVGVVLR
    prta8   DVFSTYPMLR LHPWHRQRFY HKFQHLYAPF IFGSMTINKV ISQDVGVVLR
    prta7   DVFSTYPMLR LHPWHRQRFY HKFQHLYAPL IFGFMTINKV ISQDVGVVLR
    prta5   DVFSTYPMLR LHPWHRQRFY HKFQHLYAPF IFGFMTINKV ISQDVGVVLR
```

FIG. 2A

Amino Acid Comparison of Delta-4 Desaturases

```
      301                                                              350
prta6 KRLFQIDANC RYGSPWYVAR FWIMKLLTTL YMVALPMYMQ GPAQGLKLFF
prta8 KRLFQIDANC RYGSPWYVAR FWIMKLLTTL YMVALPMYMQ GPAQGLKLFF
prta7 KRLFQIDANC RYGSPWNVAR FWIMKLLTTL YMVALPMYMQ GPAQGLKLFF
prta5 KRLFQIDANC RYGSPWYVAR FWIMKLLTTL YTVALPMYMQ GPAQGLKLFF 351                                                              400
prta6 MAHFTCGEVL ATMFIVNHII EGVSYASKDA VKGVMAPPRT VHGVTPMQVT
prta8 MAHFTCGEVL ATMFIVNHII EGVSYASKDA VKGVMAPPRT VHGVTPMQVT
prta7 MAHFTCGEVL ATMFIVNHII EGVSYASKDA VKGVMAPPRT VHGVTPMQVT
prta5 MAHFTCGEVL ATMFIVNHII EGVSYASKDA VKGVMAPPRT VHGVTPMQVT 401                                                              450
prta6 QKALSAAEST KSDADKTTMI PLNDWAAVQC QTSVNWAVGS WFWNHFSGGL
prta8 QKALSAAESA KSDADKTTMI PLNDWAAVQC·QTSVNWAVGS WFWNHFSGGL
prta7 QKALSAAEST KSDADKTTMI PLNDWAAVQC QTSVNWAVGS WFWNHFSGGL
prta5 QKALSAAEST KSDADKTTMI PLNDWAAVQC QTSVNWAVGS WFWNHFSGGL 451                                                              500
prta6 NHQIEHHCFP QNPHTVNVYI SGIVKETCEE YGVPYQAEIS LFSAYFKMLS
prta8 NHQIEHHCFP QNPHTVNVYI SGIVKETCEE YGVPYQAEIS LFSAYFKMLS
prta7 NHQIEHHCFP QNPHTVNVYI SGIVKETCEE YGVPYQAEIS LFSAYFKMLS
prta5 NHQIEHHCFP QNPHTVNVYI SGIVKETCEE YGVPYQAEIS LFSAYFKMLS 500
prta6 HLRTLGNEDL TAWST*
prta8 HLRTLGNEDL TAWST*
prta7 HLRTLGNEDL TAWST*
prta5 HLRTLGNEDL TARST*
```

FIG.2B

Gene Sequence of Delta 4-Desaturase of *Thraustochytrium aureum* (ATCC 34304) from plasmid pRTA5

```
atgacggtcg ggtttgacga aacgtgact atggacacgg tccgcaacca caacatgccg      60
gacgacgcct ggtgcgcgat ccacgcacc gtgtacgaca tcaccaagtt cagcaaggtg     120
cacccggcg gggacatcat catgctggcc gctgcgca aggccaccat cctgttcgag       180
acgtaccaca tcaagggcgt cccgacgcg gtgctgcgca agtacaaggt cggcaagctc     240
cccagggca agaaggcga aacgagccac atgccaccg ggctcgactc ggcctcctac        300
tactcgtggg acagcgagtt ttacagggtg ctccgcgagc gcgtcgccaa gaagctgcc    360
gagccggcc tcatgcagcg cgcgcatg gagctctggg ccaaggcgat cttcctcctg       420
gcaggtttct gggctccct ttacgccatg tgcgtgctag acccgcacgg cggtgccatg   480
gtagccgccg ttacgctcgg cgtgttgct gcctttgtcg gaacttgcat ccagcacgac     540
ggagccacg gcgccttctc caagtcgcga ttcatgaaca agcggcggg ctgaccctc      600
gacatgatcg gcgcgagcgc gatgacctgg gagatgcagc acgttcttgg ccaccacccg   660
tacaccaacc tcatcgagat ggagaacggt ttgccaagg tcaagggcgc cgacgtcgac    720
ccgaagaagg tcgaccagga gagcgacccg gacgtcttca gtacgtaccc gatgctctgc   780
ctgcaccccgt ggcaccgcca gcggttttac cacagttcc agcacctgta cgcccgtttt   840
atctttgggt ttatgacgat taacaaggtg atttcccagg atgtcgggt tgtgctgcgc    900
aagcgcctgt tccaactcga cgccaactgc tacacgctc cggtatggca gcccctgta    960
ttctggatca tgaagctcct ggcttttctc tgcttcccat gcttccat gtacatgcag   1020
gggctgctc aggcttgaa gcttttcttc atggccacct tcacctgcgg agaggtcctc   1080
gccaccatgt ttattgtcaa ccacatcatc gagggcgtca gctacgcttc caaggacgcg   1140
gtcaagggcg tcatgctcc gccgcgcact gtgacggtg tcaccccgat gcaggtgacg   1200
caaaggcgc tcagtgcgc cgagtcgacc aagtcgacg ccgacaagac gaccatgatc    1260
cccctcaacg actgggccgc tgtcagtgc cagacctg tgaactgggc tgtcgggtcg   1320
tggttttgga accactttc gggcggcctc aaccaccaga ttgagcacca ctgcttcccc   1380
caaaaccccc acacggtcaa cgtctacatc tcggcatcg tcaaggagac ctgcgaagaa   1440
tacggcgtgc cgtaccagc tgagatcagc ctcttctctg cctatttcaa gatgctgtcg   1500
cacctccgca cgctcggcaa cgaggacctc acggccaggt ccacgtga               1548
```

FIG.3

Gene Sequence of Delta 4-Desaturase of Thraustochytrium aureum (ATCC 34304) from plasmid pRTA6

```
atgacggtcg gtttgacga aacggtgact atgacacgg tccgcaacca caacatgccg      60
gacgacgcct ggtgcgcgat ccacggcacc gtgtacgaca tcgtacaagtt cagcaaggtg   120
caccccggcg gggacatcat catgctggcc gctggcaagg aggccaccat cctgttcgag   180
acgtaccaca tcaagggcgt tccgacgcg gtgctgcgca agtacaaggt cggcaagctc    240
cccaggca agaagggcga aacgagccac atgccaccg ggctcgactc ggccttctac      300
tactcgtggg acagcgagtt ttacagggtg ctccgcgagc gcgtcgccaa gaagctggcc   360
gagcccggcc tcatgcagcg cgcgcacatg gagctctggg ccaaggcgat cttcctcctg   420
gcagtttct gggctccct ttacgccatg tgcgtgctag accggccacg cggtgccatg     480
gtagccgccg ttacgctcgg cgtgttcgct gcctttgtcg gaacttgcat ccagcacgac   540
ggcagccacg gcgcctttc caagtcgcga ttcatgaaca agcggcggg ctggaccctc    600
gacatgatcg gcgcgagcgc gatgacctgg gagatgcagc acgttcttgg ccaccaccg    660
tacccaaacc tcatcgagat gggagaacggt ttggccaagg tcaaggggcg cgacgtcgac  720
ccgaagaagg tcgaccagga gaacgacccg gacgtcttca gtacgtaccc gatgcttcgc  780
ctgcacccgt ggcaccgcca gcggttttac cacagttcc cacaagttcc agcacctgta   840
atctttgggt ttatgacgat taacaaggtg gcgggtttta atttcccagg atgtcgggt   900
aagcgctgt tccagatcga cgccaactgc cgtatggca ccggactgc gccccgtgta    960
ttctgatca tgaagctcct caccacgctc tacatgtgtg cgcttccat gtacatgcag   1020
gggctgctc agggcttgaa gctttctttc atgcccact tcacctgcgg agaggtcctc   1080
gccaccatgt ttattgtcaa ccacatcatc gccgcacact gagggcgtca gctacgcttc  1140
gtcaagggcg tcatgctcc gccgcgcact gtgcacggtg tcaccccgat gcaggtgacg   1200
caaaagccgc tcagtgcggc cgagtcgacg aagtcggacg cagacctctg gctcacccgat gaccatgatc 1260
cccctcaacg actgggccgc tgtcagtgc cagacccctg tgaactgggc tgtcgggtcg    1320
tggtttgga accactttc gggcgcctc aaccaccaga ttgagcacca ctgcttcccc      1380
caaaccccc acacggtcaa cgtctacatc tcaggcatcg tcaaggagac ctgcgaagaa    1440
tacggcgtgc cgtaccagc tgagatcagc ctcttctctg cctatttcaa gatgctgtcg    1500
cacctccgca cgctccgcaa cgaggacctc acggcctggt ccacgtga                1548
```

FIG.4

Gene Sequence of Delta 4-Desaturase of *Thraustochytrium aureum* (ATCC 34304) from plasmid pRTA7

```
atgacggtcg ggtttgacga aacggtgact atggacacgg tccgcaacca caacatgccg      60
gacgacgcct ggtgcgcgat ccacggcacc gtgtacgaca tcaccaagtt cagcaaggtg     120
caccccggcg gggacatcat catgctggcc gctggcaagg aggccaccat cctgttcgag     180
acctaccaca tcaagggcgt cccgacgcg gtgctgcgca agtacaaggt cggcaagctc     240
cccagggca agaagggcga aacgagccac atgccaccg ggcttgactc ggcctcctac     300
tactcgtggg acagcgagtt ttacagggtg ctccgcgagc gcgtcgccaa gaagctgcc     360
gagcccggcc tcatgcagcg cgcgcagatg gagctctggg ccaaggcgat cttcctcctg     420
gcaggtttct gggctccct ttacgccatg tgcgtgctag accccgcacg cggtgccatg     480
gtagccgccg ttacgctcgg cgtgttcgct gcctttgtcg gaacttgcat ccagcacgac     540
ggcagccacg gcgccttctc caagtcgcga ttcatgaaca aggcggcggg ctggaccctc     600
gacatgatcg gcgcgagcgc gatgacctgg ggagaacggt ttggccaagg acgtcttca    660
tacaccaacc tcatcgagat ggagaacggt ttggccaagg tcaagggcgc cgacgtcgac     720
ccgaagaagg tcgaccagga gagcgacccg gcggttttac gacgtcttca gtacgtaccc     780
ctgcaccgt ggcaccgcca gcggttttac cacaagttcc agcagctctc gatgctttgc     840
atcttttggt ttatgacgat taacaaggtg atttcccagg atgtcgggt cgcccgctt     900
aagcgcctgt tccagatcga cgccaactgc cgtatggca gccctggaa cgtggcccgc     960
ttctggatca tgaagctcct caccacgctc tacatggtgg cgcttcccat gtacatgcag    1020
gggctgctc aggcttgaa gcttttcttc atggccact tcacctgcgg agaggtcctc    1080
gccaccatgt tattgtcaa ccacatcatc gagggcgtca gctacgcttc caaggacgcg    1140
gtcaagggcg tcatgctcc gccgcact gtcacggtg tcaccccgat gcaggtgacg    1200
caaaaggcgc tcagtgcggc cgaccgacg aagtcgacg cgacaagac gaccatgatc    1260
cccctcaacg actgggccgc tgtcagtgc cagacctcg tgaactgggc tgtcggtcg    1320
tggttttga accactttc gggggccta aaccaccaga ttgagcacca ctgcttcccc    1380
caaaccccc acacggtcaa cgtctacatc tcgggcatcg tcaaggagac ctgcgaagaa    1440
tacggcgtgc cgtaccagc tgagatcagc ctcttctg cctatttcaa gatgctgtcg    1500
cacctccgca cgctccggca acggaggacctc cgagcctggt ccacgtga              1548
```

FIG.5

Gene Sequence of Delta 4-Desaturase of *Thraustochytrium aureum* (ATCC 34304) from plasmid pRTA8

```
atgacggtcg ggtttgacga aacggtgact atggacacgg tccgcaacca caacatgccg    60
gacgacgcct ggtgcgcgat ccacggcacc gtgtacgaca tcaccaagtt cagcaaggtg   120
caccccggcg gggacatcat catgctggcc gctggcaagg aggccaccat cctgttcgag   180
acctaccaca tcaagggcgt cccgacgcg gtgctgcgca agtacaaggt cggcaagctc   240
cccagggca agaagggcga aacgagccac atgcccaccg ggctcgactc ggcctcctac   300
tactcgtggg acagcgagtt ttacagggtg ctccgcgagc ggtcgccaa gaagctggcc   360
gagcccggcc tcatgcagcg cgcgcagatg gagctctggg ccaaggcgat cttcctcctg   420
gcaggttttct gggctccct ttacgctcct tgcgtgctag acccgcacgg cggtgccatg   480
gtagccgccg ttacgctcgg cgtgttcgct gccttgtcg gaacttgcat ccagcacgac   540
ggcagccacg gcgccttctc caagtcgcga ttcatgaaca agcggcggg ctggaccctc   600
gacatgatcg gcgagtgc gatgacctgg gagatgcagc acgttctgg ccaccaccg    660
tacaccaacc tcatcgagat ggagaacggt ttggccaagg tcaagggcgc cgacgtgac   720
ccgaagaagg tcgaccagga gagcgaccgg gacgtcttca gtacgtacc gatgcttcgc   780
ctgcaccccgt gcaccgcca gcggtttac taacaaggtg atttcccagg atgtcggggt tgtgctgcgc    840
atctttgggt ctatgacgat cgccaactgc cgtatgca gccccctggta cgtggccgc    900
aagcctgt tccagatcga cgccaactgc caccacgctc tacctggtgg gcccctggta gccgcctc    960
ttctggatca tgaagctcct agcttttctc ccacatcatc gagggcgtca gctacgcttc caaggagcg  1020
gggctgctc agggcttgaa gcttttctc ccacatcatc gagggcgtca gctacgcttc caaggacgcg  1080
gccaccatgt ttattgtcaa gctcgcgcc atggccacact gtgcacgtg tcacccgat gcaggtgacg  1140
gtcaaggcg tcatggctc gcagtgcgc cagtcggcc aagtcggacg cagacctg gaactggg tgtcgggtcg  1200
caaaggcgc tcagtgcgc cgagtgcgc aagtcggacg cagacctg gaactggg tgtcgggtcg  1260
ccctcaacg actggggccgc tgtcagtgc gggggccttc cagacccgat gaactgggc tgtgggcgtcg  1320
tggttttga accacttttc gggggccttc aaccaccaga ttgagcacca ctgcttcccc  1380
caaaccccc acacgtcaa cgtctacatc tcgggcatcg ctcttctg tcaaggagag ctgcgaagaa  1440
tacggcgtgc cgtacaagc cgctcggcaa tgagatcagc tgagatcagc cctattcaa gatgctgtcg  1500
cacctccgca cgctcggcaa cgaggacctc cgaggcgtga ccacgtga                         1548
```

FIG. 6

Gene Sequence of Delta 4-Desaturase of *Thraustochytrium aureum* (ATCC 34304) from plasmid pRTA5

Met Thr Val Gly Phe Asp Glu Thr Val Thr Met Asp Thr Val Arg Asn
1             5                   10                  15
His Asn Met Pro Asp Asp Ala Trp Cys Ala Ile His Gly Thr Val Tyr
           20                  25                  30
Asp Ile Thr Lys Phe Ser Lys Val His Pro Gly Gly Asp Ile Ile Met
         35                  40                  45
Leu Ala Ala Gly Lys Glu Ala Thr Ile Leu Phe Glu Thr Tyr His Ile
     50                  55                  60
Lys Gly Val Pro Asp Ala Val Leu Arg Lys Tyr Lys Val Gly Lys Leu
65                  70                  75                  80
Pro Gln Gly Lys Lys Gly Glu Thr Ser His Met Pro Thr Gly Leu Asp
                 85                  90                  95
Ser Ala Ser Tyr Tyr Ser Trp Asp Ser Glu Phe Tyr Arg Val Leu Arg
             100                 105                 110
Glu Arg Val Ala Lys Lys Leu Ala Glu Pro Gly Leu Met Gln Arg Ala
             115                 120                 125
Arg Met Glu Leu Trp Ala Lys Ala Ile Phe Leu Leu Ala Gly Phe Trp
    130                 135                 140
Gly Ser Leu Tyr Ala Met Cys Val Leu Asp Pro His Gly Gly Ala Met
145                 150                 155                 160
Val Ala Ala Val Thr Leu Gly Val Phe Ala Ala Phe Val Gly Thr Cys
                165                 170                 175
Ile Gln His Asp Gly Ser His Gly Ala Phe Ser Lys Ser Arg Phe Met
            180                 185                 190
Asn Lys Ala Ala Gly Trp Thr Leu Asp Met Ile Gly Ala Ser Ala Met
        195                 200                 205
Thr Trp Glu Met Gln His Val Leu Gly His His Pro Tyr Thr Asn Leu
    210                 215                 220
Ile Glu Met Glu Asn Gly Leu Ala Lys Val Lys Gly Ala Asp Val Asp
225                 230                 235                 240
Pro Lys Lys Val Asp Gln Glu Ser Asp Pro Asp Val Phe Ser Thr Tyr
            245                 250                 255
Pro Met Leu Arg Leu His Pro Trp His Arg Gln Arg Phe Tyr His Lys
            260                 265                 270
Phe Gln His Leu Tyr Ala Pro Phe Ile Phe Gly Phe Met Thr Ile Asn
        275                 280                 285
Lys Val Ile Ser Gln Asp Val Gly Val Val Leu Arg Lys Arg Leu Phe
    290                 295                 300
Gln Ile Asp Ala Asn Cys Arg Tyr Gly Ser Pro Trp Tyr Val Ala Arg
305                 310                 315                 320
Phe Trp Ile Met Lys Leu Leu Thr Thr Leu Tyr Thr Val Ala Leu Pro
            325                 330                 335
Met Tyr Met Gln Gly Pro Ala Gln Gly Leu Lys Leu Phe Phe Met Ala
            340                 345                 350

FIG.7A

His Phe Thr Cys Gly Glu Val Leu Ala Thr Met Phe Ile Val Asn His
        355             360             365
Ile Ile Glu Gly Val Ser Tyr Ala Ser Lys Asp Ala Val Lys Gly Val
        370             375             380
Met Ala Pro Pro Arg Thr Val His Gly Val Thr Pro Met Gln Val Thr
385             390             395             400
Gln Lys Ala Leu Ser Ala Ala Glu Ser Thr Lys Ser Asp Ala Asp Lys
                405             410             415
Thr Thr Met Ile Pro Leu Asn Asp Trp Ala Ala Val Gln Cys Gln Thr
            420             425             430
Ser Val Asn Trp Ala Val Gly Ser Trp Phe Trp Asn His Phe Ser Gly
        435             440             445
Gly Leu Asn His Gln Ile Glu His His Cys Phe Pro Gln Asn Pro His
    450             455             460
Thr Val Asn Val Tyr Ile Ser Gly Ile Val Lys Glu Thr Cys Glu Glu
465             470             475             480
Tyr Gly Val Pro Tyr Gln Ala Glu Ile Ser Leu Phe Ser Ala Tyr Phe
            485             490             495
Lys Met Leu Ser His Leu Arg Thr Leu Gly Asn Glu Asp Leu Thr Ala
            500             505             510
Arg Ser Thr
        515

FIG.7B

Gene Sequence of Delta 4-Desaturase of *Thraustochytrium aureum* (ATCC 34304) from plasmid pRTA6

```
Met Thr Val Gly Phe Asp Glu Thr Val Thr Met Asp Thr Val Arg Asn
 1           5                    10                  15
His Asn Met Pro Asp Asp Ala Trp Cys Ala Ile His Gly Thr Val Tyr
             20                  25                  30
Asp Ile Thr Lys Phe Ser Lys Val His Pro Gly Gly Asp Ile Ile Met
             35                  40                  45
Leu Ala Ala Gly Lys Glu Ala Thr Ile Leu Phe Glu Thr Tyr His Ile
     50                  55                  60
Lys Gly Val Pro Asp Ala Val Leu Arg Lys Tyr Lys Val Gly Lys Leu
65                   70                  75                  80
Pro Gln Gly Lys Lys Gly Glu Thr Ser His Met Pro Thr Gly Leu Asp
                 85                  90                  95
Ser Ala Phe Tyr Tyr Ser Trp Asp Ser Glu Phe Tyr Arg Val Leu Arg
             100                 105                 110
Glu Arg Val Ala Lys Lys Leu Ala Glu Pro Gly Leu Met Gln Arg Ala
         115                 120                 125
Arg Met Glu Leu Trp Ala Lys Ala Ile Phe Leu Leu Ala Gly Phe Trp
     130                 135                 140
Gly Ser Leu Tyr Ala Met Cys Val Leu Asp Pro His Gly Gly Ala Met
145                 150                 155                 160
Val Ala Ala Val Thr Leu Gly Val Phe Ala Ala Phe Val Gly Thr Cys
             165                 170                 175
Ile Gln His Asp Gly Ser His Gly Ala Phe Ser Lys Ser Arg Phe Met
             180                 185                 190
Asn Lys Ala Ala Gly Trp Thr Leu Asp Met Ile Gly Ala Ser Ala Met
         195                 200                 205
Thr Trp Glu Met Gln His Val Leu Gly His His Pro Tyr Thr Asn Leu
     210                 215                 220
Ile Glu Met Glu Asn Gly Leu Ala Lys Val Lys Gly Ala Asp Val Asp
225                 230                 235                 240
Pro Lys Lys Val Asp Gln Glu Ser Asp Pro Asp Val Phe Ser Thr Tyr
             245                 250                 255
Pro Met Leu Arg Leu His Pro Trp His Arg Gln Arg Phe Tyr His Lys
             260                 265                 270
Phe Gln His Leu Tyr Ala Pro Phe Ile Phe Gly Phe Met Thr Ile Asn
         275                 280                 285
Lys Val Ile Ser Gln Asp Val Gly Val Val Leu Arg Lys Arg Leu Phe
     290                 295                 300
Gln Ile Asp Ala Asn Cys Arg Tyr Gly Ser Pro Trp Tyr Val Ala Arg
305                 310                 315                 320
Phe Trp Ile Met Lys Leu Leu Thr Thr Leu Tyr Met Val Ala Leu Pro
             325                 330                 335
Met Tyr Met Gln Gly Pro Ala Gln Gly Leu Lys Leu Phe Phe Met Ala
             340                 345                 350
```

FIG.8A

```
His Phe Thr Cys Gly Glu Val Leu Ala Thr Met Phe Ile Val Asn His
        355             360             365
Ile Ile Glu Gly Val Ser Tyr Ala Ser Lys Asp Ala Val Lys Gly Val
        370         375             380
Met Ala Pro Pro Arg Thr Val His Gly Val Thr Pro Met Gln Val Thr
385             390             395                 400
Gln Lys Ala Leu Ser Ala Ala Glu Ser Thr Lys Ser Asp Ala Asp Lys
            405             410             415
Thr Thr Met Ile Pro Leu Asn Asp Trp Ala Ala Val Gln Cys Gln Thr
        420             425             430
Ser Val Asn Trp Ala Val Gly Ser Trp Phe Trp Asn His Phe Ser Gly
        435             440             445
Gly Leu Asn His Gln Ile Glu His His Cys Phe Pro Gln Asn Pro His
    450             455             460
Thr Val Asn Val Tyr Ile Ser Gly Ile Val Lys Glu Thr Cys Glu Glu
465             470             475                 480
Tyr Gly Val Pro Tyr Gln Ala Glu Ile Ser Leu Phe Ser Ala Tyr Phe
            485             490             495
Lys Met Leu Ser His Leu Arg Thr Leu Gly Asn Glu Asp Leu Thr Ala
            500             505             510
Trp Ser Thr
        515
```

FIG.8B

Gene Sequence of Delta 4-Desaturase of *Thraustochytrium aureum* (ATCC 34304) from plasmid pRTA7

```
Met Thr Val Gly Phe Asp Glu Thr Val Thr Met Asp Thr Val Arg Asn
 1           5                   10                  15
His Asn Met Pro Asp Asp Ala Trp Cys Ala Ile His Gly Thr Val Tyr
            20                  25              30
Asp Ile Thr Lys Phe Ser Lys Val His Pro Gly Gly Asp Ile Ile Met
            35              40              45
Leu Ala Ala Gly Lys Glu Ala Thr Ile Leu Phe Glu Thr Tyr His Ile
     50              55                  60
Lys Gly Val Pro Asp Ala Val Leu Arg Lys Tyr Lys Val Gly Lys Leu
65              70                  75                      80
Pro Gln Gly Lys Lys Gly Glu Thr Ser His Met Pro Thr Gly Leu Asp
                85                  90                  95
Ser Ala Ser Tyr Tyr Ser Trp Asp Ser Glu Phe Tyr Arg Val Leu Arg
            100                 105                 110
Glu Arg Val Ala Lys Lys Leu Ala Glu Pro Gly Leu Met Gln Arg Ala
        115                 120                 125
Arg Met Glu Leu Trp Ala Lys Ala Ile Phe Leu Leu Ala Gly Phe Trp
    130                 135                 140
Gly Ser Leu Tyr Ala Met Cys Val Leu Asp Pro His Gly Gly Ala Met
145             150                 155                 160
Val Ala Ala Val Thr Leu Gly Val Phe Ala Ala Phe Val Gly Thr Cys
                165                 170             175
Ile Gln His Asp Gly Ser His Gly Ala Phe Ser Lys Ser Arg Phe Met
            180             185                 190
Asn Lys Ala Ala Gly Trp Thr Leu Asp Met Ile Gly Ala Ser Ala Met
        195                 200                 205
Thr Trp Glu Met Gln His Val Leu Gly His His Pro Tyr Thr Asn Leu
    210                 215                 220
Ile Glu Met Glu Asn Gly Leu Ala Lys Val Lys Gly Ala Asp Val Asp
225                 230                 235                 240
Pro Lys Lys Val Asp Gln Glu Ser Asp Pro Asp Val Phe Ser Thr Tyr
                245                 250                 255
Pro Met Leu Arg Leu His Pro Trp His Arg Gln Arg Phe Tyr His Lys
            260                 265                 270
Phe Gln His Leu Tyr Ala Pro Leu Ile Phe Gly Phe Met Thr Ile Asn
        275                 280                 285
Lys Val Ile Ser Gln Asp Val Gly Val Val Leu Arg Lys Arg Leu Phe
    290                 295                 300
Gln Ile Asp Ala Asn Cys Arg Tyr Gly Ser Pro Trp Asn Val Ala Arg
305                 310                 315                 320
Phe Trp Ile Met Lys Leu Leu Thr Thr Leu Tyr Met Val Ala Leu Pro
                325                 330                 335
Met Tyr Met Gln Gly Pro Ala Gln Gly Leu Lys Leu Phe Phe Met Ala
            340                 345                 350
```

FIG.9A

His Phe Thr Cys Gly Glu Val Leu Ala Thr Met Phe Ile Val Asn His
        355             360             365
Ile Ile Glu Gly Val Ser Tyr Ala Ser Lys Asp Ala Val Lys Gly Val
        370             375             380
Met Ala Pro Pro Arg Thr Val His Gly Val Thr Pro Met Gln Val Thr
385             390             395             400
Gln Lys Ala Leu Ser Ala Ala Glu Ser Thr Lys Ser Asp Ala Asp Lys
                405             410             415
Thr Thr Met Ile Pro Leu Asn Asp Trp Ala Ala Val Gln Cys Gln Thr
            420             425             430
Ser Val Asn Trp Ala Val Gly Ser Trp Phe Trp Asn His Phe Ser Gly
        435             440             445
Gly Leu Asn His Gln Ile Glu His His Cys Phe Pro Gln Asn Pro His
    450             455             460
Thr Val Asn Val Tyr Ile Ser Gly Ile Val Lys Glu Thr Cys Glu Glu
465             470             475             480
Tyr Gly Val Pro Tyr Gln Ala Glu Ile Ser Leu Phe Ser Ala Tyr Phe
                485             490             495
Lys Met Leu Ser His Leu Arg Thr Leu Gly Asn Glu Asp Leu Thr Ala
            500             505             510
Trp Ser Thr
        515

FIG.9B

Gene Sequence of Delta 4-Desaturase of *Thraustochytrium aureum* (ATCC 34304) from plasmid pRTA8

| | | | | | | | | | | | | | | |
|---|---|---|---|---|---|---|---|---|---|---|---|---|---|---|
| Met 1 | Thr | Val | Gly | Phe 5 | Asp | Glu | Thr | Val | Met 10 | Asp | Thr | Val | Arg 15 | Asn |
| His | Asn | Met | Pro 20 | Asp | Asp | Ala | Trp | Cys 25 | Ala | Ile | His | Gly | Thr 30 | Val | Tyr |
| Asp | Ile | Thr 35 | Lys | Phe | Ser | Lys 40 | Val | His | Pro | Gly | Gly 45 | Asp | Ile | Ile | Met |
| Leu | Ala 50 | Ala | Gly | Lys | Glu 55 | Ala | Thr | Ile | Leu | Phe 60 | Glu | Thr | Tyr | His | Ile |
| Lys 65 | Gly | Val | Pro | Asp 70 | Ala | Val | Leu | Arg | Lys 75 | Tyr | Lys | Val | Gly | Lys | Leu 80 |
| Pro | Gln | Gly | Lys | Lys 85 | Gly | Glu | Thr | Ser | His 90 | Met | Pro | Thr | Gly | Leu 95 | Asp |
| Ser | Ala | Ser | Tyr | Tyr 100 | Ser | Trp | Asp | Ser | Glu 105 | Phe | Tyr | Arg | Val 110 | Leu | Arg |
| Glu | Arg | Val 115 | Ala | Lys | Lys | Leu 120 | Ala | Glu | Pro | Gly | Leu 125 | Met | Gln | Arg | Ala |
| Arg | Met 130 | Glu | Leu | Trp | Ala | Lys 135 | Ala | Ile | Phe | Leu | Leu 140 | Ala | Gly | Phe | Trp |
| Gly 145 | Ser | Leu | Tyr | Ala | Met 150 | Cys | Val | Leu | Asp | Pro 155 | His | Gly | Gly | Ala | Met 160 |
| Val | Ala | Ala | Val | Thr 165 | Leu | Gly | Val | Phe | Ala 170 | Ala | Phe | Val | Gly | Thr 175 | Cys |
| Ile | Gln | His | Asp 180 | Gly | Ser | His | Gly | Ala 185 | Phe | Ser | Lys | Ser | Arg 190 | Phe | Met |
| Asn | Lys | Ala 195 | Ala | Gly | Trp | Thr | Leu 200 | Asp | Met | Ile | Gly | Ala 205 | Ser | Ala | Met |
| Thr | Trp 210 | Glu | Met | Gln | His | Val 215 | Leu | Gly | His | His | Pro 220 | Tyr | Thr | Asn | Leu |
| Ile | Glu 225 | Met | Glu | Asn | Gly 230 | Leu | Ala | Lys | Val | Lys 235 | Gly | Ala | Asp | Val | Asp 240 |
| Pro | Lys | Lys | Val | Asp 245 | Gln | Glu | Ser | Asp | Pro 250 | Asp | Val | Phe | Ser | Thr 255 | Tyr |
| Pro | Met | Leu | Arg 260 | Leu | His | Pro | Trp | His 265 | Arg | Gln | Arg | Phe | Tyr 270 | His | Lys |
| Phe | Gln 275 | His | Leu | Tyr | Ala | Pro 280 | Phe | Ile | Phe | Gly | Ser 285 | Met | Thr | Ile | Asn |
| Lys 290 | Val | Ile | Ser | Gln | Asp 295 | Val | Gly | Val | Val | Leu 300 | Arg | Lys | Arg | Leu | Phe |
| Gln 305 | Ile | Asp | Ala | Asn | Cys 310 | Arg | Tyr | Gly | Ser | Pro 315 | Trp | Tyr | Val | Ala | Arg 320 |
| Phe | Trp | Ile | Met | Lys 325 | Leu | Leu | Thr | Thr | Leu 330 | Tyr | Met | Val | Ala | Leu 335 | Pro |
| Met | Tyr | Met | Gln | Gly 340 | Pro | Ala | Gln | Gly 345 | Leu | Lys | Leu | Phe | Phe 350 | Met | Ala |

FIG.10A

His Phe Thr Cys Gly Glu Val Leu Ala Thr Met Phe Ile Val Asn His
        355                 360                 365
Ile Ile Glu Gly Val Ser Tyr Ala Ser Lys Asp Ala Val Lys Gly Val
        370                 375                 380
Met Ala Pro Pro Arg Thr Val His Gly Val Thr Pro Met Gln Val Thr
385                 390                 395                 400
Gln Lys Ala Leu Ser Ala Ala Glu Ser Ala Lys Ser Asp Ala Asp Lys
                405                 410                 415
Thr Thr Met Ile Pro Leu Asn Asp Trp Ala Ala Val Gln Cys Gln Thr
            420                 425                 430
Ser Val Asn Trp Ala Val Gly Ser Trp Phe Trp Asn His Phe Ser Gly
        435                 440                 445
Gly Leu Asn His Gln Ile Glu His His Cys Phe Pro Gln Asn Pro His
    450                 455                 460
Thr Val Asn Val Tyr Ile Ser Gly Ile Val Lys Glu Thr Cys Glu Glu
465                 470                 475                 480
Tyr Gly Val Pro Tyr Gln Ala Glu Ile Ser Leu Phe Ser Ala Tyr Phe
                485                 490                 495
Lys Met Leu Ser His Leu Arg Thr Leu Gly Asn Glu Asp Leu Thr Ala
            500                 505                 510
Trp Ser Thr
        515

FIG.10B

SEQUENCE ID NO:1
5'-GTBTAYGAYGTBACCGARTGGGTBAAGCGYCAYCCBGGHGGH-3'

SEQUENCE ID NO:2
5'-GGHGCYTCCGCYAACTGGTGGAAGCAYCAGCAYAACGTBCAYCAY-3'

SEQUENCE ID NO:3
5'-RTGRTGVACGTTRTGCTGRTGCTTCCACCAGTTRGCGGARGCDCC-3'

SEQUENCE ID NO:4
5'-TTGATRGTCTARCTYGTRGTRGASAARGGVTGGTAC-3'

SEQUENCE ID NO:5
5'-CATCATCATXGGRAAXARRTGRTG-3'

SEQUENCE ID NO:6
5'-CTACTACTACTACAYCAYACXTAYACXAAY-3'

SEQUENCE ID NO:7
5'-CCCAGTCACGACGTTGTAAAACGACGGCCAG-3'

SEQUENCE ID NO:8
5'-GACGATTAACAAGGTGATTTCCCAGGATGTC

SEQUENCE ID NO:9
5'-GACTAACTCGAGTCACGTGGACCAGGCCGTGAGGTCCT

FIG.11A

SEQUENCE ID NO:10
GACTAACTCGAGTTGACGAGGTTTGTATGTTCGGCGGTTTGCTTG-3'

SEQUENCE ID NO:11
5'-AGCGGATAACAATTTCACACAGGAAACAGC-3'

SEQUENCE ID NO:12
TGGCTACCGTCGTGCTGGATGCAAGTTCCG-3'

SEQUENCE ID NO:13
5'-CGCATGGAATTCATGACGGTCGGGTTTGACGAAACGGTG-3'

SEQUENCE ID NO:14

```
   1 ATGACGGTCG GGTTTGACGA AACGGTGACT ATGGACACGG TCCGCAACCA
  51 CAACATGCCG GACGACGCCT GGTGCGCGAT CCACGGCACC GTGTACGACA
 101 TCACCAAGTT CAGCAAGGTG CACCCCGGCG GGACATCAT CATGCTGGCC
 151 GCTGGCAAGG AGGCCACCAT CCTGTTCGAG ACGTACCACA TCAAGGGCGT
 201 CCCGGACGCG GTGCTGCGCA AGTACAAGGT CGGCAAGCTC CCCCAGGGCA
 251 AGAAGGGCGA AACGAGCCAC ATGCCCACCG GCTCGACTC GGCCTCCTAC
 301 TACTCGTGGG ACAGCGAGTT TTACAGGGTG CTCCGCGAGC GCGTCGCCAA
 351 GAAGCTGGCC GAGCCCGGCC TCATGCAGCG CGCGCGCATG GAGCTCTGGG
 401 CCAAGGCGAT CTTCCTCCTG GCAGGTTTCT GGGGCTCCCT TTACGCCATG
 451 TGCGTGCTAG ACCCGCACGG CGGTGCCATG GTAGCCGCCG TTACGCTCGG
 501 CGTGTTCGCT GCCTTTGTCG GAACTTGCAT CCAGCACGAC GGCAGCCACG
 551 GCGCCTTCTC CAAGTCGCGA TTCATGAACA AGGCGGCGGG CTGGACCCTC
 601 GACATGATCG GCGCGAGCGC GATGACCTGG GAGATGCAGC ACGTTCTTGG
 651 CCACCACCCG TACACCAACC TCATCGAGAT GGAGAACGGT TTGGCCAAGG
 701 TCAAGGGCGC CGACGTCGAC CCGAAGAAGG TCGACCAGGA GAGCGACCCG
 751 GACGTCTTCA GTACGTACCC GATGCTTCGC CTGCACCCGT GGCACCGCCA
 801 GCGGTTTTAC CACAAGTTCC AGCACCTGTA CGCCCCGTTT ATCTTTGGGT
 851 TTATGACGAT TAACAAGGTG ATTTCCCAGG ATGTCGGGGT TGTGCTGCGC
 901 AAGCGCCTGT TCCAGATCGA CGCCAACTGC CGGTATGGCA GCCCCTGGTA
 951 CGTGGCCCGC TTCTGGATCA TGAAGCTCCT CACCACGCTC TACACGGTGG
1001 CGCTTCCCAT GTACATGCAG GGGCCTGCTC AGGGCTTGAA GCTTTTCTTC
1051 ATGGCCCACT TCACCTGCGG AGAGGTCCTC GCCACCATGT TTATTGTCAA
```

FIG.11B

```
1101 CCACATCATC GAGGGCGTCA GCTACGCTTC CAAGGACGCG GTCAAGGGCG
1151 TCATGGCTCC GCCGCGCACT GTGCACGGTG TCACCCCGAT GCAGGTGACG
1201 CAAAAGGCGC TCAGTGCGGC CGAGTCGACC AAGTCGGACG CCGACAAGAC
1251 GACCATGATC CCCCTCAACG ACTGGGCCGC TGTGCAGTGC CAGACCTCTG
1301 TGAACTGGGC TGTCGGGTCG TGGTTTTGGA ACCACTTTTC GGGCGGCCTC
1351 AACCACCAGA TTGAGCACCA CTGCTTCCCC CAAAACCCCC ACACGGTCAA
1401 CGTCTACATC TCGGGCATCG TCAAGGAGAC CTGCGAAGAA TACGGCGTGC
1451 CGTACCAGGC TGAGATCAGC CTCTTCTCTG CCTATTTCAA GATGCTGTCG
1501 CACCTCCGCA CGCTCGGCAA CGAGGACCTC ACGGCCAGGT CCACGTGA
```

SEQUENCE ID NO:15
```
   1 ATGACGGTCG GGTTTGACGA AACGGTGACT ATGGACACGG TCCGCAACCA
  51 TAACATGCCG GACGACGCCT GGTGCGCGAT CCACGGCACC GTGTACGACA
 101 TCACCAAGTT CAGCAAGGTG CACCCCGGCG GGGACATCAT CATGCTGGCC
 151 GCTGGCAAGG AGGCCACCAT CCTGTTCGAG ACGTACCACA TCAAGGGCGT
 201 CCCGGACGCG GTGCTGCGCA AGTACAAGGT CGGCAAGCTC CCCCAGGGCA
 251 AGAAGGGCGA AACGAGCCAC ATGCCCACCG GCTCGACTC GGCCTTCTAC
 301 TACTCGTGGG ACAGCGAGTT TTACAGGGTG CTCCGCGAGC GCGTCGCCAA
 351 GAAGCTGGCC GAGCCCGGCC TCATGCAGCG CGCGCGCATG GAGCTCTGGG
 401 CCAAGGCGAT CTTCCTCCTG GCAGGTTTCT GGGGCTCCCT TTACGCCATG
 451 TGCGTGCTAG ACCCGCACGG CGGTGCCATG GTAGCCGCCG TTACGCTCGG
 501 CGTGTTCGCT GCCTTTGTCG GAACTTGCAT CCAGCACGAC GGCAGCCACG
 551 GCGCCTTCTC CAAGTCGCGA TTCATGAACA AGGCGGCGGG CTGGACCCTC
 601 GACATGATCG GCGCGAGCGC GATGACCTGG GAGATGCAGC ACGTTCTTGG
 651 CCACCACCCG TACACCAACC TCATCGAGAT GGAGAACGGT TTGGCCAAGG
 701 TCAAGGGCGC CGACGTCGAC CCGAAGAAGG TCGACCAGGA GAGCGACCCG
 751 GACGTCTTCA GTACGTACCC GATGCTTCGC CTGCACCCGT GGCACCGCCA
 801 GCGGTTTTAC CACAAGTTCC AGCACCTGTA CGCCCCGTTT ATCTTTGGGT
 851 TTATGACGAT TAACAAGGTG ATTTCCCAGG ATGTCGGGGT TGTGCTGCGC
 901 AAGCGCCTGT TCCAGATCGA CGCCAACTGC CGGTATGGCA GCCCCTGGTA
 951 CGTGGCCCGC TTCTGGATCA TGAAGCTCCT CACCACGCTC TACATGGTGG
1001 CGCTTCCCAT GTACATGCAG GGGCCTGCTC AGGGCTTGAA GCTTTTCTTC
1051 ATGGCCCACT TCACCTGCGG AGAGGTCCTC GCCACCATGT TTATTGTCAA
1101 CCACATCATC GAGGGCGTCA GCTACGCTTC CAAGGACGCG GTCAAGGGCG
1151 TCATGGCTCC GCCGCGCACT GTGCACGGTG TCACCCCGAT GCAGGTGACG
1201 CAAAAGGCGC TCAGTGCGGC CGAGTCGACC AAGTCGGACG CCGACAAGAC
1251 GACCATGATC CCCCTCAACG ACTGGGCCGC TGTGCAGTGC CAGACCTCTG
1301 TGAACTGGGC TGTCGGGTCG TGGTTTTGGA ACCACTTTTC GGGCGGCCTC
1351 AACCACCAGA TTGAGCACCA CTGCTTCCCC CAAAACCCCC ACACGGTCAA
1401 CGTCTACATC TCAGGCATCG TCAAGGAGAC CTGCGAAGAA TACGGCGTGC
1451 CGTACCAGGC TGAGATCAGC CTCTTCTCTG CCTATTTCAA GATGCTGTCG
1501 CACCTCCGCA CGCTCGGCAA CGAGGACCTC ACGGCCTGGT CCACGTGA
```

FIG.11C

SEQUENCE ID NO:16
    1 ATGACGGTCG GGTTTGACGA AACGGTGACT ATGGACACGG TCCGCAACCA
   51 CAACATGCCG GACGACGCCT GGTGCGCGAT CCACGGCACC GTGTACGACA
  101 TCACCAAGTT CAGCAAGGTG CACCCCGGCG GGACATCAT CATGCTGGCC
  151 GCTGGCAAGG AGGCCACCAT CCTGTTCGAG ACCTACCACA TCAAGGGCGT
  201 CCCGGACGCG GTGCTGCGCA AGTACAAGGT CGGCAAGCTC CCCCAGGGCA
  251 AGAAGGGCGA AACGAGCCAC ATGCCCACCG GCTCGACTC GGCCTCCTAC
  301 TACTCGTGGG ACAGCGAGTT TTACAGGGTG CTCCGCGAGC GCGTCGCCAA
  351 GAAGCTGGCC GAGCCCGGCC TCATGCAGCG CGCGCGCATG GAGCTCTGGG
  401 CCAAGGCGAT CTTCCTCCTG GCAGGTTTCT GGGGCTCCCT TTACGCCATG
  451 TGCGTGCTAG ACCCGCACGG CGGTGCCATG GTAGCCGCCG TTACGCTCGG
  501 CGTGTTCGCT GCCTTTGTCG GAACTTGCAT CCAGCACGAC GGCAGCCACG
  551 GCGCCTTCTC CAAGTCGCGA TTCATGAACA AGGCGGCGGG CTGGACCCTC
  601 GACATGATCG GCGCGAGCGC GATGACCTGG GAGATGCAGC ACGTTCTTGG
  651 TCACCACCCG TACACCAACC TCATCGAGAT GGAGAACGGT TTGGCCAAGG
  701 TCAAGGGCGC CGACGTCGAC CCGAAGAAGG TCGACCAGGA GAGCGACCCG
  751 GACGTCTTCA GTACGTACCC GATGCTTCGC CTGCACCCGT GGCACCGCCA
  801 GCGGTTTTAC CACAAGTTCC AGCACCTGTA CGCCCCGCTT ATCTTTGGGT
  851 TTATGACGAT TAACAAGGTG ATTTCCCAGG ATGTCGGGGT TGTGCTGCGC
  901 AAGCGCCTGT TCCAGATCGA CGCCAACTGC CGGTATGGCA GCCCCTGGAA
  951 CGTGGCCCGC TTCTGGATCA TGAAGCTCCT CACCACGCTC TACATGGTGG
 1001 CGCTTCCCAT GTACATGCAG GGGCCTGCTC AGGGCTTGAA GCTTTTCTTC
 1051 ATGGCCCACT TCACCTGCGG AGAGGTCCTC GCCACCATGT TTATTGTCAA
 1101 CCACATCATC GAGGGCGTCA GCTACGCTTC CAAGGACGCG GTCAAGGGCG
 1151 TCATGGCTCC GCCGCGCACT GTGCACGGTG TCACCCCGAT GCAGGTGACG
 1201 CAAAAGGCGC TCAGTGCGGC CGAGTCGACC AAGTCGGACG CCGACAAGAC
 1251 GACCATGATC CCCCTCAACG ACTGGGCCGC TGTGCAGTGC CAGACCTCTG
 1301 TGAACTGGGC TGTCGGGTCG TGGTTTTGGA ACCACTTTTC GGGCGGCCTA
 1351 AACCACCAGA TTGAGCACCA CTGCTTCCCC CAAAACCCCC ACACGGTCAA
 1401 CGTCTACATC TCGGGCATCG TCAAGGAGAC CTGCGAAGAA TACGGCGTGC
 1451 CGTACCAGGC TGAGATCAGC CTCTTCTCTG CCTATTTCAA GATGCTGTCG
 1501 CACCTCCGCA CGCTCGGCAA CGAGGACCTC ACGGCCTGGT CCACGTGA

SEQUENCE ID NO:17
    1 ATGACGGTCG GGTTTGACGA AACGGTGACT ATGGACACGG TCCGCAACCA
   51 CAACATGCCG GACGACGCCT GGTGCGCGAT CCACGGCACC GTGTACGACA
  101 TCACCAAGTT CAGCAAGGTG CACCCCGGCG GGACATCAT CATGCTGGCC
  151 GCTGGCAAGG AGGCCACCAT CCTGTTCGAG ACCTACCACA TCAAGGGCGT
  201 CCCGGACGCG GTGCTGCGCA AGTACAAGGT CGGCAAGCTC CCCCAGGGCA
  251 AGAAGGGCGA AACGAGCCAC ATGCCCACCG GCTCGACTC GGCCTCCTAC
  301 TACTCGTGGG ACAGCGAGTT TTACAGGGTG CTCCGCGAGC GCGTCGCCAA
  351 GAAGCTGGCC GAGCCCGGCC TCATGCAGCG CGCGCGCATG GAGCTCTGGG

FIG.11D

```
 401 CCAAGGCGAT CTTCCTCCTG GCAGGTTTCT GGGGCTCCCT TTACGCCATG
 451 TGCGTGCTAG ACCCGCACGG CGGTGCCATG GTAGCCGCCG TTACGCTCGG
 501 CGTGTTCGCT GCCTTTGTCG GAACTTGCAT CCAGCACGAC GGCAGCCACG
 551 GCGCCTTCTC CAAGTCGCGA TTCATGAACA AGGCGGCGGG CTGGACCCTC
 601 GACATGATCG GCGCGAGTGC GATGACCTGG GAGATGCAGC ACGTTCTTGG
 651 CCACCACCCG TACACCAACC TCATCGAGAT GGAGAACGGT TTGGCCAAGG
 701 TCAAGGGCGC CGACGTCGAC CCGAAGAAGG TCGACCAGGA GAGCGACCCG
 751 GACGTCTTCA GTACGTACCC GATGCTTCGC CTGCACCCGT GGCACCGCCA
 801 GCGGTTTTAC CACAAGTTCC AGCACCTGTA CGCCCCGTTT ATCTTTGGGT
 851 CTATGACGAT TAACAAGGTG ATTTCCCAGG ATGTCGGGGT TGTGCTGCGC
 901 AAGCGCCTGT TCCAGATCGA CGCCAACTGC CGGTATGGCA GCCCCTGGTA
 951 CGTGGCCCGC TTCTGGATCA TGAAGCTCCT CACCACGCTC TACATGGTGG
1001 CGCTTCCCAT GTACATGCAG GGGCCTGCTC AGGGCTTGAA GCTTTTCTTC
1051 ATGGCCCACT TCACCTGCGG AGAGGTCCTC GCCACCATGT TTATTGTCAA
1101 CCACATCATC GAGGGCGTCA GCTACGCTTC CAAGGACGCG GTCAAGGGCG
1151 TCATGGCTCC GCCGCGCACT GTGCACGGTG TCACCCCGAT GCAGGTGACG
1201 CAAAAGGCGC TCAGTGCGGC CGAGTCGGCC AAGTCGGACG CCGACAAGAC
1251 GACCATGATC CCCCTCAACG ACTGGGCCGC TGTGCAGTGC CAGACCTCTG
1301 TGAACTGGGC TGTCGGGTCG TGGTTTTGGA ACCACTTTTC GGGCGGCCTC
1351 AACCACCAGA TTGAGCACCA CTGCTTCCCC CAAAACCCCC ACACGGTCAA
1401 CGTCTACATC TCGGGCATCG TCAAGGAGAC CTGCGAAGAA TACGGCGTGC
1451 CGTACCAGGC TGAGATCAGC CTCTTCTCTG CCTATTTCAA GATGCTGTCG
1501 CACCTCCGCA CGCTCGGCAA CGAGGACCTC ACGGCCTGGT CCACGTGA

SEQUENCE ID NO:18
  1 MTVGFDETVT MDTVRNHNMP DDAWCAIHGT VYDITKFSKV HPGGDIIMLA
 51 AGKEATILFE TYHIKGVPDA VLRKYKVGKL PQGKKGETSH MPTGLDSASY
101 YSWDSEFYRV LRERVAKKLA EPGLMQRARM ELWAKAIFLL AGFWGSLYAM
151 CVLDPHGGAM VAAVTLGVFA AFVGTCIQHD GSHGAFSKSR FMNKAAGWTL
201 DMIGASAMTW EMQHVLGHHP YTNLIEMENG LAKVKGADVD PKKVDQESDP
251 DVFSTYPMLR LHPWHRQRFY HKFQHLYAPF IFGFMTINKV ISQDVGVVLR
301 KRLFQIDANC RYGSPWYVAR FWIMKLLTTL YTVALPMYMQ GPAQGLKLFF
351 MAHFTCGEVL ATMFIVNHII EGVSYASKDA VKGVMAPPRT VHGVTPMQVT
401 QKALSAAEST KSDADKTTMI PLNDWAAVQC QTSVNWAVGS WFWNHFSGGL
451 NHQIEHHCFP QNPHTVNVYI SGIVKETCEE YGVPYQAEIS LFSAYFKMLS
501 HLRTLGNEDL TARST*

SEQUENCE ID NO:19
  1 MTVGFDETVT MDTVRNHNMP DDAWCAIHGT VYDITKFSKV HPGGDIIMLA
 51 AGKEATILFE TYHIKGVPDA VLRKYKVGKL PQGKKGETSH MPTGLDSAFY
```

FIG.11E

```
101 YSWDSEFYRV LRERVAKKLA EPGLMQRARM ELWAKAIFLL AGFWGSLYAM
151 CVLDPHGGAM VAAVTLGVFA AFVGTCIQHD GSHGAFSKSR FMNKAAGWTL
201 DMIGASAMTW EMQHVLGHHP YTNLIEMENG LAKVKGADVD PKKVDQESDP
251 DVFSTYPMLR LHPWHRQRFY HKFQHLYAPF IFGFMTINKV ISQDVGVVLR
301 KRLFQIDANC RYGSPWYVAR FWIMKLLTTL YMVALPMYMQ GPAQGLKLFF
351 MAHFTCGEVL ATMFIVNHII EGVSYASKDA VKGVMAPPRT VHGVTPMQVT
401 QKALSAAEST KSDADKTTMI PLNDWAAVQC QTSVNWAVGS WFWNHFSGGL
451 NHQIEHHCFP QNPHTVNVYI SGIVKETCEE YGVPYQAEIS LFSAYFKMLS
501 HLRTLGNEDL TAWST*

SEQUENCE ID NO:20
  1 MTVGFDETVT MDTVRNHNMP DDAWCAIHGT VYDITKFSKV HPGGDIIMLA
 51 AGKEATILFE TYHIKGVPDA VLRKYKVGKL PQGKKGETSH MPTGLDSASY
101 YSWDSEFYRV LRERVAKKLA EPGLMQRARM ELWAKAIFLL AGFWGSLYAM
151 CVLDPHGGAM VAAVTLGVFA AFVGTCIQHD GSHGAFSKSR FMNKAAGWTL
201 DMIGASAMTW EMQHVLGHHP YTNLIEMENG LAKVKGADVD PKKVDQESDP
251 DVFSTYPMLR LHPWHRQRFY HKFQHLYAPL IFGFMTINKV ISQDVGVVLR
301 KRLFQIDANC RYGSPWNVAR FWIMKLLTTL YMVALPMYMQ GPAQGLKLFF
351 MAHFTCGEVL ATMFIVNHII EGVSYASKDA VKGVMAPPRT VHGVTPMQVT
401 QKALSAAEST KSDADKTTMI PLNDWAAVQC QTSVNWAVGS WFWNHFSGGL
451 NHQIEHHCFP QNPHTVNVYI SGIVKETCEE YGVPYQAEIS LFSAYFKMLS
501 HLRTLGNEDL TAWST*

SEQUENCE ID NO:21
  1 MTVGFDETVT MDTVRNHNMP DDAWCAIHGT VYDITKFSKV HPGGDIIMLA
 51 AGKEATILFE TYHIKGVPDA VLRKYKVGKL PQGKKGETSH MPTGLDSASY
101 YSWDSEFYRV LRERVAKKLA EPGLMQRARM ELWAKAIFLL AGFWGSLYAM
151 CVLDPHGGAM VAAVTLGVFA AFVGTCIQHD GSHGAFSKSR FMNKAAGWTL
201 DMIGASAMTW EMQHVLGHHP YTNLIEMENG LAKVKGADVD PKKVDQESDP
251 DVFSTYPMLR LHPWHRQRFY HKFQHLYAPF IFGSMTINKV ISQDVGVVLR
301 KRLFQIDANC RYGSPWYVAR FWIMKLLTTL YMVALPMYMQ GPAQGLKLFF
351 MAHFTCGEVL ATMFIVNHII EGVSYASKDA VKGVMAPPRT VHGVTPMQVT
401 QKALSAAESA KSDADKTTMI PLNDWAAVQC QTSVNWAVGS WFWNHFSGGL
451 NHQIEHHCFP QNPHTVNVYI SGIVKETCEE YGVPYQAEIS LFSAYFKMLS
501 HLRTLGNEDL TAWST*
```

FIG.11F

SEQUENCE ID NO:22
```
ATGGAGCAGC TGAAGGCCTT TGATAATGAA GTCAATGCTT TCTTGGACAA CATGTTTGGA    60
CCACGAGATT CTCGAGTTCG CGGGTGGTTC CTGCTGGACT CTTACCTTCC CACCTTCATC   120
CTCACCATCA CGTACCTGCT CTCGATATGG CTGGGTAACA AGTACATGAA GAACAGGCCT   180
GCTCTGTCTC TCAGGGGCAT CCTCACCTTG TATAACCTCG CAATCACACT TCTTTCTGCG   240
TATATGCTGG TGGAGCTCAT CCTCTCCAGC TGGGAAGGAG GTTACAACTT GCAGTGTCAG   300
AATCTCGACA GTGCAGGAGA AGGTGATGTC CGGGTAGCCA AGGTCTTGTG GTGGTACTAC   360
TTCTCCAAAC TAGTGGAGTT CCTGGACACG ATTTTCTTTG TTCTACGAAA AAAGACCAAT   420
CAGATCACCT TCCTTCATGT CTATCACCAC GCGTCCATGT TCAACATCTG GTGGTGTGTT   480
TTGAACTGGA TACCTTGTGG TCAAAGCTTC TTTGGACCCA CCCTGAACAG CTTTATCCAC   540
ATTCTCATGT ACTCCTACTA CGGCCTGTCT GTGTTCCCGT CCATGCACAA GTACCTTTGG   600
TGGAAGAAGT ACCTCACACA GGCTCAGCTG GTGCAGTTCG TACTCACCAT CACGCACACG   660
CTGAGTGCCG TGGTGAAGCC CTGTGGCTTC CCCTTTGGCT GTCTCATCTT CCAGTCTTCC   720
TATATGATGA CGCTGGTCAT CCTGTTCTTA AACTTCTATA TTCAGACATA CCGGAAAAAG   780
CCAGTGAAGA AAGAGCTGCA AGAGAAAGAA GTGAAGAATG GTTTCCCCAA AGCCCACTTA   840
ATTGTGGCTA ATGGCATGAC GGACAAGAAG GCTCAATAA                          879
```

SEQUENCE ID NO:23
```
Met Glu Gln Leu Lys Ala Phe Asp Asn Glu Val Asn Ala Phe Leu Asp
 1               5                  10                  15
Asn Met Phe Gly Pro Arg Asp Ser Arg Val Arg Gly Trp Phe Leu Leu
                20                  25                  30
Asp Ser Tyr Leu Pro Thr Phe Ile Leu Thr Ile Thr Tyr Leu Leu Ser
                35                  40                  45
Ile Trp Leu Gly Asn Lys Tyr Met Lys Asn Arg Pro Ala Leu Ser Leu
        50                  55                  60
Arg Gly Ile Leu Thr Leu Tyr Asn Leu Ala Ile Thr Leu Leu Ser Ala
65                  70                  75                  80
Tyr Met Leu Val Glu Leu Ile Leu Ser Ser Trp Glu Gly Gly Tyr Asn
                85                  90                  95
Leu Gln Cys Gln Asn Leu Asp Ser Ala Gly Glu Gly Asp Val Arg Val
               100                 105                 110
Ala Lys Val Leu Trp Trp Tyr Tyr Phe Ser Lys Leu Val Glu Phe Leu
               115                 120                 125
Asp Thr Ile Phe Phe Val Leu Arg Lys Lys Thr Asn Gln Ile Thr Phe
       130                 135                 140
Leu His Val Tyr His His Ala Ser Met Phe Asn Ile Trp Trp Cys Val
145                 150                 155                 160
Leu Asn Trp Ile Pro Cys Gly Gln Ser Phe Phe Gly Pro Thr Leu Asn
               165                 170                 175
Ser Phe Ile His Ile Leu Met Tyr Ser Tyr Tyr Gly Leu Ser Val Phe
               180                 185                 190
```

FIG.11G

| Pro | Ser | Met | His | Lys | Tyr | Leu | Trp | Trp | Lys | Lys | Tyr | Leu | Thr | Gln | Ala |
| | | 195 | | | | | 200 | | | | | 205 | | | |

Gln Leu Val Gln Phe Val Leu Thr Ile Thr His Thr Leu Ser Ala Val
        210             215             220
Val Lys Pro Cys Gly Phe Pro Phe Gly Cys Leu Ile Phe Gln Ser Ser
225         230             235                 240
Tyr Met Met Thr Leu Val Ile Leu Phe Leu Asn Phe Tyr Ile Gln Thr
            245             250                 255
Tyr Arg Lys Lys Pro Val Lys Lys Glu Leu Gln Glu Lys Glu Val Lys
        260             265             270
Asn Gly Phe Pro Lys Ala His Leu Ile Val Ala Asn Gly Met Thr Asp
        275             280             285
Lys Lys Ala Gln
        290

SEQUENCE ID NO:24
ccagtgtgct ggaattcagg tactactact acaccatact tacacgaacc tgatcgagat     60
ggagaacggc acccaaaagg tcacccacgc cgacgtcgac cccaagaagg ccgaccagga    120
gagcgacccg gacgtcttca gcacctaccc catgctccgt ctgcacccgt ggcaccgcaa    180
gcgcttctac caccgcttcc agcacctgta cgcgccgctg ctcttcggtt tcatgaccat    240
caacaaggtg atcacccagg atgtgggagt tgtcctcagc aagcgtctgt ttcagatcga    300
tgccaactgc cgttacgcca gcaagtcgta cgttcgcgcg ttctggatca tgaagctgct    360
caccgtcctc tacatggtcg ccctccccgt gtacaccag ggccttgtcg acgggctcaa    420
gctcttcttc atcgcccact tttcgtgcgg cgagctgctg ccaccatgt tcatcgtcaa    480
ccacatcatc gagggcgtct cgtacgcctc caaggactct gtcaagggca ccatggcgcc    540
gccgcgcacg gtgcacggcg tgaccccgat gcatgacacc cgcgacgcgc tcggcaagga    600
gaaggcagcc accaagcacg tgccgctcaa cgactgggcc gcggtccagt gccagacctc    660
ggtcaactgg tcgatcggct cgtggttctg gaaccacttc tccggcgggc tcaaccacca    720
gatcgagcac caccttttcc ccatgatgat gatg    754

SEQUENCE ID NO:25
Gln Cys Ala Gly Ile Gln Val Leu Leu Leu His His Thr Tyr Thr Asn
 1           5               10              15
Leu Ile Glu Met Glu Asn Gly Thr Gln Lys Val Thr His Ala Asp Val
            20              25              30
Asp Pro Lys Lys Ala Asp Gln Glu Ser Asp Pro Asp Val Phe Ser Thr
        35              40              45
Tyr Pro Met Leu Arg Leu His Pro Trp His Arg Lys Arg Phe Tyr His
 50              55              60

FIG.11H

```
Arg Phe Gln His Leu Tyr Ala Pro Leu Leu Phe Gly Phe Met Thr Ile
 65              70                  75                  80
Asn Lys Val Ile Thr Gln Asp Val Gly Val Val Leu Ser Lys Arg Leu
             85                  90                  95
Phe Gln Ile Asp Ala Asn Cys Arg Tyr Ala Ser Lys Ser Tyr Val Ala
            100                 105             110
Arg Phe Trp Ile Met Lys Leu Leu Thr Val Leu Tyr Met Val Ala Leu
            115             120                 125
Pro Val Tyr Thr Gln Gly Leu Val Asp Gly Leu Lys Leu Phe Phe Ile
            130             135                 140
Ala His Phe Ser Cys Gly Glu Leu Leu Ala Thr Met Phe Ile Val Asn
145             150                 155                 160
His Ile Ile Glu Gly Val Ser Tyr Ala Ser Lys Asp Ser Val Lys Gly
                165                 170                 175
Thr Met Ala Pro Pro Arg Thr Val His Gly Val Thr Pro Met His Asp
            180                 185                 190
Thr Arg Asp Ala Leu Gly Lys Glu Lys Ala Ala Thr Lys His Val Pro
            195             200                 205
Leu Asn Asp Trp Ala Ala Val Gln Cys Gln Thr Ser Val Asn Trp Ser
210             215                 220
Ile Gly Ser Trp Phe Trp Asn His Phe Ser Gly Gly Leu Asn His Gln
225             230                 235                 240
Ile Glu His His Leu Phe Pro Met Met Met Met
            245                 250
```

FIG. 11I

```
Met Glu Gln Leu Lys Ala Phe Asp Asn Glu Val Asn Ala Phe Leu Asp
 1               5                  10                  15
Asn Met Phe Gly Pro Arg Asp Ser Arg Val Arg Gly Trp Phe Leu Leu
             20                  25                  30
Asp Ser Tyr Leu Pro Thr Phe Ile Leu Thr Ile Thr Tyr Leu Leu Ser
         35                  40                  45
Ile Trp Leu Gly Asn Lys Tyr Met Lys Asn Arg Pro Ala Leu Ser Leu
     50                  55                  60
Arg Gly Ile Leu Thr Leu Tyr Asn Leu Ala Ile Thr Leu Leu Ser Ala
 65              70                  75                  80
Tyr Met Leu Val Glu Leu Ile Leu Ser Ser Trp Glu Gly Gly Tyr Asn
                 85                  90                  95
Leu Gln Cys Gln Asn Leu Asp Ser Ala Gly Glu Gly Asp Val Arg Val
             100                 105                 110
Ala Lys Val Leu Trp Trp Tyr Tyr Phe Ser Lys Leu Val Glu Phe Leu
             115                 120                 125
Asp Thr Ile Phe Phe Val Leu Arg Lys Lys Thr Asn Gln Ile Thr Phe
         130                 135                 140
Leu His Val Tyr His His Ala Ser Met Phe Asn Ile Trp Trp Cys Val
145                 150                 155                 160
Leu Asn Trp Ile Pro Cys Gly Gln Ser Phe Phe Gly Pro Thr Leu Asn
                 165                 170                 175
Ser Phe Ile His Ile Leu Met Tyr Ser Tyr Tyr Gly Leu Ser Val Phe
             180                 185                 190
Pro Ser Met His Lys Tyr Leu Trp Trp Lys Lys Tyr Leu Thr Gln Ala
         195                 200                 205
Gln Leu Val Gln Phe Val Leu Thr Ile Thr His Thr Leu Ser Ala Val
         210                 215                 220
Val Lys Pro Cys Gly Phe Pro Phe Gly Cys Leu Ile Phe Gln Ser Ser
225                 230                 235                 240
Tyr Met Met Thr Leu Val Ile Leu Phe Leu Asn Phe Tyr Ile Gln Thr
             245                 250                 255
Tyr Arg Lys Lys Pro Val Lys Lys Glu Leu Gln Glu Lys Glu Val Lys
             260                 265                 270
Asn Gly Phe Pro Lys Ala His Leu Ile Val Ala Asn Gly Met Thr Asp
         275                 280                 285
Lys Lys Ala Gln
         290
```

FIG.12

```
ccagtgtgct ggaattcagg tactactact acaccatact tacacgaacc tgatcgagat    60
ggagaacggc acccaaaagg tcacccacgc cgacgtcgac cccaagaagg ccgaccagga   120
gagcgacccg gacgtcttca gcacctaccc catgctccgt ctgcacccgt ggcaccgcaa   180
gcgcttctac caccgcttcc agcacctgta cgcgccgctg ctcttcggtt tcatgaccat   240
caacaaggtg atcacccagg atgtgggagt tgtcctcagc aagcgtctgt ttcagatcga   300
tgccaactgc cgttacgcca gcaagtcgta cgttgcgcgc ttctggatca tgaagctgct   360
caccgtcctc tacatggtcg ccctccccgt gtacacccag ggccttgtcg acgggctcaa   420
gctcttcttc atcgcccact tttcgtgcgg cgagctgctg gccaccatgt tcatcgtcaa   480
ccacatcatc gagggcgtct cgtacgcctc caaggactct gtcaagggca ccatggcgcc   540
gccgcgcacg gtgcacggcg tgaccccgat gcatgacacc cgcgacgcgc tcggcaagga   600
gaaggcagcc accaagcacg tgccgctcaa cgactgggcc gcggtccagt gccagacctc   660
ggtcaactgg tcgatcggct cgtggttctg gaaccacttc tccggcgggc tcaaccacca   720
gatcgagcac cacctttcc  ccatgatgat gatg                              754
```

FIG. 13

Gln Cys Ala Gly Ile Gln Val Leu Leu Leu His His Thr Tyr Thr Asn
1           5               10              15
Leu Ile Glu Met Glu Asn Gly Thr Gln Lys Val Thr His Ala Asp Val
            20              25              30
Asp Pro Lys Lys Ala Asp Gln Glu Ser Asp Pro Asp Val Phe Ser Thr
        35              40              45
Tyr Pro Met Leu Arg Leu His Pro Trp His Arg Lys Arg Phe Tyr His
    50              55              60
Arg Phe Gln His Leu Tyr Ala Pro Leu Leu Phe Gly Phe Met Thr Ile
65              70              75              80
Asn Lys Val Ile Thr Gln Asp Val Gly Val Val Leu Ser Lys Arg Leu
            85              90              95
Phe Gln Ile Asp Ala Asn Cys Arg Tyr Ala Ser Lys Ser Tyr Val Ala
        100             105             110
Arg Phe Trp Ile Met Lys Leu Leu Thr Val Leu Tyr Met Val Ala Leu
    115             120             125
Pro Val Tyr Thr Gln Gly Leu Val Asp Gly Leu Lys Leu Phe Phe Ile
    130             135             140
Ala His Phe Ser Cys Gly Glu Leu Leu Ala Thr Met Phe Ile Val Asn
145             150             155             160
His Ile Ile Glu Gly Val Ser Tyr Ala Ser Lys Asp Ser Val Lys Gly
            165             170             175
Thr Met Ala Pro Pro Arg Thr Val His Gly Val Thr Pro Met His Asp
            180             185             190
Thr Arg Asp Ala Leu Gly Lys Glu Lys Ala Ala Thr Lys His Val Pro
    195             200             205
Leu Asn Asp Trp Ala Ala Val Gln Cys Gln Thr Ser Val Asn Trp Ser
    210             215             220
Ile Gly Ser Trp Phe Trp Asn His Phe Ser Gly Gly Leu Asn His Gln
225             230             235             240
Ile Glu His His Leu Phe Pro Met Met Met Met
            245             250

FIG.14

```
SCORES Initl: 1077  Initn: 1365  Pot: 1371
>>/amd_mnt/home/thurmond/taclone/prta-7.pep    (516 aa)
initn: 1365  initl: 1077  opt: 1371
Smith-Waterman score:1371;  79.1% identity in 249 aa overlap
(5-247:212-460)
```

```
                                   10        20        30
saa.pep                      QCAGTQVLLLHHTYTNLIEMENGTQKVTHADVDP
                             :| :| || |||||||||| || |||||
prta-7.pep SHGAFSKSRFMNKAAGWTLDMIGASAMTWEMQHVLGHHPYTNLIEMENGLAKVKGADVDP
                   190       200       210       220       230       240

40        50        60        70        80        90
saa.pep    KKADQESDPDVFSTYPMLRLHPWHRKRFYHRFQHLYAPLLFGFMTINKVITQDVGVVLSK
           ||:||||||||||||||||||||||:||||:||||||||:||||||||||:|||||||||
prta-7.pep KKVDQESDPDVFSTYPMLRLHPWHRQRFYHKFQHLYAPLIFGFMTINKVISQDVGVVLSK
                   250       260       270       280       290       300

100       110       120       130       140       150
saa.pep    RLFQIDANCRYASKSYVARFWIMKLLTVLYMVALPVYTQGLVDGLKLFFIAHFSCGELLA
           |||||||||||:|   |||||||||||||:|||||| :||||||||||||:|||:|||:||
prta-7.pep RLFQIDANCRYGSKSYVARFWIMKLLTTLYMVALPMYTQGLVDGLKLFFMAHFTCGEVLA
                   310       320       330       340       350       360

160       170       180       190       200
saa.pep    TMFIVNHIIEGVSYASKDSVKGTMAPPRTVHGVTPMHDTRDALGKEKAA------TKHVP
           ||||||||||||||||||:|||:||||||||||||||: |: ||: :::    | :|
prta-7.pep TMFIVNHIIEGVSYASKDAVKGVMAPPRTVHGVTPMQVTQKALSAAESTKSDADKTTMIP
                   370       380       390       400       410       420

210       220       230       240       250
saa.pep    LNDWAAVQCQTSVNWSIGSWFWNHFSGGLNHQIEHHLFPMMMM
           ||||||||||||||||::|||||||||||||||||||| ||:
prta-7.pep LNDWAAVQCQTSVNWAVGSWFWNHFSGGLNHQIEHHCFPQNPHTVNVYISGIVKETCEEY
                   430       440       450       460       470       480 prta-7.pep GVPYQAEISLFSAYFKMLSHLRTLGNEDLTAWSTX
                   490       500       510
```

FIG.15

```
   1 ATGACGGTGG GCGGCGATGA GGTGTACAGC ATGGCGCAGG TGCGCGACCA
  51 CAACACCCCG GACGACGCCT GGTGCGCCAT CCACGGCGAG GTGTACGAGC
 101 TGACCAAGTT CGCCCGCACC CACCCCGGGG GGGACATCAT CTTGCTGGCC
 151 GCCGGCAAGG AGGCCACCAT CCTGTTCGAG ACGTACCACG TGCGCCCCAT
 201 CTCCGACGCG GTCCTGCGCA AGTACCGCAT CGGCAAGCTC GCCGCCGCCG
 251 GCAAGGATGA GCCGGCCAAC GACAGCACCT ACTACAGCTG GACAGCGAC
 301 TTTTACAAGG TGCTCCGCCA GCGTGTCGTG GCGCGCCTCG AGGAGCGCAA
 351 GATCGCCCGC CGCGGCGGCC CCGAGATCTG GATCAAGGCC GCCATCCTCG
 401 TCAGCGGCTT CTGGTCCATG CTCTACCTCA TGTGCACCCT GGACCCGAAC
 451 CGCGGCGCCA TCCTGGCCGC CATCGCGCTG GGCATCGTCG CCGCCTTCGT
 501 CGGCACGTGC ATTCAGCACG ACGGCAACCA CGGCGCGTTC GCCTTCTCTC
 551 CGTTCATGAA CAAGCTCTCT GGCTGGACGC TCGACATGAT CGGCGCCAGT
 601 GCCATGACCT GGGAGATGCA GCACGTGCTG GCCACCACC CGTACACCAA
 651 CCTGATCGAG ATGGAGAACG GCACCCAAAA GGTCACCCAC GCCGACGTCG
 701 ACCCCAAGAA GGCCGACCAG GAGAGCGACC GGACGTCTT CAGCACCTAC
 751 CCCATGCTCC GTCTGCACCC GTGGCACCGC AAGCGCTTCT ACCACCGCTT
 801 CCAGCACCTG TACGCGCCGC TGCTCTTCGG TTTCATGACC ATCAACAAGG
 851 TGATCACCCA GGATGTGGGA GTTGTCCTCA GCAAGCGTCT GTTTCAGATC
 901 GATGCCAACT GCCGTTACGC CAGCAAGTCG TACGTTGCGC GCTTCTGGAT
 951 CATGAAGCTG CTCACCGTCC TCTACATGGT CGCCCTCCCC GTGTACACCC
1001 AGGGCCTTGT CGACGGGCTC AAGCTCTTCT TCATCGCCCA CTTTTCGTGC
1051 GGCGAGCTGC TGGCCACCAT GTTCATCGTC AACCACATCA TCGAGGGCGT
1101 CTCGTACGCC TCCAAGGACT CTGTCAAGGG CACCATGGCG CCGCCGCGCA
1151 CGGTGCACGG CGTGACCCCG ATGCATGACA CCCGCGACGC GCTCGGCAAG
1201 GAGAAGGCAG CCACCAAGCA CGTGCCGCTC AACGACTGGG CCGCGGTCCA
1251 GTGCCAGACC TCGGTCAACT GGTCGATCGG CTCGTGGTTC TGGAACCACT
1301 TCTCCGGCGG GCTCAACCAC CAGATCGAGC ACCACCTCTT CCCCGGCCTC
1351 ACCCACACCA CCTACGTGTA CATTCAGGAT GTGGTGCAGG CGACGTGCGC
1401 CGAGTACGGG GTCCCGTACC AGTCGGAGCA GAGCCTCTTC TCCGCCTACT
1451 TCAAGATGCT CTCCCACCTT CGGGCGCTCG GCAACGAGCC GATGCCCTCG
1501 TGGGAGAAGG ACCACCCCAA GTCCAAGTGA
```

FIG. 16

```
  1 MTVGGDEVYS MAQVRDHNTP DDAWCAIHGE VYELTKFART HPGGDIILLA
 51 AGKEATILFE TYHVRPISDA VLRKYRIGKL AAAGKDEPAN DSTYYSWDSD
101 FYKVLRQRVV ARLEERKIAR RGGPEIWIKA AILVSGFWSM LYLMCTLDPN
151 RGAILAAIAL GIVAAFVGTC IQHDGNHGAF AFSPFMNKLS GWTLDMIGAS
201 AMTWEMQHVL GHHPYTNLIE MENGTQKVTH ADVDPKKADQ ESDPDVFSTY
251 PMLRLHPWHR KRFYHRFQHL YAPLLFGFMT INKVITQDVG VVLSKRLFQI
301 DANCRYASKS YVARFWIMKL LTVLYMVALP VYTQGLVDGL KLFFIAHFSC
351 GELLATMFIV NHIIEGVSYA SKDSVKGTMA PPRTVHGVTP MHDTRDALGK
401 EKAATKHVPL NDWAAVQCQT SVNWSIGSWF WNHFSGGLNH QIEHHLFPGL
451 THTTYVYIQD VVQATCAEYG VPYQSEQSLF SAYFKMLSHL RALGNEPMPS
501 WEKDHPKSK
```

FIG.17

```
   1  ATGACGGCCG GATTTGAAGA AGTGATCACC ATGAAGCAGG TGAAGGACCG
  51  GAATACGCCG GACGATGCGT GGTGCGTGGT GCATGGCAAG GTGTACGACA
 101  TCACCAAGTT CAAGAACGCT CACCCCGGTG GAGATATAAT CATGTTGGCG
 151  GCTGGCAAGG ACGCCACCAT CCTGTTCGAG ACTTACCACA TCCGCGGTGT
 201  GCCCGATGCC GTGTTGCGCA AGTATCAGAT CGGCAAACTT CCGGACGGAA
 251  AGAACAAAGA GGGCGGCAAC GGCCTCGATA GCGCCTCGTA CTACTCCTGG
 301  GACAGCGAGT TTTACCGCGT CCTTCGCGAG CGCGTCTTGA AGCGCCTGAA
 351  CGAGCTCAAG CTGTCCAGAC GCGGAGGCTT CGAGATTTGG GCCAAGGCTA
 401  TCTTTCTCTT GACCGGCTTC TGGTCTTGCC TCTACCTCAT GTGCACACTC
 451  AACCCAAATG GGCTTGCGAT TCCTGCCGCC ATGATGTTGG GAATCTTTGC
 501  TGCCTTCGTA GGAACCTGCA TTCAGCACGA CGGGAATCAC GGTGCGTTCG
 551  CCCAATCTTC GTGGCTTAAC AAGGCCGCTG GTTGGACTTT GGACATGATT
 601  GGATCCAGCG CCATGACCTG GGAGATGCAG CACGTGCTTG ACATCATCC
 651  GTACACCAAC TTGATTGAAA TGGAGAATGG CAATCAAAAG GTCTCCGGCA
 701  AGCCTGTTGA CACCAAGACT GTCGACCAGG AGAGCGACCC TGATGTCTTT
 751  AGCACCTACC CTATGCTTCG CCTTCACCCT TGGCACAGCA AAAAGTGGTA
 801  CCACAAATAC CAGCACATCT ATGCACCATT CATCTTTGGG TTCATGACCA
 851  TCAACAAGGT CATTGCACAG GACGTTGGCG TTATCACACG CAAGCGTCTC
 901  TTCCAGATTG ACGCCAACTG CCGCTACGCT TCTCCGACTT ACGTCGCTCG
 951  CTTCTGGATC ATGAAGGTTC TTACCGTTCT CTACATGGTT GGCCTGCCAA
1001  TGTACATGCA AGGTCCATGG GAGGGTCTCA AGTTGTTCTT TATTGCGCAC
1051  TTTACTTGCG GCGAGCTGCT GGCCACAATG TTCATCGTAA ACCACATCAT
1101  CGAGGGTGTC AGCTACGCAA GCAAAGATGC CATCAAGGGC GAGATGGCTC
1151  CACCGAAAAC GGTCCGCGGT GTCACCCCAA TGCACGAGAC GCAAAAGGTT
1201  CTCGACCAGC GCGAGAAAGA CATGGACGAA ACTTCTAAGA AGAGCCGCAT
1251  CCCTCTCAAC GACTGGGCCG CTGTACAGTG CCAGACCACC GTGAACTGGG
1301  CTATCGGTTC TTGGTTCTGG AACCACTTTT CCGGGGGCCT CAATCATCAG
1351  ATTGAGCATC ATCTGTTCCC CGGCTTGACT CACACCACCT ATGTTCACTT
1401  TCACGATGTG GTCAAAGATA CTTGCGCTGA GTACGGGGTT CCATACCAGC
1451  ACGAGGAGAG TCTATACACT GCCTACTTTA AGATGTTGAA TCATCTCAAG
1501  ACCCTAGGCA ACGAGCCAAT GCCTGCCTGG GACAAGAACT AA
```

FIG.18

```
  1  MTAGFEEVIT  MKQVKDRNTP  DDAWCVVHGK  VYDITKFKNA  HPGGDIIMLA
 51  AGKDATILFE  TYHIRGVPDA  VLRKYQIGKL  PDGKNKEGGN  GLDSASYYSW
101  DSEFYRVLRE  RVLKRLNELK  LSRRGGFEIW  AKAIFLLTGF  WSCLYLMCTL
151  NPNGLAIPAA  MMLGIFAAFV  GTCIQHDGNH  GAFAQSSWLN  KAAGWTLDMI
201  GSSAMTWEMQ  HVLGHHPYTN  LIEMENGNQK  VSGKPVDTKT  VDQESDPDVF
251  STYPMLRLHP  WHSKKWYHKY  QHIYAPFIFG  FMTINKVIAQ  DVGVITRKRL
301  FQIDANCRYA  SPTYVARFWI  MKVLTVLYMV  GLPMYMQGPW  EGLKLFFIAH
351  FTCGELLATM  FIVNHIIEGV  SYASKDAIKG  EMAPPKTVRG  VTPMHETQKV
401  LDQREKDMDE  TSKKSRIPLN  DWAAVQCQTT  VNWAIGSWFW  NHFSGGLNHQ
451  IEHHLFPGLT  HTTYVHFHDV  VKDTCAEYGV  PYQHEESLYT  AYFKMLNHLK
501  TLGNEPMPAW  DKN
```

FIG.19

DNA sequence of the Delta 4 desaturase gene (pRIG6) from
Isochrysis galbana (CCMP 1323)

```
   1 ATGTGCAACG CGGCGCAGGT CGAGACGCAG GCCTTGCGCG CCAAGGAGGC
  51 GGCAAAACCG ACGTGGACGA AGATTCATGG GCGCACAGTC GACGTGGAGA
 101 CGTTCCGCCA CCCAGGCGGC AACATCCTCG ATTTGTTCCT GGGCATGGA
 151 GCCACAACTG CCTTTGAGAC GTTCCACGGT CACCACAAGG GAGCATGGAA
 201 GATGCTCAAG ACGCTGCCCG AGAAGGAGGT CGCCGCCGCC GACATTCCCG
 251 CGCAGAAGGA GGAGCACGTG GCCGAGATGA CACGCCTCAT GGCCTCATGG
 301 CGCGAGCGCG GGCTGTTCAA GCCGCGTCCC GTCGCCTCAT CCATCTATGG
 351 CCTGTGCGTG ATCTTCGCCA TCGCGGCATC GGTCGCGTGC GCTCCGTACG
 401 CGCCAGTGCT GGCTGGCATC GCGGTGGGCA CCTGCTGGGC TCAGTGCGGC
 451 TTCTTGCAGC ACATGGGCGG CCACGGGAG TGGGGGCGCA CTTGGTCGTT
 501 TGCGTTTCAG CATCTGTTTG AAGGCCTGCT CAAGGGCGGC TCGGCCTCGT
 551 GGTGGCGCAA CCGCCACAAC AAGCACCATG CCAAGACCAA CGTGCTCGGC
 601 GAGGACGGCG ACCTGCGCAC CACACCCTTC TTCGCATGGG ACCCTACTCT
 651 GGCCAAGAAA GTGCCCGACT GGTCTCTGCG CACGCAAGCC TTCACCTTTC
 701 TGCCAGCACT GGGAGCTTAC GTCTTCGTCT TGCCTTCAC GGTACGCAAG
 751 TACAGTGTGG TGAAGCGTCT CTGGCACGAG GTCGCCCTGA TGGTGGCCCA
 801 CTACGCTCTC TTTTCCTGGG CGCTCAGCGC CGCCGGCGCC TCCCTCAGCT
 851 CCGGCCTCAC CTTCTATTGC ACCGGGTACG CCTGGCAGGG CATCTACCTC
 901 GGCTTCTTCT TCGGCCTATC GCACTTTGCG GTGGAGCGCG TGCCGTCGAC
 951 CGCCACCTGG CTCGAGTCGA CGATGATGGG CACCGTTGAC TGGGGCGGCT
1001 CCTCCGCCTT CTGCGGCTAC CTCTCCGGCT TCCTCAATAT CCAGATCGAG
1051 CACCACATGG CTCCACAAAT GCCAATGGAG AACCTGCGCC AGATCCGGGC
1101 CGACTGCAAG GCCGCGGCCC ACAAGTTCGG GCTGCCGTAC CGCGAGCTGA
1151 CATTCGTCGC GGCGACCAAG CTCATGATGA GCGGCCTCTA CCGGACCGGC
1201 AAGGACGAGC TCAAGCTGCG CGCGGACCGC CGCAAGTTCA CGAGGGCACA
1251 GGCGTACATG GGCGCCGCCA GCGCTTTGGT CGACACGCTC AAGGCGGACT
1301 AA
```

FIG. 20

Amino acid sequence of the Delta 4 desaturase gene (pRIG6)
from Isochrysis galbana (CCMP 1323)

```
  1  MCNAAQVETQ ALRAKEAAKP TWTKIHGRTV DVETFRHPGG NILDLFLGMD

51  ATTAFETFHG HHKGAWKMLK TLPEKEVAAA DIPAQKEEHV AEMTRLMASW

101  RERGLFKPRP VASSIYGLCV IFAIAASVAC APYAPVLAGI AVGTCWAQCG

151  FLQHMGGHRE WGRTWSFAFQ HLFEGLLKGG SASWWRNRHN KHHAKTNVLG

201  EDGDLRTTPF FAWDPTLAKK VPDWSLRTQA FTFLPALGAY VFVFAFTVRK

251  YSVVKRLWHE VALMVAHYAL FSWALSAAGA SLSSGLTFYC TGYAWQGIYL

301  GFFFGLSHFA VERVPSTATW LESTMMGTVD WGGSSAFCGY LSGFLNIQIE

351  HHMAPQMPME NLRQIRADCK AAAHKFGLPY RELTFVAATK LMMSGLYRTG

401  KDELKLRADR RKFTRAQAYM GAASALVDTL KAD*
```

FIG.21

Comparative analysis of the Delta 4 desaturase from
I. galbana (CCMP 1323) (pRIG6.pep) and the Delta 4 desaturase
from T. aureum (ATCC 34304)(pRTA7.pep)

Quality:       68
Ratio:         0.157
Percent Similarity: 38.384

Length:        554
Gaps:          22
Percent Identity: 30.808

Match display thresholds for the alignment(s):
| = IDENTITY
: = 2
. = 1 pRIG6.pepx prta7.pep

```
  1 ..MCNAAQVETQALRAKEAAKPTWTKIHGRTVDVETFR..HPGGNILDLF  46
      .  |    .|      |  |||   |:  |  ||||.|:  |
  1 MTVGFDETVTMDTVRNHNMPDDAWCAIHGTVYDITKFSKVHPGGDIIMLA  50

47 LGMDATTAFETFH..GHHKGAWKMLKT..LPE.KEVAAADIPAQKE....  87
    | :||  |||:|    |    :  |    ||: |.  . .|     :
 51 AGKEATILFETYHIKGVPDAVLRKYKVGKLPQGKKGETSHMPTGLDSASY 100

88 ...........EHVAE.......MTRLMASWRERGLFKPRPVASSIYGL 118
               | ||.         ||      : :|         |:| :
101 YSWDSEFYRVLRERVAKKLAEPGLMQRARMELWAKAIFLLAGFWGSLYAM 150

119 CVIFAIAASVACAPYAPVLAGIAVGTCWAQCGFLQHMGGHREWGRTWSFA 168
    ||:       .. |   | | ||||          :|| | |  . :.
151 CVLDPHGGAMVAAVTLGVFAAF.VGTC.......IQHDGSHGAFSKS...R 190

169 FQHLFEGL...LKGGSASWWRNRH.NKHHAKTNVLGEDGDLRTTPFFAWD 214
    | .    |  : | ||| |  .|   ||  ||.:  :   |        |
191 FMNKAAGWTLDMIGASAMTWEMQHVLGHHPYTNLIEMENGLAKVKGADVD 240

215 PTLAKKVPDWSLRTQAFTFLPALGAYVF................VFAF.T 247
    |  ||| |      |. | |  : .                   :| | |
241 P...KKV.DQESDPDVFSTYPMLRLHPWHRQRFYHKFQHLYAPLIFGFMT 286

248 VRK.....YSVV..KRL...........WHEVA..LMVAHYALFSWALS 276
    : |       || |||           |.    :|   |:  ||
287 INKVISQDVGVVLRKRLFQIDANCRYGSPWNVARFWIMKLLTTLYMVALP 336

277 AAGASLSSGLTFYCTGYAWQGIYLGFFFGLSHF................ 309
       .||   :  :   |  |    |..|
337 MYMQGPAQGLKLFFMAHFTCGEVLATMFIVNHIIEGVSYASKDAVKGVMA 386
```

FIG.22A

```
310 ....................AVERVPSTA..........TWLESTMMGTVDW 331
                       | |  | |             |     .|.|
387 PPRTVHGVTPMQVTQKALSAAESTKSDADKTTMIPLNDWAAVQCQTSVNW 436

332 GGSSAFCGYLSGFLNIQIEHHMAPQMPMENLRQIRADCKAAAHKFGLPYR 381
    | |  : || || ||||| || |      |    |    .:|.||.
437 AVGSWFWNHFSGGLNHQIEHHCFPQNPHTVNVYISGIVKETCEEYGVPYQ 486

382 .ELTFVAATKLMMSGLYRTGKDELKLRADRRKFTRAQAYMGAASALVDTL 430
     |:.  .|   |:| |    | ::|    .
487 AEISLFSAYFKMLSHLRTLGNEDLTAWST*.................... 516
```

FIG.22B

Δ4-DESATURASE GENES AND USES THEREOF

The subject application is a divisional of U.S. patent application Ser. No. 10/120,637, filed on Apr. 11, 2002 now U.S. Pat. No. 7,045,683, which is hereby incorporated in its entirety by reference.

The subject application is a continuation-in-part of U.S. patent application Ser. No. 09/849,199, filed on May 4, 2001 now abandoned, hereby incorporated in its entirety by reference.

BACKGROUND OF THE INVENTION

1. Technical Field

The subject invention relates to the identification and isolation of genes that encode enzymes (e.g., *Thraustochytrium aureum* Δ4-desaturase, *Schizochytrium aggregatum* Δ4-desaturase and *Isochrysis galbana* Δ4-desaturase) involved in the synthesis of polyunsaturated fatty acids and to uses thereof. In particular, Δ4-desaturase catalyzes the conversion of, for example, adrenic acid (22:4n-6) to ω6-docosapentaenoic acid (22:5n-6) and the conversion of ω3-docosapentaenoic acid (22:5n-3) to docosahexaenoic acid (22:6n-3). The converted products may then be utilized as substrates in the production of other polyunsaturated fatty acids (PUFAs). The product or other polyunsaturated fatty acids may be added to pharmaceutical compositions, nutritional composition, animal feeds as well as other products such as cosmetics.

2. Background Information

Desaturases are critical in the production of long-chain polyunsaturated fatty acids that have many important functions. For example, polyunsaturated fatty acids (PUFAs) are important components of the plasma membrane of a cell, where they are found in the form of phospholipids. They also serve as precursors to mammalian prostacyclins, eicosanoids, leukotrienes and prostaglandins.

Additionally, PUFAs are necessary for the proper development of the developing infant brain as well as for tissue formation and repair. In view of the biological significance of PUFAs, attempts are being made to produce them, as well as intermediates leading to their production, in an efficient manner.

A number of enzymes, most notably desaturase and elongases, are involved in PUFA biosynthesis (see FIG. 1). For example, elongase (elo) catalyzes the conversion of γ-linolenic acid (GLA) to dihomo-γ-linolenic acid (DGLA) and of stearidonic acid (18:4n-3) to (n-3)-eicosatetraenoic acid (20:4n-3). Linoleic acid (LA, 18:2n-9,12 or 18:2n-6) is produced from oleic acid (18:1-Δ9) by a Δ12-desaturase. GLA (18:3n-6,9,12) is produced from linoleic acid by a Δ6-desaturase.

It must be noted that animals cannot desaturate beyond the Δ9 position and therefore cannot convert oleic acid into linoleic acid. Likewise, γ-linolenic acid (ALA, 18:3n-9,12, 15) cannot be synthesized by mammals. However, γ-linolenic acid can be converted to stearidonic acid (STA, 18:4n-6,9,12,15) by a Δ6-desaturase (see PCT publication WO 96/13591 and *The FASEB Journal*, Abstracts, Part I, Abstract 3093, page A532 (Experimental Biology 98, San Francisco, Calif., Apr. 18–22, 1998); see also U.S. Pat. No. 5,552,306), followed by elongation to (n-3)-eicosatetraenoic acid (20: 4n-8,11,14,17) in mammals and algae. This polyunsaturated fatty acid (i.e., 20:4n-8,11,14,17) can then be converted to eicosapentaenoic acid (EPA, 20:5n-5,8,11,14,17) by a Δ5-desaturase. EPA can then, in turn, be converted to ω3-docosapentaenoic acid (22:5n-3) by an elongase. Isolation of an enzyme or its encoding gene, responsible for conversion of ω3-docosapentaenoic acid to docosahexaenoic acid (22:6n-3) has never been reported. Two pathways for this conversion have been proposed (see FIG. 1 and Sprecher, H., *Curr. Opin. Clin. Nutr. Metab. Care*, Vol.2, p. 135–138, 1999). One of them involves a single enzyme, a Δ4-desaturase such as that of the present invention. In the n-6 pathway, dietary linoleic acid may be converted to adrenic acid through a series of desaturation and elongation steps in mammals (see FIG. 1). Production of ω6-docosapentaenoic acid from adrenic acid is postulated to be mediated by the Δ6-desaturase discussed above.

Other eukaryotes, including fungi and plants, have enzymes which desaturate at carbon 12 (see PCT publication WO 94/11516 and U.S. Pat. No. 5,443,974) and carbon 15 (see PCT publication WO 93/11245). The major polyunsaturated fatty acids of animals therefore are either derived from diet and/or from desaturation and elongation of linoleic acid or γ-linolenic acid. In view of these difficulties, it is of significant interest to isolate genes involved in PUFA synthesis from species that naturally produce these fatty acids and to express these genes in a microbial, plant, or animal system which can be altered to provide production of commercial quantities of one or more PUFAs.

In view of the above discussion, there is a definite need for the Δ4-desaturase enzyme, the respective genes encoding this enzyme, as well as recombinant methods of producing this enzyme. Additionally, a need exists for oils containing levels of PUFAs beyond those naturally present as well as those enriched in novel PUFAs. Such oils can only be made by isolation and expression of the Δ4-desaturase gene(s).

All U.S. patents and publications referred to herein are hereby incorporated in their entirety by reference.

The present invention includes an isolated nucleotide sequence or fragment thereof comprising or complementary to a nucleotide sequence encoding a polypeptide having desaturase activity. The amino acid sequence of the polypeptide has at least 50% sequence identity to an amino acid sequence selected from the group consisting of SEQ ID NO:18, SEQ ID NO:19, SEQ ID NO:20, SEQ ID NO:21, SEQ ID NO:37, SEQ ID NO:46 and SEQ ID NO:55. Also, in particular, the present invention encompasses an isolated nucleotide sequence or fragment thereof comprising or complementary to a nucleotide sequence encoding a polypeptide having desaturase activity, wherein the amino acid sequence of said polypeptide has at least 30% identity to the amino acid sequence of SEQ ID NO:55.

Additionally, the present invention encompasses an isolated nucleotide sequence or fragment thereof comprising or complementary to a nucleotide sequence having at least 50% sequence identity to a nucleotide sequence selected from the group consisting of SEQ ID NO:14, SEQ ID NO:15 and SEQ ID NO:16, SEQ ID NO:17, SEQ ID NO:36, SEQ ID NO:45 and SEQ ID NO:54. In particular, the present invention includes an isolated nucleotide sequence or fragment thereof comprising or complementary to a nucleotide sequence having at least 40% identity to the nucleotide sequence of SEQ ID NO:54.

Each of the sequences described above encodes a functionally active desaturase that utilizes a monounsaturated or polyunsaturated fatty acid as a substrate. The nucleotide sequences may be derived for example, from a fungus or an algae. In particular, when the nucleotide sequence comprises SEQ ID NO:14, SEQ ID NO:15, SEQ ID NO:16, SEQ ID NO:17 or SEQ ID NO:45, may be derived, for example, from the fungus *Thraustochytrium aureum*. The sequence comprising SEQ ID NO:36 may be derived, for example, from the fungus *Schizochytrium aggregatum*. The sequence comprising SEQ ID NO:54 may be derived, for example, from the algae *Isochrysis galbana*. The present invention also includes purified protein and fragments thereof encoded by the above-referenced nucleotide sequences.

In particular, the present invention also includes a purified polypeptide which desaturates polyunsaturated fatty acids at carbon 4 and has an amino acid sequence having at least 50% identity to an amino acid sequence selected from the group consisting of SEQ ID NO:18, SEQ ID NO:19, SEQ ID NO:20, SEQ ID NO:21, SEQ ID NO:37, SEQ ID NO:46 and SEQ ID NO:55. In particular, the present invention also includes a purified polypeptide which desaturates polyunsaturated fatty acids at carbon 4 and has an amino acid sequence having at least 30% identity to the amino acid sequence of SEQ ID NO:55.

Additionally, the present invention includes a method of producing a desaturase comprising the steps of: isolating a nucleotide sequence comprising or complementary to a nucleotide sequence encoding a polypeptide having an amino acid sequence having at least 50% identity to an amino acid sequence selected from the group consisting of SEQ ID NO:18, SEQ ID NO:19, SEQ ID NO:20, SEQ ID NO:21, SEQ ID NO:37, SEQ ID NO:46 and SEQ ID NO:55 (or at least 30% identity to the amino acid sequence of SEQ ID NO:55) or having at least 50% sequence identity to a nucleotide sequence selected from the group consisting of SEQ ID NO: 14, SEQ ID NO:15, SEQ ID NO:16, SEQ ID NO:17, SEQ ID NO:36, SEQ ID NO:45 and SEQ ID NO:54 (or having, in particular, at least 40% sequence identity to SEQ ID NO:54); constructing a vector comprising: i) the isolated nucleotide sequence operably linked to ii) a promoter; and introducing said vector into a host cell for a time and under conditions sufficient for expression of the desaturase. The host cell may be, for example, a eukaryotic cell or a prokaryotic cell. In particular, the prokaryotic cell may be, for example, *E. coli*, cyanobacteria or *B. subtilis*. The eukaryotic cell may be, for example, a mammalian cell, an insect cell, a plant cell or a fungal cell (e.g., a yeast cell such as *Saccharomyces cerevisiae, Saccharomyces carlsberuensis, Candida spp., Lipomyces starkey, Yarrowia lipolytica, Kluyveromyces spp., Hansenula spp., Trichoderma spp.* or *Pichia spp.*).

Moreover, the present invention also includes a vector comprising: an isolated nucleotide sequence comprising or complementary to a nucleotide sequence encoding a polypeptide having an amino acid sequence having at least 50% amino acid identity to an amino acid sequence selected from the group consisting of SEQ ID NO: 18, SEQ ID NO:19, SEQ ID NO:20, SEQ ID NO:21, SEQ ID NO:37, SEQ ID NO:46 and SEQ ID NO:55 (or, in particular, at least 30% amino acid identity to SEQ ID NO:55) or having at least 50% sequence identity to a nucleotide sequence selected from the group consisting of SEQ ID NO:14, SEQ ID NO:15, SEQ ID NO:16, SEQ ID NO:17, SEQ ID NO:36, SEQ ID NO:45 and SEQ ID NO:54 (or, in particular, at least 40% identity to SEQ ID NO:54), operably linked to a promoter. The invention also includes a host cell comprising this vector. The host cell may be, for example, a eukaryotic cell or a prokaryotic cell. Suitable eukaryotic cells and prokaryotic cells are as defined above.

Moreover, the present invention also includes a plant cell, plant or plant tissue comprising the above vector, wherein expression of the nucleotide sequence of the vector results in production of a polyunsaturated fatty acid by the plant cell, plant or plant tissue. The polyunsaturated fatty acid may be, for example, selected from the group consisting of ω6-docosapentaenoic acid or docosahexaenoic acid. The invention also includes one or more plant oils or acids expressed by the above plant cell, plant or plant tissue.

Additionally, the present invention also encompasses a transgenic plant comprising the above vector, wherein expression of the nucleotide sequence of the vector results in production of a polyunsaturated fatty acid in seeds of the transgenic plant.

The present invention also includes a method ("first method") for producing a polyunsaturated fatty acid comprising the steps of: isolating a nucleotide sequence comprising or complementary to a nucleotide sequence encoding a polypeptide having an amino acid sequence having at least 50% amino acid sequence identity to an amino acid sequence selected from the group consisting of SEQ ID NO: 18, SEQ ID NO: 19, SEQ ID NO:20, SEQ ID NO:21, SEQ ID NO:37, SEQ ID NO:46 and SEQ ID NO:55 (and, in particular, at least 30% amino acid sequence identity to SEQ ID NO:55) or having at least 50% sequence identity to a nucleotide sequence selected from the group consisting of SEQ ID NO:14, SEQ ID NO:15, SEQ ID NO:16 and SEQ ID NO:17, SEQ ID NO:36, SEQ ID NO:45, and SEQ ID NO:54 (and, in particular, at least 40% with respect to SEQ ID NO:54); constructing a vector comprising the isolated nucleotide sequence; introducing the vector into a host cell for a time and under conditions sufficient for expression of Δ4-desaturase; and exposing the expressed Δ4-desaturase to a substrate polyunsaturated fatty acid in order to convert the substrate to a product polyunsaturated fatty acid. The substrate polyunsaturated fatty acid may be, for example, adrenic acid or ω3-docospentaenoic acid, and the product polyunsaturated fatty acid may be, for example, ω6-docosapentaenoic acid or docosahexaenoic acid, respectively. This method may further comprise the step of exposing the product polyunsaturated fatty acid to another enzyme (e.g., a Δ4-desaturase, an elongase or another desaturase) in order to convert the product polyunsaturated fatty acid to another polyunsaturated fatty acid (i.e., "second" method). In this method containing the additional step (i.e., "second" method), the product polyunsaturated fatty acid may be, for example, ω6-docosapentaenoic acid, and the "another" polyunsaturated fatty acid may be docosahexaenoic acid.

Also, the present invention includes a method of producing a polyunsaturated fatty acid comprising the steps of: exposing a substrate polyunsaturated fatty acid to one or more enzymes selected from the group consisting of a desaturase and an elongase in order to convert the substrate to a product polyunsaturated fatty acid; and exposing the product polyunsaturated fatty acid to a Δ4-desaturase comprising an amino acid sequence selected from the group consisting of SEQ ID NO: 18, SEQ ID NO: 19, SEQ ID NO:20, SEQ ID NO:21, SEQ ID NO:37, SEQ ID NO:46 and SEQ ID NO:55, in order to convert the product polyunsaturated fatty acid to a final product polyunsaturated fatty acid.

For example, a substrate polyunsaturated fatty acid (e.g., eicosapentaenoic acid) may be exposed to an elongase or desaturase (e.g., MELO4 or other elongases or desaturases of significance in the biosynthetic pathway) in order to convert the substrate to a product polyunsaturated fatty acid (e.g., ω3-docosapentaenoic acid). The product polyunsaturated fatty acid may then be converted to a "final" product polyunsaturated fatty acid (e.g., docosahexaenoic acid) by exposure to the Δ4-desaturase of the present invention (see FIG. 1). Thus, the Δ4-desaturase is utilized in the last step of the method in order to create the "final" desired product. As another example, one may expose linoleic acid to a Δ6-desaturase in order to create γ-linolenic acid (GLA), and then expose the GLA to an elongase and then to a Δ5-desaturase in order to create arachidonic acid (AA). The AA may then be exposed to an elongase in order to convert it to adrenic acid. Finally, the adrenic acid may be exposed to Δ4-desaturase in order to convert it to ω6-docosapentaenoic acid (see FIG. 1). Thus, the method involves the utilization of a linoleic acid substrate and a series of desaturase and elongase enzymes, in addition to the Δ4-desaturase, in order to arrive at the final product. By use of a similar method, one may also convert the substrate PUFA, γ-linolenic acid to docosoahexaenoic acid. Again, various desaturases and elongase are used to ultimately arrive at ω3-docosapentaenoic acid which is then exposed to one or more of the Δ4-desaturases of the present invention in order to convert it to docosahexaenoic acid. (Possible substrates include those shown in FIG. 1, for example, linoleic acid, γ-linolenic acid, stearidonic acid, arachidonic acid, dihomo-γ-linolenic acid, adrenic acid, eicosapentaenoic acid and eicosatetraenoic acid.)

The present invention also encompasses a composition comprising at least one polyunsaturated fatty acid selected from the group consisting of the "product" polyunsaturated fatty acid produced according to the methods described above and the "another" polyunsaturated fatty acid produced according to the methods described above. The product polyunsaturated fatty acid may be, for example, ω6-docosapentaenoic acid or docosahexaenoic acid. The another polyunsaturated fatty acid may be, for example, docosahexaenoic acid.

Additionally, the present invention encompasses a method of preventing or treating a condition caused by insufficient intake of polyunsaturated fatty acids comprising administering to the patient the composition above in an amount sufficient to effect prevention or treatment.

BRIEF DESCRIPTION OF THE DRAWINGS

FIG. 2 illustrates an amino acid comparison of Δ4-desaturases produced by four different plasmids (SEQ ID NO:18, SEQ ID NO:19, SEQ ID NO:20 and SEQ ID NO:21).

FIG. 3 illustrates the nucleotide sequence encoding Δ4-desaturase of *Thraustochytrium aureum* (ATCC 34304) from plasmid pRTA5 (SEQ ID NO:14).

FIG. 4 illustrates the nucleotide sequence encoding Δ4-desaturase of *Thraustochytrium aureum* (ATCC 34304) from plasmid pRTA6 (SEQ ID NO:15).

FIG. 5 illustrates the nucleotide sequence encoding Δ4-desaturase of *Thraustochytrium aureum* (ATCC 34304) from plasmid pRTA7 (SEQ ID NO:16).

FIG. 6 illustrates the nucleotide sequence encoding encoding Δ4-desaturase of *Thraustochytrium aureum* (ATCC 34304) from plasmid pRTA8 (SEQ ID NO:17).

FIG. 7 illustrates the amino acid sequence of Δ4-desaturase of *Thraustochytrium aureum* (ATCC 34304) from plasmid pRTA5 (SEQ ID NO:18).

FIG. 8 illustrates the amino acid sequence of Δ4-desaturase of *Thraustochytrium aureum* (ATCC 34304) from plasmid pRTA6 (SEQ ID NO:19).

FIG. 9 illustrates the amino acid sequence of Δ4-desaturase of *Thraustochytrium aureum* (ATCC 34304) from plasmid pRTA7 (SEQ ID NO:20).

FIG. 10 illustrates the amino acid sequence of Δ4-desaturase of *Thraustochytrium aureum* (ATCC 34304) from plasmid pRTA8 (SEQ ID NO:21).

FIG. 11 illustrates the nucleotide and amino acid sequences described herein.

FIG. 12 illustrates the amino acid sequence encoded by the elongase gene MELO4 from a mouse.

FIG. 13 illustrates the DNA sequence of the putative Δ4-desaturase ssa.con (SEQ ID NO:24) generated from clones saa9 and saa5 from *S. aggregatum* (ATCC 28209) (see Example VI).

FIG. 14 illustrates the amino acid sequence (SEQ ID NO:25) of the putative Δ4-desaturase encoded by the ssa.con DNA sequence from *S. aggregatum* (ATCC 28209) (see Example VI).

FIG. 15 illustrates the alignment of the amino acids derived from the translation of the open reading frames of ssa.con DNA from *S. aggregatum* (ATCC 28209) (SEQ ID NO:25) and pRTA7 (SEQ ID NO:68) (see Example VI).

FIG. 16 illustrates the DNA sequence of the Δ4-desaturase from pRSA1 (SEQ ID NO:36) *S. aggregatum* (ATCC 28209) (see Example VII).

FIG. 17 illustrates the amino acid sequence (SEQ ID NO:37) of the Δ4-desaturase encoded by the pRSA1 DNA sequence from *S. aggregaium* (ATCC 28209) (see Example VII).

FIG. 18 illustrates the DNA sequence of the Δ4-desaturase from pRTA11 (SEQ ID NO:45) *T. aureum* (BICC 7091) (see Example VII).

FIG. 19 illustrates the amino acid sequence (SEQ ID NO:46) of the putative Δ4-desaturase encoded by the pRTA11 DNA sequence from *T. aureum* (BICC 7091) (see Example VII).

FIG. 20 illustrates the DNA sequence of the Δ4-desaturase from *Isochrysis galbana* (CCMP1323)(SEQ ID NO:54) present in clone pRIG6 (see Example IX).

FIG. 21 illustrates the amino acid sequence (SEQ ID NO:55) of the Δ4-desaturase encoded by the pRIG6 DNA sequence from *Isochrysis galbana* (CCMP 1323) (see Example IX).

FIG. 22 illustrates the percent identity between the novel Δ4-desaturase from *I. galbana* (CCMP 1323) (SEQ ID NO:69) and the Δ4-desaturase from *Thraustochytrium aureum* (ATCC 34304) (SEQ ID NO:70).

DETAILED DESCRIPTION OF THE INVENTION

Figure 1:
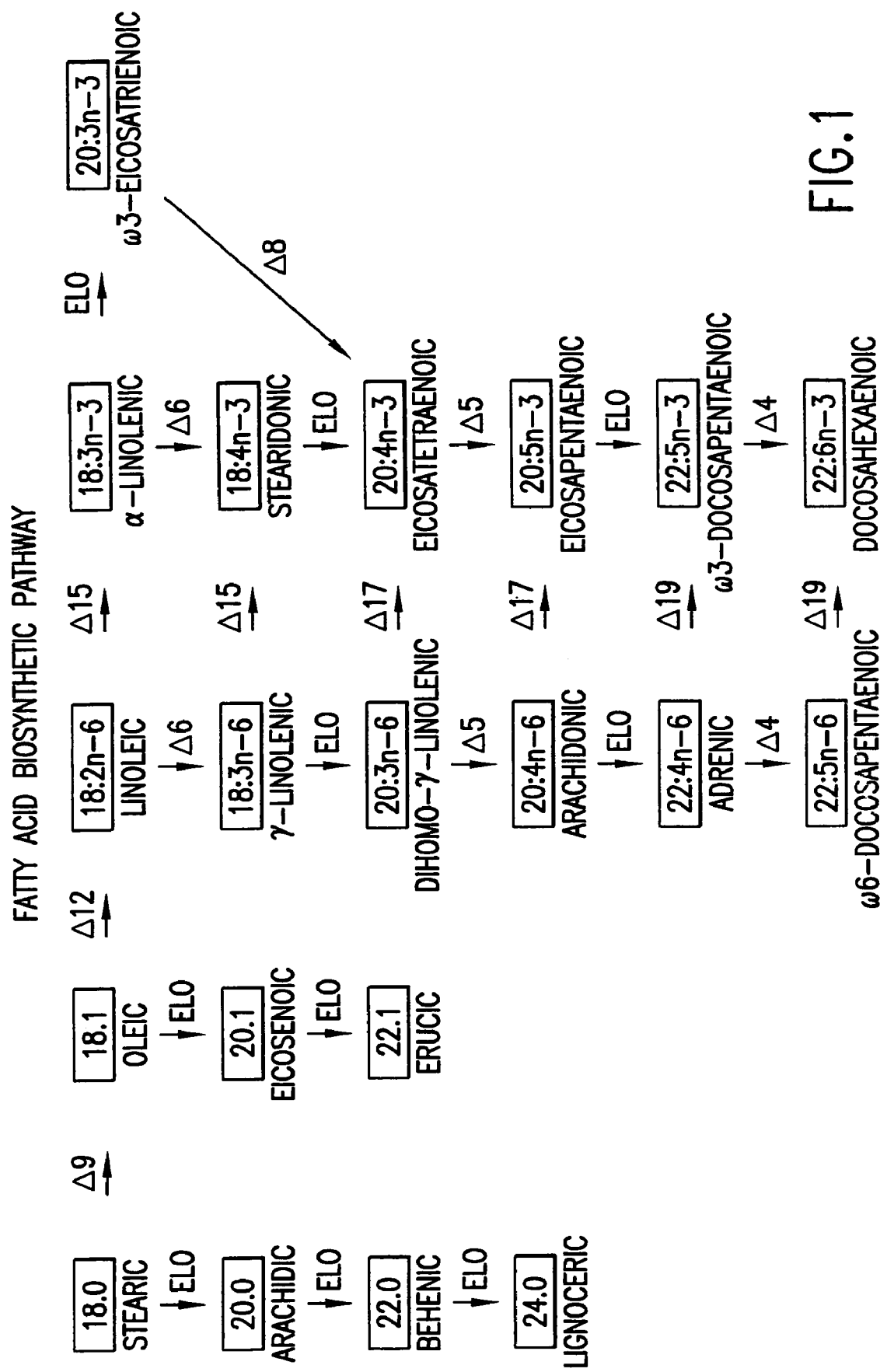
FIG. 1 illustrates the fatty acid biosynthetic pathway and the role of Δ4-desaturase in this pathway.

The subject invention relates to the nucleotide and translated amino acid sequences of the Δ4-desaturase gene derived from the fungus *Thraustochytrium aureum* (BICC 7091), the fungus *Schizochytrium aggregatum*, and the algae *Isochrysis galbana*. Furthermore, the subject invention also includes uses of these genes and of the enzymes encoded by these genes. For example, the genes and corresponding enzymes may be used in the production of polyunsaturated fatty acids such as, for instance, ω6-docosapentaenoic acid and/or docosahexaenoic acid which may be added to pharmaceutical compositions, nutritional compositions and to other valuable products.

The Δ4-Desaturase Genes and Enzymes Encoded Thereby

As noted above, the enzymes encoded by the Δ4-desaturase genes of the present invention are essential in the production of highly unsaturated polyunsaturated fatty acids having a length greater than 22 carbons. The nucleotide sequences of the isolated *Thraustochytrium aureum* Δ4-desaturase genes, which differed based upon the plasmid created (see Example III), are shown in FIGS. 3–6, and the amino acid sequences of the corresponding purified proteins are shown in FIG. 7–10. An additional, isolated *T. aureum* nucleotide sequence is shown in FIG. 18 (see Example VII), and the encoded amino acid sequence is shown in FIG. 19. The nucleotide sequences of the isolated *Schizochytrium aggregatum* Δ4-desaturase sequences are shown in FIGS. 13 and 16, and the encoded amino acid sequences are shown in FIGS. 14 and 17, respectively. Additionally, the nucleotide sequences of the isolated *Isochrysis galbana* Δ4-desaturase sequence is shown in FIG. 20, and the amino acid sequence encoded by the nucleotide sequence is shown in FIG. 21.

As an example of the importance of the genes of the present invention, the isolated Δ4-desaturase genes convert adrenic acid to ω6-docosapentaenoic acid or convert ω3-docosapentaenoic acid to docosahexaenoic acid.

It should be noted that the present invention also encompasses isolated nucleotide sequences (and the corresponding encoded proteins) having sequences comprising, corresponding to, identical to, or complementary to at least about 50%, preferably at least about 60%, and more preferably at least about 70%, even more preferably at least about 80%, and most preferably at least about 90% sequence identity to SEQ ID NO:14, SEQ ID NO:15, SEQ ID NO:16 or SEQ ID NO:17 (i.e., the nucleotide sequences of the Δ4-desaturase gene of *Thraustochytrium aureum* (ATCC 34304)), to SEQ ID NO:36 (i.e., the nucleotide sequence of the Δ4-desaturase gene of *Schizochytrium aggregatum* (ATCC 28209) or to SEQ ID NO:45 (i.e., the nucleotide sequence of the Δ4-desaturase gene of *Thraustochytrium aureum* (BICC 7091)) or to SEQ ID NO:54 (i.e., the nucleotide sequence of the Δ4-desaturase gene of *Isochrysis galabana*), all described herein. With respect to the *I. galbana* sequence, in particular, the present invention also encompasses nucleotide sequences (and the corresponding encoded proteins) having sequences comprising, corresponding to, identical to, or complementary to at least 40%, more preferably at least 60%, even more preferably at least 80%, and most preferably at least 90% of the nucleotide sequence of SEQ ID NO:54. (All integers between 40% and 100% are also considered to be within the scope of the present invention with respect to percent identity.) Such sequences may be derived from any source, either isolated from a natural source, or produced via a semi-synthetic route, or synthesized de novo. In particular, such sequences may be isolated or derived from sources other than described in the examples (e.g., bacteria, fungus, algae, *C. elegans*, mouse or human).

Furthermore, the present invention also encompasses fragments and derivatives of the nucleotide sequences of the present invention (i.e., SEQ ID NO:14, SEQ ID NO:15, SEQ ID NO:16, SEQ ID NO:17, SEQ ID NO:36, SEQ ID NO:45 or SEQ ID NO:54), as well as of the sequences derived from other sources, and having the above-described complementarity, identity or correspondence. Functional equivalents of the above full length sequences and fragments (i.e., sequences having Δ4-desaturase activity, as appropriate) are also encompassed by the present invention.

For purposes of the present invention, a "fragment" is of a nucleotide sequence is defined as a contiguous sequence of approximately at least 6, preferably at least about 8, more preferably at least about 10 nucleotides, and even more preferably at least about 15 nucleotides corresponding to a region of the specified nucleotide sequence.

The invention also includes a purified polypeptide which desaturates polyunsaturated fatty acids at the carbon 4 position and has at least about 50% amino acid similarity or identity, preferably at least about 60% amino acid similarity or identity, more preferably at least about 70% amino acid similarity or identity, even more preferably at least about 80% amino acid similarity or identity and most preferably at least 90% amino acid similarity or identity to the amino acid sequences (i.e., SEQ ID NO:18 (shown in FIG. 7), SEQ ID NO:19 (shown in FIG. 8), SEQ ID NO:20 (shown in FIG. 9), SEQ ID NO:21 (shown in FIG. 10), SEQ ID NO:37 (shown in FIG. 17), SEQ ID NO:46 (shown in FIG. 19) and SEQ ID NO:55 (shown in FIG. 21) of the above-noted proteins which are, in turn, encoded by the above-described nucleotide sequences. In particular, with respect to the amino acid sequence of the *I. galbana* Δ4-desaturase, the present invention encompasses includes a purified polypeptide which desaturates polyunsaturated fatty acids at the carbon 4 position and has at least about 30% amino acid similarity or identity, preferably at least about 50% amino acid similarity or identity, more preferably at least about 70% amino acid similarity or identity and most preferably at least about 90% amino acid similarity or identity to the amino acid sequence of SEQ ID NO:55 (i.e., the amino acid sequence of the *I. galbana* Δ4-desaturase shown in FIG. 21). (All integers between 30% and 100% similarity or identity are also included within the scope of the present invention.)

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Clustal Macaw Pileup Higgins et al., CABIOS. 5L151–153 (1989)), FASTDB (Intelligenetics), BLAST (National Center for Biomedical Information; Altschul et al., Nucleic Acids Research 25:3389–3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

For purposes of the present invention, "complementarity is defined as the degree of relatedness between two DNA segments. It is determined by measuring the ability of the sense strand of one DNA segment to hybridize with the antisense strand of the other DNA segment, under appropriate conditions, to form a double helix. A "complement" is defined as a sequence which pairs to a given sequence based upon the canonic base-pairing rules. For example, a sequence A-G-T in one nucleotide strand is "complementary" to T-C-A in the other strand.

In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity between two amino acid sequences is defined as the presence of a series of exactly alike or invariant amino acid residues in both sequences.) The definitions of "complementarity", "identity" and "similarity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

The present invention also encompasses an isolated nucleotide sequence which encodes PUFA desaturase activity and that is hybridizable, under moderately stringent conditions, to a nucleic acid having a nucleotide sequence comprising or complementary to the nucleotide sequences described above. A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

As used herein, an "isolated nucleic acid fragment or sequence" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (A "fragment" of a specified polynucleotide refers to a polynucleotide sequence which comprises a contiguous sequence of approximately at least about 6 nucleotides, preferably at least about 8 nucleotides, more preferably at least about 10 nucleotides, and even more preferably at least about 15 nucleotides, and most preferable at least about 25 nucleotides identical or complementary to a region of the specified nucleotide sequence.) Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "fragment or subfragment that is functionally equivalent" and "functionally equivalent fragment or subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric constructs to produce the desired phenotype in a transformed plant. Chimeric constructs can be designed for use in co-suppression or antisense by linking a nucleic acid fragment or subfragment thereof, whether or not it encodes an active enzyme, in the appropriate orientation relative to a plant promoter sequence.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

"Gene" refers to a nucleic acid fragment that expresses a specific protein, including regulatory sequences preceding (5' non-coding sequences) and following (3' non-coding sequences) the coding sequence.

"Native gene" refers to a gene as found in nature with its own regulatory sequences. In contrast, "chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term "isolated" means that the sequence is removed from its natural environment.)

A "foreign" gene refers to a gene not normally found in the host organism, but that is introduced into the host organism by gene transfer. Foreign genes can comprise native genes inserted into a non-native organism, or chimeric constructs. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most host cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the gene sequence that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). "Mature" protein refers to a post-translationally processed polypeptide; i.e., one from which any pre- or propeptides present in the primary translation product have been removed. "Precursor" protein refers to the primary product of translation of mRNA; i.e., with pre- and pro-peptides still present. Pre- and pro-peptides may be but are not limited to intracellular localization signals.

"Stable transformation" refers to the transfer of a nucleic acid fragment into a genome of a host organism, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al., (1987) *Nature* (London) 327:70–73; U.S. Pat. No. 4,945,050), or an *Agrobacterium*-mediated method using an appropriate Ti plasmid containing the transgene (Ishida Y. et al., 1996, Nature Biotech. 14:745–750). The term "transformation" as used herein refers to both stable transformation and transient transformation.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al, *Cold Spring Harbor Symp. Quant. Biol.* 51:263–273 (1986); Erlich et al, European Patent Application 50,424; European Patent Application 84,796; European Patent Application 258,017, European Patent Application 237,362; Mullis, European Patent Application 201,184, Mullis et al U.S. Pat. No. 4,683,202; Erlich, U.S. Pat. No. 4,582,788; and Saiki et al, U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20–50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be itself or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

Production of the Δ4-Desaturase Enyzme

Once the gene encoding the Δ4-desaturase enzyme has been isolated, it may then be introduced into either a prokaryotic or eukaryotic host cell through the use of a vector or construct. The vector, for example, a bacteriophage, cosmid or plasmid, may comprise the nucleotide sequence encoding the Δ4-desaturase enzyme, as well as any regulatory sequence (e.g., promoter) which is functional in the host cell and is able to elicit expression of the desaturase encoded by the nucleotide sequence. The regulatory sequence (e.g., promoter) is in operable association with or operably linked to the nucleotide sequence. (A promoter is said to be "operably linked" with a coding sequence if the promoter affects transcription or expression of the coding sequence.) Suitable promoters include, for example, those from genes encoding alcohol dehydrogenase, glyceraldehyde-3-phosphate dehydrogenase, phosphoglucoisomerase, phosphoglycerate kinase, acid phosphatase, T7, TPI, lactase, metallothionein, cytomegalovirus immediate early, whey acidic protein, glucoamylase, and promoters activated in the presence of galactose, for example, GAL1 and GAL10. Additionally, nucleotide sequences which encode other proteins, oligosaccharides, lipids, etc. may also be included within the vector as well as other regulatory sequences such as a polyadenylation signal (e.g., the poly-A signal of SV-40T-antigen, ovalalbumin or bovine growth hormone). The choice of sequences present in the construct is dependent upon the desired expression products as well as the nature of the host cell.

As noted above, once the vector has been constructed, it may then be introduced into the host cell of choice by methods known to those of ordinary skill in the art including, for example, transfection, transformation and electroporation (see *Molecular Cloning: A Laboratory Manual*, $2^{nd}$ ed., Vol. 1–3, ed. Sambrook et al., Cold Spring Harbor Laboratory Press (1989)). The host cell is then cultured under suitable conditions permitting expression of the genes leading to the production of the desired PUFA, which is then recovered and purified.

Examples of suitable prokaryotic host cells include, for example, bacteria such as *Escherichia coli, Bacillus subtilis* as well as *Cyanobacteria* such as *Spirulina spp.* (i.e., blue-green algae). Examples of suitable eukaryotic host cells include, for example, mammalian cells, plant cells, yeast cells such as *Saccharomyces cerevisiae, Saccharomyces carlsbergensis, Lipomyces starkey, Candida spp.* such as *Yarrowia (Candida) lipolytica, Kluyveromyces spp., Pichia spp., Trichoderma spp.* or *Hansenula spp.*, or fungal cells such as filamentous fungal cells, for example, *Aspergillus, Neurospora* and *Penicillium*. Preferably, *Saccharomyces cerevisiae* (baker's yeast) cells are utilized.

Expression in a host cell can be accomplished in a transient or stable fashion. Transient expression can occur from introduced constructs which contain expression signals functional in the host cell, but which constructs do not replicate and rarely integrate in the host cell, or when the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

A transgenic mammal may also be used in order to express the enzyme of interest (i.e., Δ4-desaturase), and ultimately the PUFA(s) of interest. More specifically, once the above-described construct is created, it may be inserted into the pronucleus of an embryo. The embryo may then be implanted into a recipient female. Alternatively, a nuclear transfer method could also be utilized (Schnieke et al., Science 278:2130–2133 (1997)). Gestation and birth are then permitted (see, e.g., U.S. Pat. No. 5,750,176 and U.S. Pat. No. 5,700,671). Milk, tissue or other fluid samples from the offspring should then contain altered levels of PUFAs, as compared to the levels normally found in the non-transgenic animal. Subsequent generations may be monitored for production of the altered or enhanced levels of PUFAs and thus incorporation of the gene encoding the desired desaturase enzyme into their genomes. The mammal utilized as the host may be selected from the group consisting of, for example, a mouse, a rat, a rabbit, a pig, a goat, a sheep, a horse and a cow. However, any mammal may be used provided it has the ability to incorporate DNA encoding the enzyme of interest into its genome.

For expression of a desaturase polypeptide, functional transcriptional and translational initiation and termination regions are operably linked to the DNA encoding the desaturase polypeptide. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. Expression in a plant tissue and/or plant part presents certain efficiencies, particularly where the tissue or part is one which is harvested early, such as seed, leaves, fruits, flowers, roots, etc. Expression can be targeted to that location with the plant by utilizing specific regulatory sequence such as those of U.S. Pat. Nos. 5,463,174, 4,943,674, 5,106,739, 5,175,095, 5,420,034, 5,188,958, and 5,589,379. Alternatively, the expressed protein can be an enzyme which produces a product which may be incorporated, either directly or upon further modifications, into a fluid fraction from the host plant. Expression of a desaturase gene, or antisense desaturase transcripts, can alter the levels of specific PUFAs, or derivatives thereof, found in plant parts and/or plant tissues. The desaturase polypeptide coding region may be expressed either by itself or with other genes, in order to produce tissues and/or plant parts containing higher proportions of desired PUFAs or in which the PUFA composition more closely resembles that of human breast milk (Prieto et al., PCT publication WO 95/24494). The termination region may be derived from the 3' region of the gene from which the initiation region was obtained or from a different gene. A large number of termination regions are known to and have been found to be satisfactory in a variety of hosts from the same and different genera and species. The termination region usually is selected as a matter of convenience rather than because of any particular property.

As noted above, a plant (e.g., *Glycine max* (soybean) or *Brassica napus* (canola)) or plant tissue may also be utilized as a host or host cell, respectively, for expression of the desaturase enzyme which may, in turn, be utilized in the production of polyunsaturated fatty acids. More specifically, desired PUFAS can be expressed in seed. Methods of isolating seed oils are known in the art. Thus, in addition to providing a source for PUFAs, seed oil components may be manipulated through the expression of the desaturase gene, as well as perhaps other desaturase genes and elongase genes, in order to provide seed oils that can be added to nutritional compositions, pharmaceutical compositions, animal feeds and cosmetics. Once again, a vector which comprises a DNA sequence encoding the desaturase operably linked to a promoter, will be introduced into the plant tissue or plant for a time and under conditions sufficient for expression of the desaturase gene. The vector may also comprise one or more genes that encode other enzymes, for example, Δ5-desaturase, elongase, Δ12-desaturase, Δ15-desaturase, Δ17-desaturase, and/or Δ19-desaturase. The plant tissue or plant may produce the relevant substrate (e.g., adrenic acid or ω3-docosapentaenoic acid) upon which the enzyme acts or a vector encoding enzymes which produce such substrates may be introduced into the plant tissue, plant cell or plant. In addition, substrate may be sprayed on plant tissues expressing the appropriate enzymes. Using these various techniques, one may produce PUFAs (e.g., n-6 unsaturated fatty acids such as ω6-docosapentaenoic acid, or n-3 fatty acids such as docosahexaenoic acid) by use of a plant cell, plant tissue or plant. It should also be noted that the invention also encompasses a transgenic plant comprising the above-described vector, wherein expression of the nucleotide sequence of the vector results in production of a polyunsaturated fatty acid in, for example, the seeds of the transgenic plant.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens*, and obtaining transgenic plants have been published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011, McCabe et. al., *BiolTechnology* 6:923 (1988), Christou et al., *Plant Physiol.* 87:671–674 (1988)); Brassica (U.S. Pat. No. 5,463,174); peanut (Cheng et al., *Plant Cell Rep.* 15:653–657

(1996), McKently et al., *Plant Cell Rep.* 14:699–703 (1995)); papaya; and pea (Grant et al., *Plant Cell Rep.* 15:254–258, (1995)).

Transformation of monocotyledons using electroporation, particle bombardment, and *Agrobacterium* have also been reported. Transformation and plant regeneration have been achieved in asparagus (Bytebier et al., *Proc. Natl. Acad. Sci.* (USA) 84:5354, (1987)); barley (Wan and Lemaux, *Plant Physiol* 104:37 (1994)); Zea mays (Rhodes et al., *Science* 240:204 (1988), Gordon-Kamm et al., *Plant Cell* 2:603–618 (1990), Fromm et al., *BiolTechnology* 8:833 (1990), Koziel et al., *BiolTechnology* 11:194, (1993), Armstrong et al., *Crop Science* 35:550–557 (1995)); oat (Somers et al., *BiolTechnology* 10:1589 (1992)); orchard grass (Horn et al., *Plant Cell Rep.* 7:469 (1988)); rice (Toriyama et al., *TheorAppl. Genet.* 205:34 (1986); Part et al., *Plant Mol. Biol.* 32:1135–1148, (1996); Abedinia et al., *Aust. J. Plant Physiol.* 24:133–141 (1997); Zhang and Wu, *Theor. Appl. Genet.* 76:835 (1988); Zhang et al. *Plant Cell Rep.* 7:379, (1988); Battraw and Hall, *Plant Sci.* 86:191–202 (1992); Christou et al., Bio/Technology 9:957 (1991)); rye (De la Pena et al., *Nature* 325:274 (1987)); sugarcane (Bower and Birch, *Plant J.* 2:409 (1992)); tall fescue (Wang et al., *BiolTechnology* 10:691 (1992)), and wheat (Vasil et al., *BiolTechnology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454–457 (1988); Marcotte et al., *Plant Cell* 1:523–532 (1989); McCarty et al., *Cell* 66:895–905 (1991); Hattori et al., *Genes Dev.* 6:609–618 (1992); Goff et al., *EMBO J.* 9:2517–2522 (1990)).

Transient expression systems may be used to functionally dissect gene constructs (see generally, Maliga et al., Methods in Plant Molecular Biology, Cold Spring Harbor Press (1995)). It is understood that any of the nucleic acid molecules of the present invention can be introduced into a plant cell in a permanent or transient manner in combination with other genetic elements such as vectors, promoters, enhancers etc.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, N.Y. (1997)).

The substrates which may be produced by the host cell either naturally or transgenically, as well as the enzymes which may be encoded by DNA sequences present in the vector which is subsequently introduced into the host cell, are shown in FIG. 1.

Uses of the Δ4-Desaturase Gene and Enzyme Encoded Thereby

As noted above, the isolated desaturase genes and the desaturase enzymes encoded thereby have many uses. For example, the gene and corresponding enzyme may be used indirectly or directly in the production of polyunsaturated fatty acids, for example, Δ4-desaturase may be used in the production of ω6-docosapentaenoic acid or docosahexaenoic acid. "Directly" is meant to encompass the situation where the enzyme directly converts the acid to another acid, the latter of which is utilized in a composition (e.g., the conversion of adrenic acid to ω6-docosapentaenoic acid). "Indirectly" is meant to encompass the situation where an acid is converted to another acid (i.e., a pathway intermediate) by the desaturase (e.g., adrenic acid to ω6-docosapentaenoic acid) and then the latter acid is converted to another acid by use of a desaturase or non-desaturase enzyme (e.g., ω6-docosapentaenoic acid to docosahexaenoic acid by Δ19-desaturase). Also, the present invention includes "indirect" situations in which the PUFA is first converted to another polyunsaturated fatty acid by a non-Δ4-desaturase enzyme (for example, an elongase or another desaturase) and then converted to a final product via Δ4-desaturase. For example, eicosapentaenoic acid may be converted to ω3-docosapentaenoic acid by an elongase, and then converted to docosahexaenoic acid by a Δ4-desaturase. These polyunsaturated fatty acids (i.e., those produced either directly or indirectly by activity of the desaturase enzyme) may be added to, for example, nutritional compositions, pharmaceutical compositions, cosmetics, and animal feeds, all of which are encompassed by the present invention. These uses are described, in detail, below.

Nutritional Compositions

The present invention includes nutritional compositions. Such compositions, for purposes of the present invention, include any food or preparation for human consumption including for enteral or parenteral consumption, which when taken into the body (a) serve to nourish or build up tissues or supply energy and/or (b) maintain, restore or support adequate nutritional status or metabolic function.

The nutritional composition of the present invention comprises at least one oil or acid produced directly or indirectly by use of the desaturase gene, in accordance with the present invention, and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany certain metabolic conditions (e.g., metabolic disorders).

Examples of macronutrients which may be added to the composition include but are not limited to edible fats, carbohydrates and proteins. Examples of such edible fats include but are not limited to coconut oil, borage oil, fungal oil, black current oil, soy oil, and mono- and diglycerides. Examples of such carbohydrates include but are not limited to glucose, edible lactose and hydrolyzed search. Additionally, examples of proteins which may be utilized in the nutritional composition of the invention include but are not limited to soy proteins, electrodialysed whey, electrodialysed skim milk, milk whey, or the hydrolysates of these proteins.

With respect to vitamins and minerals, the following may be added to the nutritional compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the nutritional compositions of the present invention will be of semi-purified or purified origin. By semi-purified or purified is meant a material which has been prepared by purification of a natural material or by synthesis.

Examples of nutritional compositions of the present invention include but are not limited to infant formulas, dietary supplements (e.g., adult nutritional products and oil), dietary substitutes, and rehydration compositions. Nutritional compositions of particular interest include but are not limited to those utilized for enteral and parenteral supplementation for infants, specialist infant formulas, supplements for the elderly, and supplements for those with gastrointestinal difficulties and/or malabsorption.

The nutritional composition of the present invention may also be added to food even when supplementation of the diet is not required. For example, the composition may be added to food of any type including but not limited to margarines, modified butters, cheeses, milk, yogurt, chocolate, candy, snacks, salad oils, cooking oils, cooking fats, meats, fish and beverages.

In a preferred embodiment of the present invention, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to polyunsaturated fatty acids produced in accordance with the present invention, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art. (See also the Examples below.)

The enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutritional formulas are well known in the art and are commercially available (e.g. SIMILAC®, ENSURE®, JEVITY® and ALIMENTUM® from Ross Products Division, Abbott Laboratories, Columbus, Ohio). An oil or acid produced in accordance with the present invention may be added to any of these formulas.

The energy density of the nutritional compositions of the present invention, when in liquid form, may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 660 mOsm.

The nutritional formula may include macronutrients, vitamins, and minerals, as noted above, in addition to the PUFAs produced in accordance with the present invention. The presence of these additional components helps the individual ingest the minimum daily requirements of these elements. In addition to the provision of PUFAs, it may also be desirable to add zinc, copper, folic acid and antioxidants to the composition. It is believed that these substances boost a stressed immune system and will therefore provide further benefits to the individual receiving the composition. A pharmaceutical composition may also be supplemented with these elements.

In a more preferred embodiment, the nutritional composition comprises, in addition to antioxidants and at least one PUFA, a source of carbohydrate wherein at least 5 weight percent of the carbohydrate is indigestible oligosaccharide. In a more preferred embodiment, the nutritional composition additionally comprises protein, taurine, and carnitine.

As noted above, the PUFAs produced in accordance with the present invention, or derivatives thereof, may be added to a dietary substitute or supplement, particularly an infant formula, for patients undergoing intravenous feeding or for preventing or treating malnutrition or other conditions or disease states. As background, it should be noted that human breast milk has a fatty acid profile comprising from about 0.15% to about 0.36% as DHA, from about 0.03% to about 0.13% as EPA, from about 0.30% to about 0.88% as AA, from about 0.22% to about 0.67% as DGLA, and from about 0.27% to about 1.04% as GLA. Thus, fatty acids such as AA, EPA and/or docosahexaenoic acid (DHA), produced in accordance with the present invention, can be used to alter, for example, the composition of infant formulas in order to better replicate the PUFA content of human breast milk or to alter the presence of PUFAs normally found in a non-human mammal's milk. In particular, a composition for use in a pharmacologic or food supplement, particularly a breast milk substitute or supplement, will preferably comprise one or more of AA, DGLA and GLA. More preferably, the oil will comprise from about 0.3 to 30% AA, from about 0.2 to 30% DGLA, and/or from about 0.2 to about 30% GLA.

Parenteral nutritional compositions comprising from about 2 to about 30 weight percent fatty acids calculated as triglycerides are encompassed by the present invention. The preferred composition has about 1 to about 25 weight percent of the total PUFA composition as GLA (U.S. Pat. No. 5,196,198). Other vitamins, particularly fat-soluble vitamins such as vitamin A, D, E and L-carnitine can optionally be included. When desired, a preservative such as alpha-tocopherol may be added in an amount of about 0.1% by weight.

In addition, the ratios of AA, DGLA and GLA can be adapted for a particular given end use. Wheii formulated as a breast milk supplement or substitute, a composition which comprises one or more of AA, DGLA and GLA will be provided in a ratio of about 1:19:30 to about 6:1:0.2, respectively. For example, the breast milk of animals can vary in ratios of AA:DGLA:GLA ranging from 1:19:30 to 6:1:0.2, which includes intermediate ratios which are preferably about 1:1:1, 1:2:1, 1:1:4. When produced together in a host cell, adjusting the rate and percent of conversion of a precursor substrate such as GLA and DGLA to AA can be used to precisely control the PUFA ratios. For example, a 5% to 10% conversion rate of DGLA to AA can be used to produce an AA to DGLA ratio of about 1:19, whereas a conversion rate of about 75% TO 80% can be used to produce an AA to DGLA ratio of about 6:1. Therefore, whether in a cell culture system or in a host animal, regulating the timing, extent and specificity of desaturase expression, as well as the expression of other desaturases and elongases, can be used to modulate PUFA levels and ratios. The PUFAs produced in accordance with the present invention (e.g., AA and EPA) may then be combined with other PUFAs/acids (e.g., GLA) in the desired concentrations and ratios.

Additionally, PUFA produced in accordance with the present invention or host cells containing them may also be used as animal food supplements to alter an animal's tissue or milk fatty acid composition to one more desirable for human or animal consumption.

Pharmaceutical Compositions

The present invention also encompasses a pharmaceutical composition comprising one or more of the acids and/or resulting oils produced using the desaturase genes, in accordance with the methods described herein. More specifically, such a pharmaceutical composition may comprise one or more of the acids and/or oils as well as a standard, well-known, non-toxic pharmaceutically acceptable carrier, adjuvant or vehicle such as, for example, phosphate buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectable, or topical ointment or cream. Proper fluidity can be maintained, for example, by the maintenance of the required particle size in the case of dispersions and by the use of surfactants. It may also be desirable to include isotonic agents, for example, sugars, sodium chloride and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art. For example, PUFAs produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant PUFA(s). The antioxidant and PUFA components should fit within the guidelines presented above.

For intravenous administration, the PUFAs produced in accordance with the present invention or derivatives thereof may be incorporated into commercial formulations such as Intralipids™. The typical normal adult plasma fatty acid profile comprises 6.64 to 9.46% of AA, 1.45 to 3.11% of DGLA, and 0.02 to 0.08% of GLA. These PUFAs or their metabolic precursors can be administered alone or in combination with other PUFAs in order to achieve a normal fatty acid profile in a patient. Where desired, the individual components of the formulations may be provided individually, in kit form, for single or multiple use. A typical dosage of a particular fatty acid is from 0.1 mg to 20 g (up to 100 g) daily and is preferably from 10 mg to 1, 2, 5 or 10 g daily.

Possible routes of administration of the pharmaceutical compositions of the present invention include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant. The route of administration will, of course, depend upon the desired effect. For example, if the composition is being utilized to treat rough, dry, or aging skin, to treat injured or burned skin, or to treat skin or hair affected by a disease or condition, it may perhaps be applied topically.

The dosage of the composition to be administered to the patient may be determined by one of ordinary skill in the art and depends upon various factors such as weight of the patient, age of the patient, immune status of the patient, etc.

With respect to form, the composition may be, for example, a solution, a dispersion, a suspension, an emulsion or a sterile powder which is then reconstituted.

The present invention also includes the treatment of various disorders by use of the pharmaceutical and/or nutritional compositions described herein. In particular, the compositions of the present invention may be used to treat restenosis after angioplasty. Furthermore, symptoms of inflammation, rheumatoid arthritis, asthma and psoriasis may also be treated with the compositions of the invention. Evidence also indicates that PUFAs may be involved in calcium metabolism; thus, the compositions of the present invention may, perhaps, be utilized in the treatment or prevention of osteoporosis and of kidney or urinary tract stones.

Additionally, the compositions of the present invention may also be used in the treatment of cancer. Malignant cells have been shown to have altered fatty acid compositions. Addition of fatty acids has been shown to slow their growth, cause cell death and increase their susceptibility to chemotherapeutic agents. Moreover, the compositions of the present invention may also be useful for treating cachexia associated with cancer.

The compositions of the present invention may also be used to treat diabetes (see U.S. Pat. No. 4,826,877 and Horrobin et al., Am. J. Clin. Nutr. Vol. 57 (Suppl.) 732S–737S). Altered fatty acid metabolism and composition have been demonstrated in diabetic animals.

Furthermore, the compositions of the present invention, comprising PUFAs produced either directly or indirectly through the use of the desaturase enzymes, may also be used in the treatment of eczema, in the reduction of blood pressure, and in the improvement of mathematics examination scores. Additionally, the compositions of the present invention may be used in inhibition of platelet aggregation, induction of vasodilation, reduction in cholesterol levels, inhibition of proliferation of vessel wall smooth muscle and fibrous tissue (Brenner et al., Adv. Exp. Med. Biol. Vol. 83, p.85–101, 1976), reduction or prevention of gastrointestinal bleeding and other side effects of non-steroidal anti-inflammatory drugs (see U.S. Pat. No. 4,666,701), prevention or treatment of endometriosis and premenstrual syndrome (see U.S. Pat. No. 4,758,592), and treatment of myalgic encephalomyelitis and chronic fatigue after viral infections (see U.S. Pat. No. 5,116,871).

Further uses of the compositions of the present invention include use in the treatment of AIDS, multiple sclerosis, and inflammatory skin disorders, as well as for maintenance of general health.

Additionally, the composition of the present invention may be utilized for cosmetic purposes. It may be added to pre-existing cosmetic compositions such that a mixture is formed or may be used as a sole composition.

Veterinary Applications

It should be noted that the above-described pharmaceutical and nutritional compositions may be utilized in connection with animals (i.e., domestic or non-domestic), as well as humans, as animals experience many of the same needs and conditions as humans. For example, the oil or acids of the present invention may be utilized in animal feed supplements, animal feed substitutes, animal vitamins or in animal topical ointments.

The present invention may be illustrated by the use of the following non-limiting examples:

EXAMPLE I

Design of Degenerate Oligonucleotides for the Isolation of Desaturases from *Thraustochytrium aureum* and cDNA Library Construction The fatty acid composition analysis of the marine fungus *Thraustochytrium aureum* (*T. aureum*) (ATCC 34304) was investigated to determine the types and amounts of polyunsaturated fatty acids (PUFAs). This fungus had substantial amounts of longer chain PUFAs such as arachidonic acid (ARA, 20:4n-6) and eicosapentaenoic acid (EPA, 20:5 n-3). However, *T. aureum* also produced PUFAs such as adrenic acid (ADA, 22:4n-6) ω6-docosapentaenoic acid ω6-DPA 22:5n-6), ω3-docosapentaenoic acid (ω3-DPA 22:5n-3), with the highest amount of fatty acid being docosahexaenoic acid (DHA, 22:6n-3) (see FIG. 1). Thus in addition to Δ6-, Δ5- and Δ7-desaturases, *T. aureum* probably contains a Δ9-desaturase which converts ADA to ω3-DPA or ω6-DPA to DHA and/or a Δ4-desaturase which desaturates ADA to ω6-DPA or ω3-DPA to DHA. The goal was therefore to attempt to isolate the predicted desaturase genes from *T. aureum*, and to verify the functionality of the enzymes by expression in an alternate host.

To isolate genes encoding for functional desaturase enzymes, a cDNA library was constructed. *T. aureum* (ATCC 34304) cells were grown in BY+Media (#790, Difco, Detroit, Mich.) at room temperature for 4 days, in the presence of light, and with constant agitation (250 rpm) to obtain the maximum biomass. These cells were harvested by centrifugation at 5000 rpm for 10 minutes and rinsed in ice-cold RNase-free water. These cells were then lysed in a French press at 10,000 psi, and the lysed cells were directly collected into TE buffered phenol. Proteins from the cell lysate were removed by repeated phenol: chloroform (1:1 v/v) extraction, followed by a chloroform extraction. The nucleic acids from the aqueous phase were precipitated at −70° C. for 30 minutes using 0.3M (final concentration) sodium acetate (pH 5.6) and one volume of isopropanol. The precipitated nucleic acids were collected by centrifugation at 15,000 rpm for 30 minutes at 4° C., vacuum-dried for 5 minutes and then treated with DNaseI (RNase-free) in 1X DNase buffer (20 mM Tris-Cl, pH 8.0; 5mM $MgC_2$) for 15 minutes at room temperature. The reaction was quenched with 5 mM EDTA (pH 8.0) and the RNA further purified using the Qiagen RNeasy Maxi kit (Qiagen, Valencia, Calif.) as per the manufacturer's protocol.

Messenger RNA was isolated from total RNA using oligo dT cellulose resin, and the pBluescript II XR library construction kit (Stratagene, La Jolla, Calif.) was used to synthesize double stranded cDNA which was then directionally cloned (5' EcoRI/3' XhoI) into pBluescript II SK(+) vector (Stratagene, La Jolla, Calif.). The *T. aureum* library contained approximately $2.5 \times 10^6$ clones each with an average insert size of approximately 700 bp. Genomic DNA from PUFA-producing *T. aureum* cultures was isolated by crushing the culture in liquid nitrogen and was purified using Qiagen Genomic DNA Extraction Kit (Qiagen, Valencia, Calif.).

The approach taken was to design degenerate oligonucleotides (primers) that represent amino acid motifs that are conserved in known desaturases. These primers could be then used in a PCR reaction to identify a fragment containing the conserved regions in the predicted desaturase genes from fungi. Since the only fungal desaturases which have been identified are Δ5- and Δ6-desaturase genes from *Mortierella alpina* (Genbank accession numbers AF067650, AB020032, respectively), desaturase sequences from plants as well as animals were taken into consideration during the design of these degenerate primers. In particular, known Δ5- and Δ6-desaturase sequences from the following organisms were used for the design of these degenerate primers: *Mortierella alpina, Borago officinalis, Helianthus annuus, Brassica napus, Dictyostelium discoideum, Rattus norvegicus, Mus musculus, Homo sapiens, Caenorhabditis elegans, Arabidopsis thaliana,* and *Ricinus communis*. The degenerate primers used were as follows using the CODEHOP Blockmaker program

```
a. Protein motif 1:
NH3- VYDVTEWVKRHPGG -COOH

Primer RO834:
5'-GTBTAYGAYGTBACCGARTGGGTBAAGCGYCAYCCBGGHGGH-3'      (SEQ ID NO:1)

B. Protein Motif 2:
NH3- GASANWWKHQHNVHH -COOH

Primer RO835 (Forward):
5-'GGHGCYTCCGCYAACTGGTGGAAGCAYCAGCAYAACGTBCAYCAY-3'   (SEQ ID NO:2)

Primer RO836 (Reverse):
5-'RTGRTGVACGTTRTGCTGRTGCTTCCACCAGTTRGCGGARGCDCC-3'   (SEQ ID NO:3)

C. Protein Motif 3:
NH3- NYQIEHHLFPTM -COOH

Primer RO838 (Reverse)
5'-TTGATRGTCTARCTYGTRGTRGASAARGGVTGGTAC-3'           (SEQ ID NO:4)
```

In addition, two more primers were designed based on the 2nd and 3rd conserved 'Histidine-box' found in known Δ6-desaturases. These were:

```
Primer  5'-CATCATCATXGGRAAXARRTGRTG-3'    (SEQ ID NO:5)
RO753

Primer  5'-CTACTACTACTACAYCAYACXTAY        (SEQ ID NO:6)
RO754   ACXAAY-3'.
```

The degeneracy code for the oligonucleotide sequences was: B=C,G,T; H=A,C,T; S=C,G; R=A,G; V=A,C,G; Y=C,T; D=A,T,C; X=A,C,G,T

EXAMPLE II

Use of Degenerate Oligonucleotides for the Isolation of a Desaturase from a Fungus To isolate putative desaturase genes, total RNA was isolated using the lithium chloride method (Hoge, et al. (1982) Exp. Mycol. 6:225–232). Approximately 5 μg was reverse transcribed using the SuperScript Preamplification system (LifeTechnologies, Rockville, Md.) to produce first strand cDNA. The following primer combinations were used: RO834/836, RO834/838, RO835/836, RO835/838 and RO753/754 were used in several PCR reactions with different thermocycling parameters and Taq polymerase at annealing temperatures below 60° C., but no bands were produced.

In additional attempts to isolate fragments of desaturases, the degenerate primers RO834/838 (designed with the block maker program) and RO753/754 were used in a 50 μl reaction. The following components were combined: 2 μl of the first strand cDNA template, 20 mM Tris-HCl, pH 8.4, 50mM KCl, 1.5 mM MgCl$_2$, 200 μM each deoxyribonucleotide triphosphate, 0.2 pmole final concentration of each primer and cDNA polymerase (Clonetech, Palo Alto, Calif.). Thermocycling was carried out as follows: an initial denaturation at 94° C. for 3 minutes, followed by 35 cycles of; denaturation at 94° C. for 30 seconds, annealing at 60° C. for 30 seconds and extension at 72° C. for 1 minute. This was followed by a final extension at 72° C. for 7 minutes. Two faint bands of approximately 1000 bp were detected for primers RO834/838, while a slightly smaller but more intense band of 800–900 bp was found with the primer pair RO753/754. The reactions were separated on a 1% agarose gel, excised, and purified with the QiaQuick Gel Extraction Kit (Qiagen, Valencia, Calif.). The staggered ends on these fragments were 'filled-in' using T4 DNA polymerase (LifeTechnologies, Rockville, Md.) as per manufacture's specifications, and these DNA fragments were cloned into the PCR-Blunt vector (Invitrogen, Carlsbad, Calif.). The recombinant plasmids were transformed into TOP10 supercompetent cells (Invitrogen, Carlsbad, Calif.) and clones were partially sequenced.

Subsequently, the sequences of clone 30-3 (reaction with [RO834/838]) and clone 17-1 (reaction with RO753/754) were found to overlap to create a 1313 bp fragment. The fragment was translated and Tfasta used to search the GenBank database. The highest match was *Mortierella alpina* Δ5-desaturase (Genbank accession #AF067654) (27% homology in 202 amino acids), *Spirulina platensis* Δ6-desaturase (Genbank accession number X87094) (30% homology in 121 amino acids), *Dictyostelium discoideum* Δ5-desaturase (Genbank accession number AB02931) (26% homology in 131 amino acids), and *M. alpina* Δ6-desaturase (accession number AF 110510 (30% homology in 86 amino acids). Since there was a reasonable degree of amino acid homology to known desaturases, a full-length gene encoding a potential desaturase was sought to determine its activity when expressed in yeast.

EXAMPLE III

Isolation of the Full Length Gene Sequence from *T. aureum* (ATCC 34304)

To find the full-length gene, two separate PCR reactions were carried out in an attempt to determine the two ends of putative desaturase from the cDNA library. For the 3' end of the gene, RO898 (SEQ ID NO:7) (5'-CCCAGTCAC-GACGTTGTAAAACGACGGCCAG-3') (designed based on the sequence of the pBluescript SK(+) vector (Stragene, La Jolla, Calif.) was used in a PCR amplification reaction along with a gene specific primer RO930 (SEQ ID NO:8) (5'-GACGATTAACAAGGTGATTTCCCAGGATGTC). In this case, the Advantage –GC cDNA PCR kit (Clonetech, Palo Alto, Calif.) was used to overcome PCR amplification problems that occur with GC rich sequences (61% for 1313 bp fragment). PCR thermocycling conditions were as follows: the template was initially denatured at 94° C. for 3 minutes, followed by 30 cycles of [94° C. for 30 seconds, 52° C. for 30 seconds, and 72° C. for 1 minute], and finally an extension cycle at 72° C. for 7 minutes with 20 pmoles of each primer. The PCR products thus obtained was resolved on a 1% agarose gel, excised, and gel purified using the Qiagen Gel Extraction Kit (Qiagen, Valencia, Calif.). The staggered ends on the fragment was 'filled-in' using T4 DNA polymerase (LifeTechnologies, Rockville, Md.) as per manufactures specifications and cloned into the PCR-Blunt vector (Invitrogen, Carlsbad, Calif.) as described in Example II. Clone 93-3 sequence overlapped the original 1313 bp fragment and was found to contain an open reading frame, a stop codon, and a poly A tail indicating that this was the 3' end of the gene. Two primers were designed based on clone 93-3 sequence near the stop codon with an XhoI created site (underlined) as follows: RO973 (SEQ ID NO:9) (5'-GACTAACTCGAGTCACGTGGACCAGGC-CGTGAGGTCCT-3') and RO974 (SEQ ID NO:10) (5'-GACTAACTCGAGTTGACGAGGTTTGTAT GTTCG-GCGGTTTGCTTG-3'). Two primers were deliberately chosen because RO973, that contained the stop codon, was high in GC (60%) and might not amplify well. On the other hand, RO974, downstream of the stop codon, was much lower in GC (48%).

Following the same protocol as described above to isolate the 5' end of the gene, RO899 (SEQ ID NO:11) (5'-AGCGGATAACAATTTCACACAGGAAACAGC-3') (designed based on the sequence of the pBluescript SK(+) vector) and the gene specific oligonucleotide RO1004 (SEQ ID NO:12) (5'-TGGCTACCGTCGTGCTGGATGCAAGT-TCCG-3') were used for amplification of the cDNA library. Amplification was carried out using 10 pmols of each primer and the cDNA polymerase kit (Clonetech, Palo Alto, Calif.). The reaction conditions included an initial denaturation at 94° C. for 1 minute, followed by 30 cycles of [94° C. for 30 seconds, 68° C. for 3 minutes], and finally an extension cycle at 68° C. for 5 minutes. The PCR products thus obtained were cloned into the PCR-Blunt vector (Invitrogen, Carlsbad, Calif.) following the same protocol as described above. The recombinant plasmids were transformed into TOP10 supercompetent cells (Invitrogen, Carlsbad, Calif.), and clones were sequenced. Clone 1004-5 contained an open reading frame, several start codons, and overlapped the original 1313 bp sequence indicating that this was the 5' end of the gene.

To isolate the full-length gene, a primer for the 5' end of the putative desaturase was designed with a created EcoRI (underlined) as follows: RO1046 (SEQ ID NO:13) (5'-CGCATGGAATTCATGACG-GTCGGGTTTGACGAAACGGTG-3').

To isolate a full-length clone, both RO1046/973 and RO1046/974 were used with cDNA isolated from the library and genomic DNA as a target. Both cDNA polymerase (Clonetech, Palo Alto, Calif.) and -GC Advantage Polymerase (Clonetech, Palo Alto, Calif.) were used to amplify their respective targets with 10 pmol of primer with the following reaction conditions: an initial denaturation at 94° C. for 1 minute, followed by 30 cycles of [94° C. for 30 seconds, 68° C. for 3 minutes], and finally an extension cycle at 68° C. for 5 minutes. The reactions were gel purified, cut with EcoRI/XhoI and cloned into EcoRI/XhoI prepared yeast expression vector pYX242 (Invitrogen, Carlsbad, Calif.) that had been treated with shrimp alkaline phosphatase (Roche, Indianapolis, Ind.) to prevent recircularization. Initial analysis of the full-length sequences showed several base changes. Clones 112-3 and 112-5 (designated pRTA7 and 8, respectively) were derived from the amplification with genomic DNA and -GC Advantage polymerase using primers RO1046/974. Clone 110-3 (designated pRTA5) was derived from a reaction with RO1046/973, genomic DNA target and cDNA polymerase. Clone 111-1 (designated pRTA6) was isolated from the reaction using RO 1046/974, cDNA target and -GC Advantage polymerase kit. The sequence of these four plasmids, pRTA5 (SEQ ID NO:14), pRTA6 (SEQ ID NO:15), pRTA7 (SEQ ID NO:16), pRTA8 (SEQ ID NO:17) is shown in FIGS. 3–6, respectively. (Plasmids pRTA7 and pRTA8 were deposited with the American Type Culture Collection, 10801 University Boulevard, Manassas, Va. 20110 on Apr. 19, 2001 and were accorded accession numbers PTA-3301 and PTA-3300, respectively.) This putative desaturase of 1548 bp and 515 amino acids (see FIGS. 7–10 and SEQ ID NOS:18, 19, 20, 21, respectively) had many of the characteristics of described desaturases. The amino acids corresponding to the 5' end of the enzyme are homologous to cytochrome b5. There are also number of histidine boxes at the following amino acids: 178–183-(Q)HDGSH (SEQ ID NO:59); 213–219-(Q)HVLGHH (SEQ ID NO:60); 262–265-HPWH (SEQ ID NO:61); 271–275 HKFQH (SEQ ID NO:62); and 452–457(H)QIEHH (SEQ ID NO:63). At least either an H or a Q precedes three of these histidine boxes which is unusual. *Dictyostelium discoideum* (Genbank accession number AB029311) has two similar boxes [(Q)HVIGHH (SEQ ID NO:64) and (H)QVVHH (SEQ ID NO:65)], while *M. alpina* (Genbank accession number AF067654) has (Q)HMLGHH (SEQ ID NO:66) and *Synechocystis sp.* only has one (H)QVTHH (SEQ ID 67).

The sequences of the various putative desaturases differed from each other. Several of the base changes resulted in a change in amino acid, as shown in Table 1. These differences could be naturally occurring variants, introduced by PCR mismatch during final amplification, or a PCR error when the initial cDNA was produced. There are 7 individual amino acid changes between the four plasmids, none of which are shared (see FIG. 2A and B, underlined and bold amino acids). These differences could alter the activity of the encoded enzyme.

TABLE 1

Amino Acid Differences in Different Clones

| Amino Acid Number | PRTA5 | PRTA6 | PRTA7 | PRTA8 |
|---|---|---|---|---|
| 99 | F | S | F | F |
| 280 | F | F | L | F |
| 284 | F | F | F | S |
| 317 | Y | Y | N | Y |
| 332 | T | M | M | M |
| 410 | T | T | T | A |
| 513 | R | W | W | W |

EXAMPLE IV

Expression of Plasmids Containing Putative Desaturases in Yeast

All four plasmids were transformed into competent *Saccharomyces cerevisiae* strain 334. Yeast transformation was carried out using the Alkali-Cation Yeast Transformation Kit (BIO 101, Vista, Calif.) according to conditions specified by the manufacturer. Transformants were selected for leucine auxotrophy on media lacking leucine (DOB [-Leu]). To detect the specific desaturase activity of these clones, transformants were grown in the presence of 50 μM specific fatty acid substrates as listed below:

a. Linoleic acid (18:2n-6) (conversion to alpha-linolenic acid would indicate Δ15-desaturase activity and conversion to gamma-linolenic acid would indicate desaturase activity)

b. Alpha-linolenic acid (18:3n-3) (conversion to stearidonic acid would indicate Δ6-desaturase activity)

c. Arachidonic acid (20:4n-6) (conversion to eicosapentaenoic acid would indicate Δ17 desaturase activity).

d. Adrenic acid (22:4n-6) (conversion to ω3-docosapentaenoic acid would indicate Δ19-activity or conversion to ω6-docosapentaenoic acid would indicate Δ4-desaturase activity.

e. ω3-Docosapentaenoic acid (22:5: n-3) (conversion to docosahexaenoic would indicate Δ4-desaturase activity The negative control strain was *S. cerevisiae* 334 containing the unaltered pYX242 vector, and these were grown simultaneously.

The cultures were vigorously agitated (250 rpm) and grown for 48 hours a 24° C. in the presence of 50 μM (final concentration) of the various substrates in 50 ml of media lacking leucine after inoculation with overnight growth of single colonies in yeast peptone dextrose broth (YPD) at 30° C. The cells were pelleted, and the pellets vortexed in methanol; chloroform was added along with tritridecanoin (as an internal standard). These mixtures were incubated for at least an hour at room temperature or at 4° C. overnight. The chloroform layer was extracted and filtered through a Whatman filter with 1 gm anhydrous sodium sulfate to remove particulates and residual water. The organic solvents were evaporated at 40° C. under a stream of nitrogen. The extracted lipids were then derivitized to fatty acid methyl esters (FAME) for gas chromatography analysis (GC) by adding 2 mls of 0.5 N potassium hydroxide in methanol to a closed tube. The samples were heated to 95° C.–100° C. for 30 minutes and cooled to room temperature. Approximately 2 ml of 14% borontrifluoride in methanol was added and the heating repeated. After the extracted lipid mixture cooled, 2 ml of water and 1 ml of hexane were added to extract the fatty acid methyl esters (FAME) for analysis by GC. The percent conversion was calculated by dividing the product produced by the sum of (the product produced+ the substrate added) and then multiplying by 100.

The results showed conversion of ω-3DPA to DHA and ADA to ω6-DPA. This would indicate Δ4-desaturase activity (see Table 2).

TABLE 2

Percent Conversion of Different Substrate Concentrations to Product

| Clone | 25 uM 22:4n − 6 | 50 uM 22:4n − 6 | 100 uM 22:4n − 6 | 25 uM 22:5n − 3 | 50 uM 22:5n − 3 | 100 uM 22:5n − 3 |
|---|---|---|---|---|---|---|
| PYX242 (control) | 0 | 0 | 0 | 0 | 0 | 1.28 |
| PRTA5 | 3.91 | 0.9 | 1.24 | 10 | 6.89 | 3.1 |
| PRTA6 | 4.69 | 2.77 | 1.18 | 14.26 | 8.52 | 4.98 |
| PRTA7 | 10.97 | 6.11 | 3.14 | 36.34 | 17.52 | 9.92 |
| PRTA8 | 5.55 | 2.43 | 0.92 | 19.44 | 8.52 | 4.33 |

22:4n − 6 to 22:5n − 6 (Adrenic acid to ω6-Docosapentaenoic acid)
22:5n − 3 to 22:6n − 3 (ω3-Docosapentaenoic acid to Docosahexaenoic acid)

In particular, this is the first demonstration of a Δ4-desaturase gene with in vivo expression data. The conversion for the four clones ranged from 3.91% to 10.97% for production of ω6-DPA from ADA and 10% to 36.34% for production of DHA from ω-3DPA. The enzyme appears to be much more active in the production of DHA rather than ω6-DPA, as indicated by the reduced percent conversion, 36.34% vs 10.97%, respectively, for 25 μm of substrate for clone pRTA7. At 100 μm concentration of either substrate, the percent conversion (see Table 2) as well as the amount of product produced (data not shown) decreased, indicating that there may be feedback inhibition of the desaturation step by the substrate. The amount of ω3-DPA (22:5n-3) incorporated (as a percent of the total lipid) is similar for all four plasmids (see Table 3, below). However the amount produced as a percent of the total does vary from 2.74 (PRTA5) to 8.11% (PRTA7). The difference in the conversion rates and percent produced could be due to the difference in sequence, hence amino acid variation of the encoded enzyme in the four plasmids.

TABLE 3

Fatty Acid as a Percentage of Total Lipid Extracted from Yeast

| Clone | 22:4(n − 6) Incorporated | 22:5(n − 3) Produced | 22:5(n − 6) Incorporated | 22:6(n − 3) Produced |
|---|---|---|---|---|
| PYX242 (control) | 38.96 | 0 | 11.2 | 0 |
| PRTA5 | 14.5 | 0.59 | 19.8 | 2.74 |
| PRTA6 | 16.07 | 0.79 | 17.97 | 4.38 |
| PRTA7 | 39.88 | 4.91 | 14.21 | 8.11 |
| PRTA8 | 36.94 | 2.17 | 17.45 | 4.25 |

25 μM substrate data shown
Key:
22:4(n − 6) = Adrenic acid
22:5(n − 3) = ω3-Docosapentaenoic acid
22:5(n − 6) = ω6-Docosapentaenoic acid
22:6(n − 3) = Docosahexaenoic acid This data shows unequivocally that these plasmids indeed encode a Δ4-desaturase, which has preferred activity on conversion of ω3-DPA to DHA activity over conversion of ADA to ω6-DPA.

EXAMPLE V

Expression of Δ4-desaturase with the Mouse Elongase in Yeast

The plasmids pRTA7 and pRTA8 (which had the two highest percent conversion) may be individually co-transformed with pRMELO4, a clone that contains a mouse elongase gene from pRAE-84 (see U.S. patent application Ser. No. 09/624,670 incorporated herein in its entirety by reference). The mouse elongase of 879 base pairs (see FIG. 12 and SEQ ID NO:22) may be cloned as an EcoRI/SalI fragment in the yeast expression vector pYES2 (Invitrogen, Carlsbad, Calif.) at the EcoRI/XhoI sites. This elongase of 292 amino acids catalyzes several of the elongation steps in the PUFA pathway, specifically AA to ADA and EPA to ω3-DPA. ADA and ω3-DPA are substrates for the Δ4-desaturase. Yeast transformants may be selected on minimal media lacking leucine and uracil (DOB[-Leu-Ura]) for selection of Δ4-desaturase (pRTA7 or pRTA8) and pRMELO4 (mouse elongase). Growth and expression of the yeast culture containing pRMELO4 and pRTA7 or pRTA8 in minimal media lacking uracil and leucine and 2% galactose may result in elongation of exogenously added AA to ADA and Δ4 desaturation to ω6-DPA. Additionally, supplementation of EPA to the yeast minimal media may result in elongation to ω3-DPA by the elongase which may then be desaturated by the Δ4-desaturase to produce DHA as shown in FIG. 1. This has been previously demonstrated with elongases and other desaturases to produce AA and EPA (see PCT application WO 00/12720) and provides parallel experimental data to show that elongation of a substrate and subsequent desaturation can take place in vivo in an organism such as yeast and potentially other organisms. Further, the present data demonstrates the ability of the Δ4-desaturase to work with another enzyme in the PUFA biosynthetic pathway to produce either ω6-DPA or DHA from the precursors AA and EPA, respectively.

EXAMPLE VI

Homoloque of Δ4-desaturase from *Schizochytrium aggregatum* (ATCC 28209)

In parallel to Example II, RNA was isolated by the acid phenol method from *Schizochytrium aggregatum* (*S. aggregatum*) ATCC 28209. Briefly, pellets of *S. aggregatum* were washed with cold deionized water and repelleted for 5 minutes at 3000 rpm. Approximatley 10 ml of TES solution (10 mM Tris-CL pH 7.5, 10 mM EDTA, and 0.5% SDS) was used to resuspend the pellet. Then 10 ml of acid phenol was added and incubation followed for one hour at 65° C. The pellet was placed on ice for 5 minutes, centrifuged for 5 minutes at 1000×g at 4° C., and the aqueous phase transferred to a new tube. An additional 10 ml of acid phenol was added to the aqueous phase, the mixture vortexed and separated as before. The aqueous phase containing the nucleic acids was transferred to a new tube. Approximately 1 ml of sodium acetate pH 5.3 and 25 ml of ice-cold ethanol were added for overnight precipitation at −70 C. The next day, the tubes were centrifuged for 15 minutes at 14,000 rpm at 4° C. and the supernatant decanted. The pellet was washed with 10 ml of 70% ethanol and centrifuged as in the previous step. The pellet was dried and resuspended in 500 ul of RNAse free deionized water. The RNA was further purified using the Qiagen RNeasy Maxikit (Qiagen, Valencia, Calif.) as per the manufacturer's protocol.

cDNA was generated using oligo dT with the SuperScript Preamplification system (Life Technologies, Rockville, Md.) with 5 μg of RNA from *S. aggregatum*. Since *S. aggregatum* produces large quantities of DHA, a Δ4-desaturase would be required for DHA production. In an identical experiment, primers RO753 (SEQ ID NO:5) and RO754 (SEQ ID NO:6) were used in the same reaction as in Example II to produce a band around 800 base pairs. As before the DNA generated from the PCR reaction was separated on a 1% gel, excised, purified, and cloned into the PCR-Blunt vector (Invitrogen, Carlsbad, Calif.). The DNA sequence generated from clones saa9 and saa5 overlapped to create the sequence saa.con (SEQ ID NO:24 and FIG. 13). The translation of the open reading frame of saa.con DNA sequence to an amino acid sequence (SEQ ID NO:25 and FIG. 14) aligned with pRTA7 is shown in FIG. 15.

The amino acid sequence of the Δ4-desaturase from clone pRTA7 has 79.1% identity with the translated saa.con sequence over 249 amino acids. This sequence, due to its high identity with a known Δ4-desaturase, is most likely a fragment of a Δ4-desaturase from *S. aggregcaum*. This example provides evidence that this procedure can be used to isolate Δ4-desaturases from other organisms.

EXAMPLE VII

Isolation of Δ4-Desaturase Nucleotide Sequences from *Schizochytrium aggregatum* (ATCC 28209) and *Thraustochytrium aureum* (BICC 7091)

To isolate the 5' and 3'-ends, new primers were designed based on the internal sequence of the isolated *S. aggregatum* fragment shown in Example VI. For the 5 prime end of the gene, RO1240 (SEQ ID NO:26) (5'-CCC TCG ATG ATG TGG TTG ACG ATG AAC -3') was used and subsequently 5 prime nested primer RO1239 (SEQ ID NO:27) (5'-CGG AGC ATG GGG TAG GTG CTG AAG AC-3'). For the 3 prime end, RO1236 (SEQ ID NO:28) (5'-CCA ACT GCC GTT ACG CCA GCA AGT -3') was used followed by 3 prime nested primer RO1237 (SEQ ID NO:29) (5'-CAA GCT CTT CTT CAT CGC CCA CTT TTC G-3'), for a second reaction to isolate the other end of the gene. RACE (rapid amplification of cDNA ends) ready cDNA was used as a target for the reactions. To prepare this material, approximately 5 μg of total RNA was used according the manufacturer's direction with the GENRACER™ kit (Invitrogen, Carlsbad, Calif.) and SUPERSCRIPT II™ enzyme (Invitrogen, Carlsbad, Calif.) for reverse transcription to produce cDNA target. For the initial amplification of the ends, the following thermocycling protocol was used in a Perkin Elmer 9600: initial melt at 94° C. for 2 minutes followed by 5 cycles of 94° C. for 30 seconds and 72° C. for 3 minutes, 10 cycles of 94° C. 30 seconds, 70° C. for 30 seconds, and 72° C. for 3 minutes and 20 cycles of 94° C. for 30 seconds, 68° C. for 30 seconds and 72° C. for 3 minutes, followed by an extension of 72° C. for 10 minutes. The first PCR reaction was performed with 10 pMol of RO1240 and 30 pMol GeneRacer® 5 prime primer (SEQ ID NO:30) (5'- CGA CTG GAG CAC GAG GAC ACT GA-3') or RO1236 and GeneRacer® 3 prime primer (SEQ ID NO:31) (5'-GCT GTC AAC GAT ACG CTA CGT AAC G-3'). The reaction contained 1 ul of cDNA in a final volume of 50 ul with Platinum Taq® PCRx (Clonetech, Palo Alto, Calif.) using MgSO$_4$ according to the manufacturer's directions. A nested reaction was performed with 1 ul of the initial reaction, 10 pmol of nested primer RO1239 and 30 pmol of the GENRACER® nested 5 prime primer (SEQ ID NO:32) (5'- GGA CAC TGA CAT GGA CTG AAG GAG TA-3') or GeneRacer® nested 3 prime primer (SEQ ID NO:33) (5'-CGC TAC GTA ACG GCA TGA CAG TG -3') and nested primer RO1237 using the same conditions as the first reaction. Agarose gel analysis of the PCR products showed a band around 800 base pairs for the 5 prime reaction and approximately 600 base pairs for the 3 prime reaction. Subsequent cloning into pCR Blunt (Invitrogen, Carlsbad, Calif.), transformation into Top10 competent cells (Invitrogen, Carlsbad, Calif.), and sequencing revealed an open reading frame with both a start and stop codon. Primers RO1241 (SEQ ID NO:34) (5'-GAT ATC GAA TTC ATG ACG GTG GGC GGC GAT GAG G-3') and RO1242 (SEQ ID NO:35) (5'-GTA CTT AAG CTT TCA CTT GGA CTT GGG GTG GTC C-3') with restrictions sites added for cloning (see underlined EcoRI, and HindIII respectively) were used to isolate a full length gene. As shown above, 10 pmol of primers RO1241 and 1242 were used with TAQ® PCRx (Clonetech, Palo Alto, Calif.) using MgSO$_4$ according to the manufacturer's protocol with 2 ul of the cDNA as target. The thermocycling parameters were as follows: initial melt at 94° C. for 2 minutes followed by 5 cycles of 94° C. for 30 seconds and 72° C. for 2 minutes, 5 cycles of 94° C. 30 seconds, 70° C. for 2 minutes and 20 cycles of 94° C. for 30 seconds, 65° C. for 30 seconds and 68° C. for 2 minutes, followed by an extension of 68° C. for 10 minutes. The large product of the reaction was gel purified using the QIAQUICK gel purification kit (Qiagen, Valencia, Calif.) cut with EcoRI and HindIII and ligated to pYX242 EcoRI/ HindIII linearized DNA with the Rapid ligation kit (Roche, Indianapolis, Ind.) and designated pRSA-1. The clone pRSA1 contained a full length gene of 1530 bp (SEQ ID NO:36, FIG. 16) and an open reading frame of 509 amino acids (SEQ IN NO:37, FIG. 17). (Plasmid pRSA-1 was deposited with the American Type Culture Collection, 10801 University Boulevard, Manassas, Va. 20110 on Mar. 27, 2002 and was accorded accession number PTA-4186.)

The second Δ4-desaturase was identified by a partial sequence isolated using the primer combination of RO1201 (SEQ ID NO:38) (5'-CGT GTT CGC TGC CTT TGT CGG AAC TTG CAT CC- 3' and RO1202 (SEQ ID NO:39) (5'-TTG ACA ATA AAC ATG GAG GCG AGG ACC TCT CCG- 3') based on the sequence of pRTA7 (SEQ IN NO:16) as described in Example III. The genomic DNA (gDNA), was prepared as described in Example I, from *Thraustochytrium aureum* (BICC 7091) (Biocon India Ltd., Bangalore, India). PCR amplification was carried out in a 100 μl volume containing: 5 μl of isolated T7091 gDNA, 1.0 U of cDNA Polymerase (Clonetech, PaloAlto, Calif.) and 10 pMol of primers according the manufacturer's protocol. Thermocycler conditions in Perkin Elmer 9600 were as follows: 94° C. for 3 min, then 35 cycles of 94 ° C. for 30 sec., 60° C. for 30 sec., and 72° C. for 1 min. PCR was followed by an additional extension at 72° C. for 7 minutes. A 600 bp fragment was gel purified, ends filled-in using T4 DNA Polymerase (LifeTechnologies, Rockville, Md., cloned into the pCR-Blunt vector (Invitrogen, Co., Carlsbad, Calif.), and the recombinant plasmids transformed into TOP10 supercompetent cells (Invitrogen, Carlsbad, Calif.). Sequencing of the clones revealed high homology with pRTA7 (82.1% in 196 amino acids).

For isolation of a full-length gene, a cDNA library was constructed with mRNA isolated from total RNA using oligo dT cellulose resin. The pBluescript II XR library construction kit (Stratagene, La Jolla, Calif.) was then used to synthesize double stranded cDNA which was then directionally cloned (5'NotI/3'EcoRI) into pBluescript II KS(+) vector. The *T. aureum* (BICC 7091) library contained approximately 1.89×10$^8$ clones, each with an average insert size of approximately 1300 bp.

Primers RO1210 (SEQ ID NO:40) (5'-GCT GGT TGG ACT TTG GAC ATG ATT GGA TCC- 3') and RO1211 (SEQ ID NO:41) (5'-TAC ATT GGC AGG CCA ACC ATG TAG AGA ACG-3') were designed to amplify 5' and 3' sequences, respectively. RO1210/RO899 (SEQ ID NO:11) and RO1211/RO898(SEQ ID NO:7) were set up with cDNA Polymerase (Clonetech, PaloAlto, Calif.), 5 ul of cDNA from the library under the same conditions as described for isolating the original fragment earlier in this example. After cloning and sequencing of fragments an additional internal primer RO1214 (SEQ ID NO:42) (5'-GGA TTC AAT CAT GTC CAA AGT CCA ACC AGC-3') with RO898 from the vector was used to identify the 5' end of the gene. In a 50 μl reaction, 10 pmol of each primer with 5 ul of library DNA as target with Platinum Taq® PCRx (Clonetech, PaloAlto, Calif.) with MgSO$_4$ was used according to the manufacturer's protocol. The cycling protocol was as follows: an initial melt of 94° C. for 5 minutes followed by 35 cycles of 94° C. for 45 seconds, 55° C. for 30 seconds, 68° C. for 2 minutes and an extension cycle of 72° C. for 7 minutes.

The full-length Δ4-desaturase from *T. aureum* (BICC 7091) was isolated with 5' primer RO1223 (SEQ ID NO:43) (5'-TCT GAT GAA TTC ATG ACG GCC GGA TTT GAA GAA G-3') and 3' primer RO1224 (SEQ ID NO:44) (5'-GTC TAG CTC GAG TTA GTT CTT GTC CCA GGC AGG CA-3') with added restriction sites EcoRI and XhoI (underlined), respectively, added for cloning purposes. In a 50 μl reaction, 10 pmol of each primer, with 5 ul of library DNA as target, with Platinum Taq® PCRx (Clonetech, PaloAlto, Calif.) with MgSO$_4$ according to the manufacturer's protocol, were used. The cycling protocol was as follows: an initial melt of 94° C. for 5 minutes followed by 35 cycles of 94° C. for 45 seconds, 55° C. for 30 seconds, 68° C. for 2 minutes and an extension cycle of 72° C. for 7 minutes. The single band was separated on an agarose gel, purified, cut with EcoRI and XhoI, and ligated to pYX242 linearized with the same enzymes. Sequence analysis of the full-length clone designated, pRTA11 (see FIG. 18) (SEQ ID NO:45) revealed an open reading frame of 1542 base pairs encoding a protein of 513 amino acids (see FIG. 19) (SEQ ID NO:46). (Plasmid pRTA11 was deposited with the American Type Culture Collection, 10801 University Boulevard, Manassas, Va. 20110 on Mar. 27, 2002 and was accorded accession numbers PTA-4187.)

EXAMPLE VIII

Expression of Putative Δ4-Desaturases pRSA1 and pRTA11 in Yeast

Both plasmids were transformed into competent *Saccharomyces cerevisiae* strain 334 and grown as described in Example IV with either 50 μM ADA or ω3-DPA. As shown in Table 4, both ω6-DPA and DHA were produced when 334 (pRSA1) or (pRTA11) was grown with ADA or ω3-DPA, which are the products of a Δ4-desaturation.

TABLE 4

Fatty Acid as a Percentage of Total Lipid Extracted from Yeast

| Clone | 22:4(n – 6) Incorporated | 22:5(n – 6) Produced | 22:5(n – 3) Incorporated | 22:6(n – 3) Produced |
|---|---|---|---|---|
| PYX242 (control) | 15.03 | 0 | 20.46 | 0.25 |
| PYX242 (control) | 55.36 | 0 | 62.98 | 0.42 |
| PRTA11 | 50.73 | 5.42 | 42.39 | 9.17 |

Key:
22:4(n – 6) = Adrenic acid
22:5(n – 3) = ω3-Docosapentaenoic acid
22:5(n – 6) = ω6-Docosapentaenoic acid
22:6(n – 3) = Docosahexaenoic acid When the percent conversion of the substrate to product was calculated as described in Table 5, the preferred substrate, by virtue of the higher percent conversion, was the ω3-DPA to produce DHA. This data shows clearly that these plasmids also encode Δ4-desaturases.

TABLE 5

Percent Conversion of Two Substrates to Product

| Clone | 50 uM 22:4n – 6 | 50 uM 22:5n – 3 |
|---|---|---|
| PYX242 (control) | 0 | 1.2 |
| PRSA1 | 3.64 | 9.7 |
| PYX242 (control) | 0 | 0.66 |
| PRTA11 | 9.65 | 17.78 |

22:4n – 6 to 22:5n – 6 (Adrenic acid to ω6-Docosapentaenoic acid)
22:5n – 3 to 22:6n – 3 (ω3-Docosapentaenoic acid to Docosahexaenoic acid)

EXAMPLE IX

Demonstration of Co-expression of a Δ4-desaturase with a Mouse Elongase in Yeast As described in Example V, the *T.aureum* (ATCC 34304) Δ4-desaturase was co-transformed with the mouse elongase pRMELO4 (recloned from the plasmid pRAE84 into pYES2).

Table 6 shows that when 10 μM of the substrate EPA (20:5n-3) was added, the elongase was able to add two carbons to EPA to produce ω3-DPA, and the desaturase converted ω3-DPA to DHA. No DHA was produced by the control transformation 334(pYX242/pYES2). A small amount of ω3-DPA was seen in the control, but was a contaminant of the added substrate EPA. Thus, *T. aureum* Δ4-desaturase was able to produce a product in a heterologous expression system that was the product of another heterologous enzyme (the mouse elongase) from the PUFA biosynthetic pathway to produce the expected PUFA. This demonstrates that Δ4-desaturase can indeed work with other heterologous enzymes in the PUFA pathway in a heterologous expression system such as yeast.

TABLE 6

Fatty Acid (μg) Extracted Lipid from Yeast

| Clone | EPA Incorporated | ω3-DPA Produced by elongase | DHA Produced by desaturase |
|---|---|---|---|
| PYX242/ PYES2 (control) | 59.38 | 2.54 | 0 |
| PRTA7/ PRMELO4 (mouse elongase) | 47.04 | 14.76 | 1.55 |

10 μM substrate added

10 μM substrate added

EXAMPLE IX

Isolation of a Novel Desaturase Gene from the Algae *Isochrysis galbana* (CCMP1323)

The fatty acid composition of the algae *Isochrysis galbana* (*I. galbana*) (CCMP 1323) was investigated to determine the polyunsaturated fatty acids (PUFAs) produced by this organism. This algae showed a substantial amount of long chain PUFA including omega 3-docosapentaenoic acid (omega 3-DPA, 22:5n-3) and docosahexaenoic acid (DHA, 22:6n-3). In fact DHA was present in the highest amount representing 19% of the total lipid. Thus, *I. galbana* was predicted to possess a Δ4-desaturase capable of converting omega 3-DPA to DHA. The goal was therefore to isolate the predicted Δ4-desaturase gene from *I. galbana*, and to verify the functionality of the enzyme by expression in an alternate host.

Frozen pellets of *I. galbana* were obtained from Provasoli-Guillard National Center for Culture of Marine Phytoplankton (CCMP, West Boothbay Harbor, Me.). These pellets were crushed in liquid nitrogen and total RNA was extracted from *I. galbana* by using the QIAGEN RNEASY MAXI Kit (Qiagen, as per manufacturers instructions. From this total RNA, mRNA was isolated using oligo dT cellulose resin, which was then used for the construction of a cDNA library using the pBluescript II XR library construction kit (Stratagene, La Jolla, Calif.). The cDNA thus produced was directionally cloned (5'NotI/3'EcoRI) into pBluescript II KS (+) vector. The *I. galbana* library contained approximately $9.4 \times 10^4$ clones per μl, each with an average insert size of approximately 1300 bp. Two thousand primary clones from this library were sequenced from the 5' end using the M13 forward primer (SEQ NO ID:47) (5'-AGC GGA TAA CAA TTT CAC ACA GG-3'). Sequencing was carried out using the ABI BIGDYE sequencing kit (Applied Biosystems, Calif.) and the MEGABASE Capillary DNA sequencer (Amersham biosciences, Piscataway, N.J.).

A 647 bp clone containing the 3' end of this novel Δ4-desaturase designated 'iso25-A09' was obtained from sequencing of the 2000 library clones. This fragment shared ~30% amino acid sequence identity with other known delta 5 and delta 6 desaturases. Since this fragment did not contain the stop codon of the gene, additional clones containing the 3' end of this gene were obtained by PCR amplification of the cDNA library (template) using the 3'-end vector primer RO899 (SEQ ID NO:11) and RO1270 (SEQ ID NO:48) (5'-CAC CTG GCT CGA GTC GAC GAT GAT GG -3'). PCR amplification was carried out using Platinum Taq (HF) DNA polymerase (Invitrogen, Carlsbad, Calif.). Amplification was carried out in a 50 μl total volume containing: 1 μl of the cDNA library ligation mixture, PCR buffer containing 20 mM Tris-Cl, pH 8.4, 50 mM KCl (final concentration), 20 mM each deoxyribonucleotide triphosphate, 10 pmole of each primer, 1.5 mM MgSO₄, and 0.5 μl of Platinum Taq (HF) DNA polymerase. Amplification was carried out as follows using the Perkin Elmer 9600 machine: initial melt at 94° C. for 2 minutes followed by 5 cycles of 94° C. for 30 seconds and 72° C. for 3 minutes, 10 cycles of 94° C. 30 seconds, 70° C. for 30 seconds, and 72° C. for 3 minutes and 20 cycles of 94° C. for 30 seconds, 68° C. for 30 seconds and 72° C. for 3 minutes, followed by an extension of 72° C. for 10 minutes. From this amplification no bands were visible which might have been due to the low amounts of this gene in the library. Thus 2 μl of this PCR reaction was used as a template for a second PCR reaction involving Platinum Taq (HF) DNA polymerase under that same PCR components as described above. However, this time amplification was carried out as follows: initial denaturation at 94° C. for 3 minute, followed by 30 cycles of the following: 94° C. for 45 sec, 55° C. for 30 sec, 68° C. for 2 min. The reaction was terminated at 4° C. A 670 bp PCR band was thus obtained which was gel purified, and cloned into PCR-Blunt vector (Invitrogen, Carlsbad, Calif.). The recombinant plasmids were transformed into TOP10 supercompetent cells (Invitrogen, Carlsbad, Calif.), and clones were sequenced and analyzed. Clones 'iso25-Δ09-6' and iso25-A09-1' were thus obtained that contained the 3' end of the gene along with the 'TAA' stop codon and the poly-A tail. This clone did overlap with the original 'iso25-A09' fragment.

To isolate the 5' end of this gene, RACE (rapid amplification of cDNA ends) ready cDNA was used as a target for the reactions. To prepare this material, approximately 5 μg of total RNA was used according the manufacturer's direction with the GENRACER™ kit (Invitrogen, Carlsbad, Calif.) and SUPERSCRIPT II™ enzyme (Invitrogen, Carlsbad, Calif.) for reverse transcription to produce cDNA target. This cDNA was then used as a template for a PCR reaction involving 30 pmol GENRACER™ 5' primer (SEQ ID NO:30) (5'-CGA CTG GAG CAC GAG GAC ACT GA-3') in combination with 10 pmols of any one of the following gene-specific primers:

```
RO1286                          (SEQ ID NO:49)
5'- CGT ACC CGG TGC AAT AGA AGG TGA G -3'

RO1287                          (SEQ ID NO:50)
5'- CCA TCA TCG TCG ACT CGA GCC AGC TG -3'

RO1288                          (SEQ ID NO:51)
5'- TGT GGA GCC ATG TGG TGC TCG ATC TG -3'

RO1271                          (SEQ ID NO:52)
5'- TGT GGA GCC ATG TGG TGC TCG ATC TG -3'
```

PCR amplification was carried out using Platinum Taq DNA polymerase (Invitrogen, Carlsbad, Calif.) in a 50 μl total volume containing: 1 μl of the RACE-cDNA, PCR buffer containing 20 mM Tris-Cl, pH 8.4, 50 mM KCl (final concentration), 200 μM each deoxyribonucleotide triphosphate, 1.5 mM MgSO₄, and 0.5 μl of Platinum Taq DNA polymerase. Amplification was carried out as follows using the Perkin Elmer 9600 machine: initial melt at 94° C. for 2 minutes followed by 5 cycles of 94° C. for 30 seconds and 72° C. for 3 minutes, 10 cycles of 94° C. 30 seconds, 70° C. for 30 seconds, and 72° C. for 3 minutes and 20 cycles of 94° C. for 30 seconds, 68° C. for 30 seconds and 72° C. for 3 minutes, followed by an extension of 72° C. for 10 minutes. All these primer combinations resulted in bands, which were gel purified, filled-in with T4-DNA polymerase, cloned into PCR-blunt vector and transformed into TOP 10 supercompetent cells. Sequencing of these clones like 'iso25-A09-33-5', 'iso25-A09-31-3', iso25-A09-30-1' and iso25-A09-32-3' revealed the 5' end of this gene containing the 'ATG' start site, the cytochrome b5 domain and two histidine boxes. These clones overlapped each other and also overlapped the original 'iso25-A09' fragment that contained the third histidine box.

To isolate the full length of this gene both genomic DNA, as well as cDNA obtained (from RACE), were used as templates in PCR reactions with the following primers:

```
RO 1400
5'- TCA ACA GAA TTC ATG TGC AAC GCG GCG CAG GTC GAG ACG CAG -3'  (SEQ ID NO:53)
```

(This forward primer contained an EcoRI site (underlined) along with the 'ATG' start site (bold) suitable for cloning into the yeast expression vector pYX242).

```
RO 1401
5'- AAA AGA AAG CTT TTA GTC CGC CTT GAC CGT GTC GAC CAA AGC -3'  (SEQ ID NO:54)
```

(This reverse primer contained a HindIII site (underlined) along with the 'TAA' stop site (bold) for cloning into pYX242). PCR amplification was carried out using Advantage-GC cDNA polymerase (Clonetech, Palo Alto, Calif.) in a 50 µl total volume containing: 1 µl of the RACE-cDNA or 2 µl of genomic DNA, PCR buffer containing [40 mM Tricine-KOH pH 9.2, 15 mM KOAc (final concentration), 3.5 mM Mg(OAc)$_2$, 5% DMSO, 3.75 µg/ml BSA, 200 µM each deoxyribonucleotide triphosphate, 1 M GC-melt, and 1 µl of Advantage-GC cDNA polymerase. The thermocycling protocol included an initial denaturation at 94° C. for 1 mm, followed by 30 cycles of the following a final extension at 68° C. for 5 minutes, followed by termination at 4° C.

A ~1.35 kb band was obtained which was gel purified, digested with the restriction enzymes EcoRI/HindIII for 2 hours, cleaned through the QiaQuick PCR purification kit (Qiagen, Valencia, Calif.), and cloned into the pYX242 yeast expression vector (Novagen, Madison, Wis.) previously digested with EcoRI/HindIII. This construct was labeled pRIG6 and consisted of the 'iso25-A09' full length gene isolated from RACE-derived cDNA and the pYX242 vector. This was transformed into yeast SC334 for expression studies.

The full length gene of 'iso25-A09' present in pRIG6 was 1302 bp in length (SEQ ID NO:54) (FIG. 20) and encoded a protein of 433 amino acids (SEQ ID NO:55) (FIG. 21). A tFastA search of the deduced protein sequence of this gene showed the protein to have 30.6% identity with the Δ5-desaturase from *I. galbana* (U.S. patent application Ser. No. 10/054,534 incorporated in its entirety by reference). Also, the predicted protein of this gene was 30.8% identical to the Δ4-desaturase from *Thraustochytrium aureum* (ATCC 34304)(FIG. 22). (Further, the DNA sequence of the gene was found to exhibit 42.3 7% sequence identity to the nucleotide sequence encoding the *T. aureum* (ATCC 34304)) Δ4-desaturase, 43% identity to the nucleotide sequence encoding the *S. aggregatum* (ATCC 28209) Δ4-desaturase, and 39.7% identity to the nucleotide sequence encoding the *T. aureum* (BICC7O91) Δ4-desaturase sequence.) Like all front-end desaturating enzyme genes like Δ5- and Δ6-desaturase, this gene contains a cytochrome b5 domain within the 5'-end of its sequence. This cytochrome b5 is thought to function as the immediate electron donor for the desaturases, and functions in a number of oxidation-reduction reactions involving NADH-dependent desaturation. This gene also possessed the three histidine-rich motifs that are present in all membrane-bound desaturases. These are present at position 153 to 158 (HMGGH) (SEQ ID NO:71), 188 to 193 (HNKHH) (SEQ ID NO:72), and 347 to 352 (QIEHH) (SEQ ID NO:73). These histidine-rich boxes are believed to co-ordinate the diiron-oxo structure at the enzyme's active site, and are necessary for enzyme activity. These features are consistent with this gene product being a member of the membrane-bound desaturase/hydroxylase family of the diiron-oxo proteins (3) and also being a front-end desaturating enzyme. The G+C content of this gene is 64.2%.

EXAMPLE X

Expression of pRIG6, a Novel Desaturase from *Isochrysis galbana* (CCMP 1323), in Yeast To determine the substrate specificity and the class of reaction catalyzed by a novel desaturase from *I. galbana*, the pRIG6 construct was heterologously expressed in a *Saccharomyces cerevisiae* (SC334), as described below. Since *S. cerevisiae* cannot synthesize fatty acids beyond oleic acid (OA, 18:1 n-9), it is an ideal system to use to determine enzyme activity on substrates longer than OA since no background enzyme activity will be detected. Here, substrates can be exogenously supplied to the host, taken up by the cell and acted on by the expressed protein of the transformed gene.

Clone pRIG6, which consisted of the full-length 'iso25-A09' desaturase from *I. galbana* cloned into pYX242, was transformed into *Saccharomyces cerevisiae* (SC334) using the Alkali-Cation Yeast Transformation kit (BIO 101, Vista, Calif.). Transformants were selected for leucine auxotrophy on media lacking leucine (DOB [-Leu]). To detect the specific desaturase activity of these clones, transformants were grown in the presence of 50 µM specific fatty acid substrates as listed below:

a. Linoleic acid (LA, 18:2n-6)-conversion to α-linolenic acid (ALA, 18:3n-3) indicates Δ15-desaturase activity; conversion to gamma-linolenic acid indicates Δ6-desaturase activity.

b. Dihomo-gamma-linolenic acid (20:3n-6)- conversion to eicosatetraenoic acid (ETA, 20:4n-3) indicates Δ17-desaturase activity; conversion to arachidonic acid (ARA, 20:4n-6) indicates Δ5-desaturase activity.

c. Omega-6-eicosadienoic acid (20:2n-6)-conversion to Dihomo-gamma-linolenic acid (20:3n-6) indicates Δ8-desaturase activity.

d. Adrenic acid (22:4n-6)-conversion to ω6-docosapentaenoic acid (22:5n-6) indicates Δ4-desaturase activity.

e. Omega 3-docosapentaenoic acid (22:5n-3)-conversion to Docosahexaenoic acid (22:6n-3) indicates Δ4-desaturase activity.

The negative control strain consisted of S. cerevisiae transformed with the pYX242 vector, and these cultures were grown simultaneously and analyzed.

The cultures were vigorously agitated (250 rpm) and grown for 48 hours a 24° C. in the presence of 50 μM (final concentration) of the various substrates (Table 7). The cells were spun down, washed once in distilled water, and the pellets vortexed in methanol; chloroform was added along with tridecanoin (as an internal standard). These mixtures were incubated for at least an hour at room temperature, or at 4° C. overnight. The chloroform layer was extracted and filtered through a Whatman filter with 1 gm anhydrous sodium sulfate to remove particulates and residual water. The organic solvents were evaporated at 40° C. under a stream of nitrogen. The extracted lipids were then derivitized to fatty acid methyl esters (FAME) for gas chromatography analysis (GC) by adding 2 ml 0.5 N potassium hydroxide in methanol to a closed tube. The samples were heated to 95° C.–100° C. for 30 minutes and cooled to room temperature. Approximately 2 ml 14% borontrifluoride in methanol was added and the heating repeated. After the extracted lipid mixture cooled, 2 ml of water and 1 ml of hexane were added to extract the FAME for analysis by GC. The percent conversion was calculated using the formula:

$$\% \text{ Conversion} = \frac{[\% \text{ Product}]}{[\% \text{ Product} + \% \text{ Substrate}]} \times 100$$

Table 7 shows the substrate specificity of the novel desaturase expressed in yeast. Here, the expressed pRIG6 clone was capable of converting 15.3% of ω3-docosapentaenoic acid (22:5n-3) to docosahexaenoic acid (22:5 n-3), indicating that the gene was a Δ4-desaturase. In addition, this enzyme was capable of converting 11% of adrenic acid (22:4n-6) to ω6-docosapentaenoic acid (22:5n-6), which also indicated Δ4-desaturase activity.

The fatty acids of interest are represented as a percentage of the total lipids extracted from yeast. GC/MS was employed to identify the products. Under these conditions, the clones did not exhibit other desaturase activities. This confirmed the gene isolated to be a novel Δ4-desaturase gene. No background substrate conversion was detected with using just the vector alone. This data indicates that this novel Δ4-desaturase can be expressed in a heterologous system and would thus be useful in the production of transgenic oil containing DHA.

TABLE 7

Isochrysis galbana (CCMP 1323) Delta 4-Desaturase Expression in Baker's Yeast at 24° C.

| Clone | Desaturase activity | Substrate* Incorpor. | Substrate Produced | % Conversion of Substrate |
|---|---|---|---|---|
| pRIG6 | Δ6 | LA (8.35%) | GLA (0%) | 0 |
| (pYX242 + Delta 4) | Δ5 | DGLA (16.34%) | AA (0.29%) | 0 |
|  | Δ8 | ω6-EDA (19.53%) | DGLA (0%) | 0 |
|  | Δ4 | ADA (23.93%) | ω6-DPA (3.15%) | 11% |
|  | Δ4 | ω3-DPA (32.57%) | DHA (5.89%) | 15.3% |

TABLE 7-continued

Isochrysis galbana (CCMP 1323) Delta 4-Desaturase Expression in Baker's Yeast at 24° C.

| Clone | Desaturase activity | Substrate* Incorpor. | Substrate Produced | % Conversion of Substrate |
|---|---|---|---|---|
| Control (pYX242) | Δ6 | LA (9.18%) | GLA (0%) | 0 |
|  | Δ5 | DGLA (10.5%) | AA (0%) | 0 |
|  | Δ8 | ω6-EDA (16.56%) | DGLA (0%) | 0 |
|  | Δ4 | ADA (15.55%) | ω6-DPA (0%) | 0 |
|  | Δ4 | ω3-DPA (26.03%) | DHA (0.29%) | 0 |

*50 μM substrate used
Numbers in parenthesis represent fatty acid as a percentage of total lipids from yeast
Key:
LA = Linoleic acid (18:2n − 6)
GLA = Gamma-linolenic acid (18:3n − 6)
DGLA = Dihomo-gamma-linolenic acid (20:3n − 6)
AA = Arachidonic acid (20:4n − 6)
ω6-EDA = omega-6 Eicosadienoic acid (20:2n − 6)
ADA = Adrenic acid (22:4n − 6)
ω3-DPA = omega-3 Docosapentaenoic acid (22:5n − 6)
ω6-DPA = omega-6 Docosapentaenoic acid (22:5n − 3)
DHA = Docosahexaenoic acid (22:6n − 3)

Nutritional Compositions

The PUFAs described in the Detailed Description may be utilized in various nutritional supplements, infant formulations, nutritional substitutes and other nutritional solutions.

I. Infant Formulations

A. ISOMIL® Soy Formula with Iron

Usage: As a beverage for infants, children and adults with an allergy or sensitivity to cows milk. A feeding for patients with disorders for which lactose should be avoided: lactase deficiency, lactose intolerance and galactosemia.

Features:
Soy protein isolate to avoid symptoms of cow's-milk-protein allergy or sensitivity.
Lactose-free formulation to avoid lactose-associated diarrhea.
Low osmolality (240 mOs/kg water) to reduce risk of osmotic diarrhea.
Dual carbohydrates (corn syrup and sucrose) designed to enhance carbohydrate absorption and reduce the risk of exceeding the absorptive capacity of the damaged gut.
1.8 mg of Iron (as ferrous sulfate) per 100 Calories to help prevent iron deficiency.
Recommended levels of vitamins and minerals.
Vegetable oils to provide recommended levels of essential fatty acids.
Milk-white color, milk-like consistency and pleasant aroma.

Ingredients: (Pareve) 85% water, 4.9% corn syrup, 2.6% sugar (sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and disglycerides, soy lecithin, carrageenan, ascorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

B. ISOMIL® DF Soy Formula For Diarrhea

Usage: As a short-term feeding for the dietary management of diarrhea in infants and toddlers.

Features:

First infant formula to contain added dietary fiber from soy fiber specifically for diarrhea management.

Clinically shown to reduce the duration of loose, watery stools during mild to severe diarrhea in infants.

Nutritionally complete to meet the nutritional needs of the infant.

Soy protein isolate with added L-methionine meets or exceeds an infant's requirement for all essential amino acids.

Lactose-free formulation to avoid lactose-associated diarrhea.

Low osmolality (240 mOsm/kg water) to reduce the risk of osmotic diarrhea.

Dual carbohydrates (corn syrup and sucrose) designed to enhance carbohydrate absorption and reduce the risk of exceeding the absorptive capacity of the damaged gut.

Meets or exceeds the vitamin and mineral levels recommended by the Committee on Nutrition of the American Academy of Pediatrics and required by the Infant Formula Act.

1.8 mg of iron (as ferrous sulfate) per 100 Calories to help prevent iron deficiency.

Vegetable oils to provide recommended levels of essential fatty acids.

Ingredients: (Pareve) 86% water, 4.8% corn syrup, 2.5% sugar (sucrose), 2.1% soy oil, 2.0% soy protein isolate, 1.4% coconut oil, 0.77% soy fiber, 0.12% calcium citrate, 0.11% calcium phosphate tribasic, 0.10% potassium citrate, potassium chloride, potassium phosphate monobasic, mono and diglycerides, soy lecithin, carrageenan, magnesium chloride, ascorbic acid, L-methionine, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

C. ISOMIL® SF Sucrose-Free Soy Formula With Iron

Usage: As a beverage for infants, children and adults with an allergy or sensitivity to cow's-milk protein or an intolerance to sucrose. A feeding for patients with disorders for which lactose and sucrose should be avoided.

Features:

Soy protein isolate to avoid symptoms of cow's-milk-protein allergy or sensitivity.

Lactose-free formulation to avoid lactose-associated diarrhea (carbohydrate source is Polycose® Glucose Polymers).

Sucrose free for the patient who cannot tolerate sucrose.

Low osmolality (180 mOsm/kg water) to reduce risk of osmotic diarrhea.

1.8 mg of iron (as ferrous sulfate) per 100 Calories to help prevent iron deficiency.

Recommended levels of vitamins and minerals.

Vegetable oils to provide recommended levels of essential fatty acids.

Milk-white color, milk-like consistency and pleasant aroma.

Ingredients: (Pareve) 75% water, 11.8% hydrolized cornstarch, 4.1% soy oil, 4.1% soy protein isolate, 2.8% coconut oil, 1.0% modified cornstarch, 0.38% calcium phosphate tribasic, 0.17% potassium citrate, 0.13% potassium chloride, mono- and diglycerides, soy lecithin, magnesium chloride, abscorbic acid, L-methionine, calcium carbonate, sodium chloride, choline chloride, carrageenan, taurine, ferrous sulfate, m-inositol, alpha-tocopheryl acetate, zinc sulfate,L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

D. ISOMIL® 20 Soy Formula With Iron Ready To Feed, 20 Cal/fl oz.

Usage: When a soy feeding is desired.

Ingredients: (Pareve) 85% water, 4.9% corn syrup, 2.6% sugar(sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and diglycerides, soy lecithin, carrageenan, abscorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

E. SIMILAC® Infant Formula

Usage: When an infant formula is needed: if the decision is made to discontinue breastfeeding before age 1 year, if a supplement to breastfeeding is needed or as a routine feeding if breastfeeding is not adopted.

Features:

Protein of appropriate quality and quantity for good growth; heat-denatured, which reduces the risk of milk-associated enteric blood loss.

Fat from a blend of vegetable oils (doubly homogenized), providing essential linoleic acid that is easily absorbed.

Carbohydrate as lactose in proportion similar to that of human milk.

Low renal solute load to minimize stress on developing organs.

Powder, Concentrated Liquid and Ready To Feed forms.

Ingredients: (–D) Water, nonfat milk, lactose, soy oil, coconut oil, mono- and diglycerides, soy lecithin, abscorbic acid, carrageenan, choline chloride, taurine, m-inositol, alpha-tocopheryl acetate, zinc sulfate, niacinamide, ferrous sulfate, calcium pantothenate, cupric sulfate, vitamin A palmitate, thiamine chloride hydrochloride, riboflavin, pyridoxine hydrochloride, folic acid, manganese sulfate, phylloquinone, biotin, sodium selenite, vitamin D3 and cyanocobalamin.

F. SIMILAC® NeoCare Premature Infant Formula with Iron

Usage: For premature infants' special nutritional needs after hospital discharge. Similac NeoCare is a nutritionally complete formula developed to provide premature infants with extra calories, protein, vitamins and minerals needed to promote catch-up growth and support development.

Features:
Reduces the need for caloric and vitamin supplementation. More calories (22 Cal/fl oz) than standard term formulas (20 Cal/fl oz).
Highly absorbed fat blend, with medium-chain triglycerides (MCToil) to help meet the special digestive needs of premature infants.
Higher levels of protein, vitamins and minerals per 100 calories to extend the nutritional support initiated in-hospital.
More calcium and phosphorus for improved bone mineralization.

Ingredients: -D Corn syrup solids, nonfat milk, lactose, whey protein concentrate, soy oil, high-oleic safflower oil, fractionated coconut oil (medium chain triglycerides), coconut oil, potassium citrate, calcium phosphate tribasic, calcium carbonate, ascorbic acid, magnesium chloride, potassium chloride, sodium chloride, taurine, ferrous sulfate, m-inositol, choline chloride, ascorbyl palmitate, L-carnitine, alpha-tocopheryl acetate, zinc sulfate, niacinamide, mixed tocopherols, sodium citrate, calcium pantothenate, cupric sulfate, thiamine chloride hydrochloride, vitamin A palmitate, beta carotene, riboflavin, pyridoxine hydrochloride, folic acid, manganese sulfate, phylloquinone, biotin, sodium selenite, vitamin D3 and cyanocobalamin.

G. SIMILAC® Natural Care Low-Iron Human Milk Fortifier Ready To Use, 24 Cal/fl oz.

Usage: Designed to be mixed with human milk or to be fed alternatively with human milk to low-birth-weight infants.

Ingredients: -D Water, nonfat milk, hydrolyzed cornstarch, lactose, fractionated coconut oil (medium-chain triglycerides), whey protein concentrate, soy oil, coconut oil, calcium phosphate tribasic, potassium citrate, magnesium chloride, sodium citrate, ascorbic acid, calcium carbonate, mono and diglycerides, soy lecithin, carrageenan, choline chloride, m-inositol, taurine, niacinamide, L-carnitine, alpha tocopheryl acetate, zinc sulfate, potassium chloride, calcium pantothenate, ferrous sulfate, cupric sulfate, riboflavin, vitamin A palmitate, thiamine chloride hydrochloride, pyridoxine hydrochloride, biotin, folic acid, manganese sulfate, phylloquinone, vitamin D3, sodium selenite and cyanocobalamin.

Various PUFAs of this invention can be substituted and/or added to the infant formulae described above and to other infant formulae known to those in the art.

II. NUTRITIONAL FORMULATIONS

A. ENSURE®

Usage: ENSURE is a low-residue liquid food designed primarily as an oral nutritional supplement to be used with or between meals or, in appropriate amounts, as a meal replacement. ENSURE is lactose- and gluten-free, and is suitable for use in modified diets, including low-cholesterol diets. Although it is primarily an oral supplement, it can be fed by tube.

Patient Conditions:
For patients on modified diets
For elderly patients at nutrition risk
For patients with involuntary weight loss
For patients recovering from illness or surgery
For patients who need a low-residue diet
Ingredients: -D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate.

B. ENSURE® BARS

Usage: ENSURE BARS are complete, balanced nutrition for supplemental use between or with meals. They provide a delicious, nutrient-rich alternative to other snacks. ENSURE BARS contain <1 g lactose/bar, and Chocolate Fudge Brownie flavor is gluten-free. (Honey Graham Crunch flavor contains gluten.)

Patient Conditions:
For patients who need extra calories, protein, vitamins and minerals.
Especially useful for people who do not take in enough calories and nutrients.
For people who have the ability to chew and swallow
Not to be used by anyone with a peanut allergy or any type of allergy to nuts.

Ingredients: Honey Graham Crunch—High-Fructose Corn Syrup, Soy Protein Isolate, Brown Sugar, Honey, Maltodextrin (Corn), Crisp Rice (Milled Rice, Sugar [Sucrose], Salt [Sodium Chloride] and Malt), Oat Bran, Partially Hydrogenated Cottonseed and Soy Oils, Soy Polysaccharide, Glycerine, Whey Protein Concentrate, Polydextrose, Fructose, Calcium Caseinate, Cocoa Powder, Artificial Flavors, Canola Oil, High-Oleic Safflower Oil, Nonfat Dry Milk, Whey Powder, Soy Lecithin and Corn Oil. Manufactured in a facility that processes nuts.

Vitamins and Minerals: Calcium Phosphate Tribasic, Potassium Phosphate Dibasic, Magnesium Oxide, Salt (Sodium Chloride), Potassium Chloride, Ascorbic Acid, Ferric Orthophosphate, Alpha-Tocopheryl Acetate, Niacinamide, Zinc Oxide, Calcium Pantothenate, Copper Gluconate, Manganese Sulfate, Riboflavin, Beta Carotene, Pyridoxine Hydrochloride, Thiamine Mononitrate, Folic Acid, Biotin, Chromium Chloride, Potassium Iodide, Sodium Selenate, Sodium Molybdate, Phylloquinone, Vitamin D3 and Cyanocobalamin.

Protein: Honey Graham Crunch—The protein source is a blend of soy protein isolate and milk proteins.

| | |
|---|---|
| Soy protein isolate | 74% |
| Milk proteins | 26% |

Fat: Honey Graham Crunch—The fat source is a blend of partially hydrogenated cottonseed and soybean, canola, high oleic safflower, oils, and soy lecithin.

| | |
|---|---|
| Partially hydrogenated cottonseed and soybean oil | 76% |
| Canola oil | 8% |
| High-oleic safflower oil | 8% |
| Corn oil | 4% |
| Soy lecithin | 4% |

Carbohydrate: Honey Graham Crunch—The carbohydrate source is a combination of high-fructose corn syrup, brown sugar, maltodextrin, honey, crisp rice, glycerine, soy polysaccharide, and oat bran.

| | |
|---|---|
| High-fructose corn syrup | 24% |
| Brown sugar | 21% |
| Maltodextrin | 12% |
| Honey | 11% |
| Crisp rice | 9% |
| Glycerine | 9% |
| Soy Polysaccharide | 7% |
| Oat bran | 7% |

C. ENSURE® HIGH PROTEIN

Usage: ENSURE HIGH PROTEIN is a concentrated, high-protein liquid food designed for people who require additional calories, protein, vitamins, and minerals in their diets. It can be used as an oral nutritional supplement with or between meals or, in appropriate amounts, as a meal replacement. ENSURE HIGH PROTEIN is lactose- and gluten-free, and is suitable for use by people recovering from general surgery or hip fractures and by patients at risk for pressure ulcers.

Patient Conditions:
For patients who require additional calories, protein, vitamins, and minerals, such as patients recovering from general surgery or hip fractures, patients at risk for pressure ulcers, and patients on low-cholesterol diets.

Features:
Low in saturated fat
Contains 6 g of total fat and <5 mg of cholesterol per serving
Rich, creamy taste
Excellent source of protein, calcium, and other essential vitamins and minerals
For low-cholesterol diets
Lactose-free, easily digested Ingredients:
Vanilla Supreme: -D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate, Phylloquinone, Vitamin D3 and Cyanocobalamin.

Protein:
The protein source is a blend of two high-biologic-value proteins: casein and soy.

| | |
|---|---|
| Sodium and calcium caseinates | 85% |
| Soy protein isolate | 15% |

Fat:
The fat source is a blend of three oils: high-oleic safflower, canola, and soy.

| | |
|---|---|
| High-oleic safflower oil | 40% |
| Canola oil | 30% |
| Soy oil | 30% |

The level of fat in ENSURE HIGH PROTEIN meets American Heart Association (AHA) guidelines. The 6 grams of fat in ENSURE HIGH PROTEIN represent 24% of the total calories, with 2.6% of the fat being from saturated fatty acids and 7.9% from polyunsaturated fatty acids. These values are within the AHA guidelines of <30% of total calories from fat, <10% of the calories from saturated fatty acids, and <10% of total calories from polyunsaturated fatty acids.

Carbohydrate:
ENSURE HIGH PROTEIN contains a combination of maltodextrin and sucrose. The mild sweetness and flavor variety (vanilla supreme, chocolate royal, wild berry, and banana), plus VARI-FLAVORS® Flavor Pacs in pecan, cherry, strawberry, lemon, and orange, help to prevent flavor fatigue and aid in patient compliance.

| | |
|---|---|
| Vanilla and other nonchocolate flavors: | |
| Sucrose | 60% |
| Maltodextrin | 40% |
| Chocolate: | |
| Sucrose | 70% |
| Maltodextrin | 30% |

D. ENSURE® LIGHT

Usage: ENSURE LIGHT is a low-fat liquid food designed for use as an oral nutritional supplement with or between meals. ENSURE LIGHT is lactose- and gluten-free, and is suitable for use in modified diets, including low-cholesterol diets.

Patient Conditions:
For normal-weight or overweight patients who need extra nutrition in a supplement that contains 50% less fat and 20% fewer calories than ENSURE.
For healthy adults who do not eat right and need extra nutrition.

Features:
Low in fat and saturated fat
Contains 3 g of total fat per serving and <5 mg cholesterol
Rich, creamy taste
Excellent source of calcium and other essential vitamins and minerals
For low-cholesterol diets
Lactose-free, easily digested Ingredients:

French Vanilla: -D Water, Maltodextrin (Corn), Sugar (Sucrose), Calcium Caseinate, High-Oleic Safflower Oil, Canola Oil, Magnesium Chloride, Sodium Citrate, Potassium Citrate, Potassium Phosphate Dibasic, Magnesium Phosphate Dibasic, Natural and Artificial Flavor, Calcium Phosphate Tribasic, Cellulose Gel, Choline Chloride, Soy Lecithin, Carrageenan, Salt (Sodium Chloride), Ascorbic Acid, Cellulose Gum, Ferrous Sulfate, Alpha-Tocopheryl Acetate, Zinc Sulfate, Niacinamide, Manganese Sulfate, Calcium Pantothenate, Cupric Sulfate, Thiamine Chloride Hydrochloride, Vitamin A Palmitate, Pyridoxine Hydrochloride, Riboflavin, Chromium Chloride, Folic Acid, Sodium Molybdate, Biotin, Potassium Iodide, Sodium Selenate, Phylloquinone, Vitamin D3 and Cyanocobalamin.

Protein:

The protein source is calcium caseinate.

| | |
|---|---|
| Calcium caseinate | 100% |

Fat:

The fat source is a blend of two oils: high-oleic safflower and canola.

| | |
|---|---|
| High-oleic safflower oil | 70% |
| Canola oil | 30% |

The level of fat in ENSURE LIGHT meets American Heart Association (AHA) guidelines. The 3 grams of fat in ENSURE LIGHT represent 13.5% of the total calories, with 1.4% of the fat being from saturated fatty acids and 2.6% from polyunsaturated fatty acids. These values are within the AHA guidelines of <30% of total calories from fat, <10% of the, calories from saturated fatty acids, and <10% of total calories from polyunsaturated fatty acids.

Carbohydrate:

ENSURE LIGHT contains a combination of maltodextrin and sucrose. The chocolate flavor contains corn syrup as well. The mild sweetness and flavor variety (French vanilla, chocolate supreme, strawberry swirl), plus VARI-FLAVORS® Flavor Pacs in pecan, cherry, strawberry, lemon, and orange, help to prevent flavor fatigue and aid in patient compliance.

Vanilla and other nonchocolate flavors:

| | |
|---|---|
| Sucrose | 51% |
| Maltodextrin | 49% |

Chocolate:

| | |
|---|---|
| Sucrose | 47.0% |
| Corn Syrup | 26.5% |
| Maltodextrin | 26.5% |

Vitamins and Minerals:

An 8-fl-oz serving of ENSURE LIGHT provides at least 25% of the RDIs for 24 key vitamins and minerals.

Caffeine:

Chocolate flavor contains 2.1 mg caffeine/8 fl oz.

E. ENSURE PLUS®

Usage: ENSURE PLUS is a high-calorie, low-residue liquid food for use when extra calories and nutrients, but a normal concentration of protein, are needed. It is designed primarily as an oral nutritional supplement to be used with or between meals or, in appropriate amounts, as a meal replacement. ENSURE PLUS is lactose- and gluten-free. Although it is primarily an oral nutritional supplement, it can be fed by tube.

Patient Conditions:

For patients who require extra calories and nutrients, but a normal concentration of protein, in a limited volume.

For patients who need to gain or maintain healthy weight.

Features:

Rich, creamy taste

Good source of essential vitamins and minerals

Ingredients:

Vanilla: -D Water, Corn Syrup, Maltodextrin (Corn), Corn Oil, Sodium and Calcium Caseinates, Sugar 5 (Sucrose), Soy Protein Isolate, Magnesium Chloride, Potassium Citrate, Calcium Phosphate Tribasic, Soy Lecithin, Natural and Artificial Flavor, Sodium Citrate, Potassium Chloride, Choline Chloride, Ascorbic Acid, Carrageenan, Zinc Sulfate, Ferrous Sulfate, Alpha-Tocopheryl Acetate, Niacinamide, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

Protein:

The protein source is a blend of two high-biologic-value proteins: casein and soy.

| | |
|---|---|
| Sodium and calcium caseinates | 84% |
| Soy protein isolate | 16% |

Fat:

The fat source is corn oil.

| | |
|---|---|
| Corn oil | 100% |

Carbohydrate:

ENSURE PLUS contains a combination of maltodextrin and sucrose. The mild sweetness and flavor variety (vanilla, chocolate, strawberry, coffee, buffer pecan, and eggnog), plus VARI-FLAVORS® Flavor Pacs in pecan, cherry, strawberry, lemon, and orange, help to prevent flavor fatigue and aid in patient compliance.

Vanilla, strawberry, butter pecan, and coffee flavors:

Corn Syrup 39%

Maltodextrin 38%

Sucrose 23%

Chocolate and eggnog flavors:

Corn Syrup 36%

Maltodextrin 34%

Sucrose 30%

Vitamins and Minerals:
An 8-fl-oz serving of ENSURE PLUS provides at least 15% of the RDIs for 25 key Vitamins and minerals.

Caffeine:
Chocolate flavor contains 3.1 mg Caffeine/8 fl oz. Coffee flavor contains a trace amount of caffeine.

F. ENSURE PLUS® HN

Usage: ENSURE PLUS HN is a nutritionally complete high-calorie, high-nitrogen liquid food designed for people with higher calorie and protein needs or limited volume tolerance. It may be used for oral supplementation or for total nutritional support by tube. ENSURE PLUS HN is lactose- and gluten-free.

Patient Conditions:
For patients with increased calorie and protein needs, such as following surgery or injury.
For patients with limited volume tolerance and early satiety.

Features:
For supplemental or total nutrition
For oral or tube feeding
1.5 CaVmL,
High nitrogen
Calorically dense Ingredients:
Vanilla: −D Water, Maltodextrin (Corn), Sodium and Calcium Caseinates, Corn Oil, Sugar (Sucrose), Soy Protein Isolate, Magnesium Chloride, Potassium Citrate, Calcium Phosphate Tribasic, Soy Lecithin, Natural and Artificial Flavor, Sodium Citrate, Choline Chloride, Ascorbic Acid, Taurine, L-Carnitine, Zinc Sulfate, Ferrous Sulfate, Alpha-Tocopheryl Acetate, Niacinamide, Carrageenan, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

G. ENSURE® POWDER

Usage: ENSURE POWDER (reconstituted with water) is a low-residu liquid food designed primarily as an oral nutritional supplement to be used with or between meals. ENSURE POWDER is lactose- and gluten-free, and is suitable for use in modified diets, including low-cholesterol diets.

Patient Conditions:
For patients on modified diets
For elderly patients at nutrition risk
For patients recovering from illness/surgery
For patients who need a low-residue diet Features:
Convenient, easy to mix
Low in saturated fat
Contains 9 g of total fat and <5 mg of cholesterol per serving
High in vitamins and minerals
For low-cholesterol diets
Lactose-free, easily digested Ingredients: -D Corn Syrup, Maltodextrin (Corn), Sugar (Sucrose), Corn Oil, Sodium and Calcium Caseinates, Soy Protein Isolate, Artificial Flavor, Potassium Citrate, Magnesium Chloride, Sodium Citrate, Calcium Phosphate Tribasic, Potassium Chloride, Soy Lecithin, Ascorbic Acid, Choline Chloride, Zinc Sulfate, Ferrous Sulfate, Alpha-Tocopheryl Acetate, Niacinamide, Calcium Pantothenate, Manganese Sulfate, Thiamine Chloride Hydrochloride, Cupric Sulfate, Pyridoxine Hydrochloride, Riboflavin, Vitamin A Palmitate, Folic Acid, Biotin, Sodium Molybdate, Chromium Chloride, Potassium Iodide, Sodium Selenate, Phylloquinone, Vitamin D3 and Cyanocobalamin.

Protein:
The protein source is a blend of two high-biologic-value proteins: casein and soy.

| | |
|---|---|
| Sodium and calcium caseinates | 84% |
| Soy protein isolate | 16% |

Fat:
The fat source is corn oil.

| | |
|---|---|
| Corn oil | 100% |

Carbohydrate:
ENSURE POWDER contains a combination of corn syrup, maltodextrin,.and sucrose. The mild sweetness of ENSURE POWDER, plus VARI-FLAVORS® Flavor Pacs in pecan, cherry, strawberry, lemon, and orange, helps to prevent flavor fatigue and aid in patient compliance.

Vanilla:

| | |
|---|---|
| Corn Syrup | 35% |
| Maltodextrin | 35% |
| Sucrose | 30% |

H. ENSURE® PUDDING

Usage: ENSURE PUDDING is a nutrient-dense supplement providing balanced nutrition in a nonliquid form to be used with or between meals. It is appropriate for consistency-modified diets (e.g., soft, pureed, or full liquid) or for people with swallowing impairments. ENSURE PUDDING is gluten-free.

Patient Conditions:
For patients on consistency-modified diets (e.g., soft, pureed, or full liquid)
For patients with swallowing impairments Features:
Rich and creamy, good taste
Good source of essential vitamins and minerals
Convenient-needs no refrigeration
Gluten-free
Nutrient Profile per 5 oz: Calories 250, Protein 10.9%, Total Fat 34.9%, Carbohydrate 54.2%

Ingredients:
Vanilla: −D Nonfat Milk, Water, Sugar (Sucrose), Partially Hydrogenated Soybean Oil, Modified Food Starch, Magnesium Sulfate, Sodium Stearoyl Lactylate, Sodium Phosphate Dibasic, Artificial Flavor, Ascorbic Acid, Zinc Sulfate, Ferrous Sulfate, Alpha-Tocopheryl Acetate, Choline Chloride, Niacinamide, Manganese Sulfate, Calcium Pantothenate, FD&C Yellow #5, Potassium Citrate, Cupric Sulfate, Vitamin A Palmitate, Thiamine Chloride Hydrochloride, Pyridoxine Hydrochloride, Riboflavin, FD&C Yellow #6, Folic Acid, Biotin, Phylloquinone, Vitamin D3 and Cyanocobalamin.

Protein:
The protein source is nonfat milk.

| Nonfat milk | 100% |
|---|---|

Fat:
The fat source is hydrogenated soybean oil.

| Hydrogenated soybean oil | 100% |
|---|---|

Carbohydrate:
ENSURE PUDDING contains a combination of sucrose and modified food starch. The mild sweetness and flavor variety (vanilla, chocolate, butterscotch, and tapioca) help prevent flavor fatigue. The product contains 9.2 grams of lactose per serving.

Vanilla and other nonchocolate flavors:
Sucrose 56%
Lactose 27%
Modified food starch 17%

Chocolate:
Sucrose 58%
Lactose 26%
Modified food starch 16%

I. ENSURE® WITH FIBER

Usage: ENSURE WITH FIBER is a fiber-containing, nutritionally complete liquid food designed for people who can benefit from increased dietary fiber and nutrients. ENSURE WITH FIBER is suitable for people who do not require a low-residue diet. It can be fed orally or by tube, and can be used as a nutritional supplement to a regular diet or, in appropriate amounts, as a meal replacement. ENSURE WITH FIBER is lactose- and gluten-free, and is suitable for use in modified diets, including low-cholesterol diets.

Patient Conditions:
For patients who can benefit from increased dietary fiber and nutrients Features:
New advanced formula-low in saturated fat, higher in vitamins and minerals
Contains 6 g of total fat and <5 mg of cholesterol per serving
Rich, creamy taste
Good source of fiber
Excellent source of essential vitamins and minerals
For low-cholesterol diets
Lactose- and gluten-free Ingredients:
Vanilla: -D Water; Maltodextrin (Corn), Sugar (Sucrose), Sodium and Calcium Caseinates, Oat Fiber, High-Oleic Safflower Oil, Canola Oil, Soy Protein Isolate, Corn Oil, Soy Fiber, Calcium Phosphate Tribasic, Magnesium Chloride, Potassium Citrate, Cellulose Gel, Soy Lecithin, Potassium Phosphate Dibasic, Sodium Citrate, Natural and Artificial Flavors, Choline Chloride, Magnesium Phosphate, Ascorbic Acid, Cellulose Gum, Potassium Chloride, Carrageenan, Ferrous Sulfate, Alpha-Tocopheryl Acetate, Zinc Sulfate, Niacinamide, Manganese Sulfate, Calcium Pantothenate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Potassium Iodide, Sodium Selenate, Phylloquinone, Vitamin D3 and Cyanocobalamin.

Protein:
The protein source is a blend of two high-biologic-value proteins-casein and soy.

| Sodium and calcium caseinates | 80% |
|---|---|
| Soy protein isolate | 20% |

Fat:
The fat source is a blend of three oils: high-oleic safflower, canola, and corn.

| High-oleic safflower oil | 40% |
|---|---|
| Canola oil | 40% |
| Corn oil | 20% |

The level of fat in ENSURE WITH FIBER meets American Heart Association (AHA) guidelines. The 6 grams of fat in ENSURE WITH FIBER represent 22% of the total calories, with 2.01% of the fat being from saturated fatty acids and 6.7% from polyunsaturated fatty acids. These values are within the AHA guidelines of <30% of total calories from fat, <10% of the calories from saturated fatty acids, and <10% of total calories from polyunsaturated fatty acids.

Carbohydrate:
ENSURE WITH FIBER contains a combination of maltodextrin and sucrose. The mild sweetness and flavor variety (vanilla, chocolate, and butter pecan), plus VARI-FLA-VORS® Flavor Pacs in pecan, cherry, strawberry, lemon, and orange, help to prevent flavor fatigue and aid in patient compliance.

Vanilla and other nonchocolate flavors:

| Vanilla and other nonchocolate flavors: | |
|---|---|
| Maltodextrin | 66% |
| Sucrose | 25% |
| Oat Fiber | 7% |
| Soy Fiber | 2% |
| Chocolate: | |
| Maltodextrin | 55% |
| Sucrose | 36% |
| Oat Fiber | 7% |
| Soy Fiber | 2% |

Fiber:
The fiber blend used in ENSURE WITH FIBER consists of oat fiber and soy polysaccharide. This blend results in approximately 4 grams of total dietary fiber per 8-fl. oz can. The ratio of insoluble to soluble fiber is 95:5.

The various nutritional supplements described above and known to others of skill in the art can be substituted and/or supplemented with the PUFAs produced in accordance with the present invention.

J. OXEPA Nutritional Product

Oxepa is a low-carbohydrate, calorically dense, enteral nutritional product designed for the dietary management of patients with or at risk for ARDS. It has a unique combination of ingredients, including a patented oil blend containing eicosapentaenoic acid (EPA from fish oil), y-linolenic acid (GLA from borage oil), and elevated antioxidant levels.

Caloric Distribution:

Caloric density is high at 1.5 Cal/mL (355 Cal/8 fl oz), to minimize the volume required to meet energy needs.

The distribution of Calories in Oxepa is shown in Table A.

TABLE A

Caloric Distribution of Oxepa

|  | per 8 fl oz. | per liter | % of Cal |
|---|---|---|---|
| Calories | 355 | 1,500 | — |
| Fat (g) | 22.2 | 93.7 | 55.2 |
| Carbohydrate (g) | 25 | 105.5 | 28.1 |
| Protein (g) | 14.8 | 62.5 | 16.7 |
| Water (g) | 186 | 785 | — |

Fat:

Oxepa contains 22.2 g of fat per 8-fl oz serving (93.7 g/L).

The fat source is an oil blend of 31.8% canola oil, 25% medium-chain triglycerides (MCTs), 20% borage oil, 20% fish oil, and 3.2% soy lecithin. The typical fatty acid profile of Oxepa is shown in Table B.

OXEPA™ provides a balanced amount of polyunsaturated, monounsaturated, and saturated fatty acids, as shown in Table VI.

Medium-chain trigylcerides (MCTs)—25% of the fat blend—aid gastric emptying because they are absorbed by the intestinal tract without emulsification by bile acids.

The various fatty acid components of Oxepa™ nutritional product can be substituted and/or supplemented with the PUFAs produced in accordance with this invention.

TABLE B

Typical Fatty Acid Profile

| Fatty Acids | % Total | g/8 fl oz* | 9/L* |
|---|---|---|---|
| Caproic (6:0) | 0.2 | 0.04 | 0.18 |
| Caprylic (8:0) | 14.69 | 3.1 | 13.07 |
| Capric (10:0) | 11.06 | 2.33 | 9.87 |
| Palmitic (16:0) | 5.59 | 1.18 | 4.98 |
| Palmitoleic | 1.82 | 0.38 | 1.62 |
| Stearic | 1.94 | 0.39 | 1.64 |
| Oleic | 24.44 | 5.16 | 21.75 |
| Linoleic | 16.28 | 3.44 | 14.49 |
| α-Linolenic | 3.47 | 0.73 | 3.09 |
| γ-Linolenic | 4.82 | 1.02 | 4.29 |
| Eicosapentaenoic | 5.11 | 1.08 | 4.55 |
| n-3-Docosapentaenoic | 0.55 | 0.12 | 0.49 |
| Docosahexaenoic | 2.27 | 0.48 | 2.02 |
| Others | 7.55 | 1.52 | 6.72 |

Fatty acids equal approximately 95% of total fat.

TABLE C

Fat Profile of Oxepa.

| % of total calories from fat | 55.2 |
|---|---|
| Polyunsaturated fatty acids | 31.44 g/L |
| Monounsaturated fatty acids | 25.53 g/L |
| Saturated fatty acids | 32.38 g/L |
| n − 6 to n − 3 ratio | 1.75:1 |
| Cholesterol | 9.49 mg/8 fl oz |
|  | 40.1 mg/L |

Carbohydrate:

The carbohydrate content is 25.0 g per 8-fl-oz serving (105.5 g/L).

The carbohydrate sources are 45% maltodextrin (a complex carbohydrate) and 55% sucrose (a simple sugar), both of which are readily digested and absorbed.

The high-fat and low-carbohydrate content of Oxepa is designed to minimize carbon dioxide ($CO_2$) production. High CO2 levels can complicate weaning in ventilator-dependent patients. The low level of carbohydrate also may be useful for those patients who have developed stress-induced hyperglycemia.

OXEPA™ is lactose-free.

Dietary carbohydrate, the amino acids from protein, and the glycerol moiety of fats can be converted to glucose within the body. Throughout this process, the carbohydrate requirements of glucose-dependent tissues (such as the central nervous system and red blood cells) are met. However, a diet free of carbohydrates can lead to ketosis, excessive catabolism of tissue protein, and loss of fluid and electrolytes. These effects can be prevented by daily ingestion of 50 to 100 g of digestible carbohydrate, if caloric intake is adequate. The carbohydrate level in Oxepa is also sufficient to minimize gluconeogenesis, if energy needs are being met.

Protein:

Oxepa contains 14.8 g of protein per 8-fl-oz serving (62.5 g/L).

The total calorie/nitrogen ratio (150:1) meets the need of stressed patients.

Oxepa provides enough protein to promote anabolism and the maintenance of lean body mass without precipitating respiratory problems. High protein intakes are a concern in patients with respiratory insufficiency. Although protein has little effect on $CO_2$ production, a high protein diet will increase ventilatory drive.

The protein sources of Oxepa are 86.8% sodium caseinate and 13.2% calcium caseinate.

The amino acid profile of the protein system in Oxepa meets or surpasses the standard for high quality protein set by the National Academy of Sciences.

OXEPA™ is gluten-free.

The invention claimed is:

1. An isolated nucleotide sequence comprising or complementary to a nucleotide sequence encoding a polypeptide having Δ4-desaturase activity, wherein the amino acid sequence of said polypeptide has at least 90% identity to the amino acid of SEQ ID NO:20, or a fragment thereof encoding Δ4-desaturase activity.

2. An isolated nucleotide sequence comprising or complementary to a nucleotide sequence having at least 90% identity to the nucleotide sequence of SEQ ID NO:16 encoding Δ4-desaturase activity, or a fragment thereof encoding Δ4-desaturase activity.

3. The nucleotide sequence of claim 1 or claim 2 wherein said sequence is derived from the fungus *Thraustochytrium aureum*.

4. A method of producing a Δ4-desaturase comprising the steps of:
   a) isolating a nucleotide sequence comprising or complementary to a nucleotide sequence:
      i) encoding a polypeptide comprising an amino acid sequence having at least 90% identity to the amino acid sequence of SEQ ID NO:20 having Δ4-desaturase activity or
      ii) having at least 90% identity to the nucleotide sequence of SEQ ID NO: 16 encoding Δ4-desaturase activity;
   b) constructing a vector comprising: i) said isolated nucleotide sequence operably linked to ii) a promoter; and
   c) introducing said vector into a host cell for a time and under conditions sufficient for expression of said desaturase, thereby producing Δ4-desaturase.

5. A vector comprising:
   a) an isolated nucleotide sequence comprising or complementary to a nucleotide sequence:
      i) encoding a polypeptide comprising the amino acid sequence having at least 90% identity to an amino acid sequence of SEQ ID NO:20 having Δ4-desaturase activity or ii) having at least 90% identity to the nucleotide sequence of SEQ ID NO: 16 encoding Δ4-desaturase activity, operably linked to b) a promoter.

6. An isolated host cell comprising said vector of claim 5.

7. The isolated nucleotide sequence of claim 1 or claim 2 wherein said nucleotide sequence encodes a Δ4-desaturase which utilizes a monounsaturated or polyunsaturated fatty acid as a substrate.

8. A method for producing a polyunsaturated fatty acid comprising the steps of:
 a) isolating said nucleotide sequence of claim 1 or claim 2;
 b) constructing a vector comprising said isolated nucleotide sequence;
 c) transforming said vector into a host cell for a time and under conditions sufficient for expression of a Δ4-desaturase encoded by said nucleotide sequence;
 d) exposing said expressed Δ4-desaturase to a polyunsaturated fatty acid substrate, in order to convert said substrate to a product polyunsaturated fatty acid; and
 e) isolating said product polyunsaturated fatty acid.

9. The method according to claim 8, wherein said substrate is adrenic acid or ω3-docosapentaenoic acid and said product polyunsaturated fatty acid is ω6-docosapentaenoic acid or docosahexaenoic acid, respectively.

10. The method according to claim 8 further compeising the step of exposing said product polyunsaturated fatty acid to a desaturase in order to convert said product polyunsaturated fatty acid to another polyunsaturated fatty acid.

11. The method according to claim 10 wherein said product polyunsaturated fatty acid is ω6-docosapentaenoic acid and said another polyunsaturated fatty acid is docosahexaenoic acid.

* * * * *

SEQUENCE LISTING

<160> NUMBER OF SEQ ID NOS: 73

<210> SEQ ID NO 1
<211> LENGTH: 42
<212> TYPE: DNA
<213> ORGANISM: Artificial Sequence
<220> FEATURE:
<223> OTHER INFORMATION: Primer RO834
<220> FEATURE:
<221> NAME/KEY: misc_feature
<222> LOCATION: (3)...(3)
<223> OTHER INFORMATION: b = g or c or t/u at position 3
<220> FEATURE:
<221> NAME/KEY: misc_feature
<222> LOCATION: (6)...(6)
<223> OTHER INFORMATION: y = t/u or c at position 6
<220> FEATURE:
<221> NAME/KEY: misc_feature
<222> LOCATION: (9)...(9)
<223> OTHER INFORMATION: y = t/u or c at position 9
<220> FEATURE:
<221> NAME/KEY: misc_feature
<222> LOCATION: (12)...(12)
<223> OTHER INFORMATION: b = g or c or t/u at position 12
<220> FEATURE:
<221> NAME/KEY: misc_feature
<222> LOCATION: (18)...(18)
<223> OTHER INFORMATION: r = g or a at position 18
<220> FEATURE:
<221> NAME/KEY: misc_feature
<222> LOCATION: (24)...(24)
<223> OTHER INFORMATION: b = g or c or t/u at position 24
<220> FEATURE:
<221> NAME/KEY: misc_feature
<222> LOCATION: (30)...(30)
<223> OTHER INFORMATION: y = t/u or c at position 30
<220> FEATURE:
<221> NAME/KEY: misc_feature
<222> LOCATION: (33)...(33)
<223> OTHER INFORMATION: y = t/u or c at position 33
<220> FEATURE:
<221> NAME/KEY: misc_feature
<222> LOCATION: (36)...(36)
<223> OTHER INFORMATION: b = g or c or t/u at position 36
<220> FEATURE:
<221> NAME/KEY: misc_feature
<222> LOCATION: (39)...(39)
<223> OTHER INFORMATION: h = a or c or t/u at position 39
<220> FEATURE:
<221> NAME/KEY: misc_feature
<222> LOCATION: (42)...(42)
<223> OTHER INFORMATION: h = a or c or t/u at position 42

<400> SEQUENCE: 1
gtbtaygayg tbaccgartg ggtbaagcgy cayccbgghg gh                          42

<210> SEQ ID NO 2
<211> LENGTH: 45
<212> TYPE: DNA
<213> ORGANISM: Artificial Sequence
<220> FEATURE:
<223> OTHER INFORMATION: Forward Primer RO835
<220> FEATURE:
<221> NAME/KEY: misc_feature
<222> LOCATION: (3)...(3)
<223> OTHER INFORMATION: h = a or c or t/u at position 3
<220> FEATURE:
<221> NAME/KEY: misc_feature
<222> LOCATION: (6)...(6)
<223> OTHER INFORMATION: y = t/u or c at position 6
<220> FEATURE:
<221> NAME/KEY: misc_feature
<222> LOCATION: (12)...(12)
<223> OTHER INFORMATION: y = t/u or c at position 12

```
<220> FEATURE:
<221> NAME/KEY: misc_feature
<222> LOCATION: (27)...(27)
<223> OTHER INFORMATION: y = t/u or c at position 27
<220> FEATURE:
<221> NAME/KEY: misc_feature
<222> LOCATION: (33)...(33)
<223> OTHER INFORMATION: y = t/u or c at position 33
<220> FEATURE:
<221> NAME/KEY: misc_feature
<222> LOCATION: (39)...(39)
<223> OTHER INFORMATION: b = g or c or t/u at position 39
<220> FEATURE:
<221> NAME/KEY: misc_feature
<222> LOCATION: (42)...(42)
<223> OTHER INFORMATION: y = t/u or c at position 42
<220> FEATURE:
<221> NAME/KEY: misc_feature
<222> LOCATION: (45)...(45)
<223> OTHER INFORMATION: y = t/u or c at position 45

<400> SEQUENCE: 2
gghgcytccg cyaactggtg gaagcaycag cayaacgtbc aycay            45

<210> SEQ ID NO 3
<211> LENGTH: 45
<212> TYPE: DNA
<213> ORGANISM: Artificial Sequence
<220> FEATURE:
<223> OTHER INFORMATION: Reverse Primer RO836
<220> FEATURE:
<221> NAME/KEY: misc_feature
<222> LOCATION: (1)...(1)
<223> OTHER INFORMATION: r = g or a at position 1
<220> FEATURE:
<221> NAME/KEY: misc_feature
<222> LOCATION: (4)...(4)
<223> OTHER INFORMATION: r = g or a at position 4
<220> FEATURE:
<221> NAME/KEY: misc_feature
<222> LOCATION: (7)...(7)
<223> OTHER INFORMATION: v = a or g or c at position 7
<220> FEATURE:
<221> NAME/KEY: misc_feature
<222> LOCATION: (13)...(13)
<223> OTHER INFORMATION: r = g or a at position 13
<220> FEATURE:
<221> NAME/KEY: misc_feature
<222> LOCATION: (19)...(19)
<223> OTHER INFORMATION: r = g or a at position 19
<220> FEATURE:
<221> NAME/KEY: misc_feature
<222> LOCATION: (34)...(34)
<223> OTHER INFORMATION: r = g or a at position 34
<220> FEATURE:
<221> NAME/KEY: misc_feature
<222> LOCATION: (40)...(40)
<223> OTHER INFORMATION: r = g or a at position 40
<220> FEATURE:
<221> NAME/KEY: misc_feature
<222> LOCATION: (43)...(43)
<223> OTHER INFORMATION: d = a or g or t/u at position 43

<400> SEQUENCE: 3
rtgrtgvacg ttrtgctgrt gcttccacca gttrgcggar gcdcc            45

<210> SEQ ID NO 4
<211> LENGTH: 36
<212> TYPE: DNA
<213> ORGANISM: Artificial Sequence
<220> FEATURE:
<223> OTHER INFORMATION: Reverse Primer RO838
<220> FEATURE:
<221> NAME/KEY: misc_feature
<222> LOCATION: (6)...(6)
```

<223> OTHER INFORMATION: r = g or a at position 6
<220> FEATURE:
<221> NAME/KEY: misc_feature
<222> LOCATION: (12)...(12)
<223> OTHER INFORMATION: r = g or a at position 12
<220> FEATURE:
<221> NAME/KEY: misc_feature
<222> LOCATION: (15)...(15)
<223> OTHER INFORMATION: y = t/u or c at position 15
<220> FEATURE:
<221> NAME/KEY: misc_feature
<222> LOCATION: (18)...(18)
<223> OTHER INFORMATION: r = g or a at position 18
<220> FEATURE:
<221> NAME/KEY: misc_difference
<222> LOCATION: (21)...(21)
<223> OTHER INFORMATION: r = g or a at position 21
<220> FEATURE:
<221> NAME/KEY: misc_feature
<222> LOCATION: (24)...(24)
<223> OTHER INFORMATION: s = g or c at position 24
<220> FEATURE:
<221> NAME/KEY: misc_feature
<222> LOCATION: (27)...(27)
<223> OTHER INFORMATION: r = g or a at position 27
<220> FEATURE:
<221> NAME/KEY: misc_feature
<222> LOCATION: (30)...(30)
<223> OTHER INFORMATION: v = a or g or c at position 30

<400> SEQUENCE: 4
ttgatrgtct arctygtrgt rgasaarggv tggtac                            36

<210> SEQ ID NO 5
<211> LENGTH: 24
<212> TYPE: DNA
<213> ORGANISM: Artificial Sequence
<220> FEATURE:
<223> OTHER INFORMATION: Primer RO753
<220> FEATURE:
<221> NAME/KEY: misc_feature
<222> LOCATION: (10)...(10)
<223> OTHER INFORMATION: n = a or g or c or t/u, unknown or other at
     position 10
<220> FEATURE:
<221> NAME/KEY: misc_feature
<222> LOCATION: (13)...(13)
<223> OTHER INFORMATION: r = g or a at position 13
<220> FEATURE:
<221> NAME/KEY: misc_feature
<222> LOCATION: (16)...(16)
<223> OTHER INFORMATION: n = a or g or c or t/u, unknown or other at
     position 16
<220> FEATURE:
<221> NAME/KEY: misc_feature
<222> LOCATION: (18)...(19)
<223> OTHER INFORMATION: r = g or a at positions 18-19
<220> FEATURE:
<221> NAME/KEY: misc_feature
<222> LOCATION: (22)...(22)
<223> OTHER INFORMATION: r = g or a at position 22

<400> SEQUENCE: 5
catcatcatn ggraanarrt grtg                                         24

<210> SEQ ID NO 6
<211> LENGTH: 30
<212> TYPE: DNA
<213> ORGANISM: Artificial Sequence
<220> FEATURE:
<223> OTHER INFORMATION: Primer RO754
<220> FEATURE:
<221> NAME/KEY: misc_feature
<222> LOCATION: (15)...(15)
<223> OTHER INFORMATION: y = t/u or c at position 15

```
<220> FEATURE:
<221> NAME/KEY: misc_feature
<222> LOCATION: (18)...(18)
<223> OTHER INFORMATION: y = t/u or c at position 18
<220> FEATURE:
<221> NAME/KEY: misc_feature
<222> LOCATION: (21)...(21)
<223> OTHER INFORMATION: n = a or g or c or t/u, unknown, or other at
      position 21
<220> FEATURE:
<221> NAME/KEY: misc_feature
<222> LOCATION: (24)...(24)
<223> OTHER INFORMATION: y = t/u or c at position 24
<220> FEATURE:
<221> NAME/KEY: misc_feature
<222> LOCATION: (27)...(27)
<223> OTHER INFORMATION: n = a or g or c or t/u, unknown, or other at
      position 27
<220> FEATURE:
<221> NAME/KEY: misc_feature
<222> LOCATION: (30)...(30)
<223> OTHER INFORMATION: y = t/u or c at position 30

<400> SEQUENCE: 6
ctactactac tacaycayac ntaycacnaay                                     30

<210> SEQ ID NO 7
<211> LENGTH: 31
<212> TYPE: DNA
<213> ORGANISM: Artificial Sequence
<220> FEATURE:
<223> OTHER INFORMATION: Primer RO898

<400> SEQUENCE: 7
cccagtcacg acgttgtaaa acgacggcca g                                    31

<210> SEQ ID NO 8
<211> LENGTH: 31
<212> TYPE: DNA
<213> ORGANISM: Artificial Sequence
<220> FEATURE:
<223> OTHER INFORMATION: Primer RO930

<400> SEQUENCE: 8
gacgattaac aaggtgattt cccaggatgt c                                    31

<210> SEQ ID NO 9
<211> LENGTH: 38
<212> TYPE: DNA
<213> ORGANISM: Artificial Sequence
<220> FEATURE:
<223> OTHER INFORMATION: Primer RO973

<400> SEQUENCE: 9
gactaactcg agtcacgtgg accaggccgt gaggtcct                             38

<210> SEQ ID NO 10
<211> LENGTH: 45
<212> TYPE: DNA
<213> ORGANISM: Artificial Sequence
<220> FEATURE:
<223> OTHER INFORMATION: Primer RO974

<400> SEQUENCE: 10
gactaactcg agttgacgag gtttgtatgt tcggcggttt gcttg                     45

<210> SEQ ID NO 11
<211> LENGTH: 30
<212> TYPE: DNA
```

<213> ORGANISM: Artificial Sequence
<220> FEATURE:
<223> OTHER INFORMATION: Primer RO899

<400> SEQUENCE: 11
agcggataac aatttcacac aggaaacagc                                30

<210> SEQ ID NO 12
<211> LENGTH: 30
<212> TYPE: DNA
<213> ORGANISM: Artificial Sequence
<220> FEATURE:
<223> OTHER INFORMATION: Primer RO1004

<400> SEQUENCE: 12
tggctaccgt cgtgctggat gcaagttccg                                30

<210> SEQ ID NO 13
<211> LENGTH: 39
<212> TYPE: DNA
<213> ORGANISM: Artificial Sequence
<220> FEATURE:
<223> OTHER INFORMATION: Primer RO1046

<400> SEQUENCE: 13
cgcatggaat tcatgacggt cgggtttgac gaaacggtg                      39

<210> SEQ ID NO 14
<211> LENGTH: 1548
<212> TYPE: DNA
<213> ORGANISM: Thraustochytrium aureum

<400> SEQUENCE: 14
atgacggtcg ggtttgacga aacggtgact atggacacgg tccgcaacca caacatgccg    60
gacgacgcct ggtgcgcgat ccacggcacc gtgtacgaca tcaccaagtt cagcaaggtg   120
caccccggcg gggacatcat catgctggcc gctggcaagg aggccaccat cctgttcgag   180
acgtaccaca tcaagggcgt cccggacgcg gtgctgcgca agtacaaggt cggcaagctc   240
ccccagggca agaagggcga aacgagccac atgcccaccg ggctcgactc ggcctcctac   300
tactcgtggg acagcgagtt ttacaggggtg ctccgcgagc gcgtcgccaa gaagctggcc   360
gagcccggcc tcatgcagcg cgcgcgcatg gagctctggg ccaaggcgat cttcctcctg   420 gcaggttttct ggggctccct ttacgccatg tgcgtgctag acccgcacgg cggtgccatg   480
gtagccgccg ttacgctcgg cgtgttcgct gcctttgtcg gaacttgcat ccagcacgac   540
ggcagccacg cgcgccttctc caagtcgcga ttcatgaaca aggcggcggg ctggaccctc   600
gacatgatcg gcgcgagcgc gatgacctgg gagatgcagc acgttcttgg ccaccacccg   660
tacaccaacc tcatcgagat ggagaacggt ttggccaagg tcaagggcgc cgacgtcgac   720
ccgaagaagg tcgaccagga gagcgacccg gacgtcttca gtacgtaccc gatgcttcgc   780
ctgcacccgt ggcaccgcca gcggttttac cacaagttcc agcacctgta cgccccgttt   840
atctttgggt ttatgacgat taacaaggtg atttcccagg atgtcggggt tgtgctgcgc   900
aagcgcctgt tccagatcga cgccaactgc cggtatggca gccctggta cgtggcccgc   960 ttctggatca tgaagctcct caccacgctc tacacggtgg cgcttcccat gtacatgcag  1020
gggcctgctc agggcttgaa gcttttcttc atggcccact tcacctgcgg agaggtcctc  1080
gccaccatgt ttattgtcaa ccacatcatc gagggcgtca gctacgcttc caaggacgcg  1140
gtcaagggcg tcatggctcc gccgcgcact gtgcacggtg tcaccccgat gcaggtgacg  1200

```
caaaaggcgc tcagtgcggc cgagtcgacc aagtcggacg ccgacaagac gaccatgatc    1260
cccctcaacg actgggccgc tgtgcagtgc cagacctctg tgaactgggc tgtcgggtcg    1320
tggttttgga accactttc gggcggcctc aaccaccaga ttgagcacca ctgcttcccc    1380 caaaacccc acacggtcaa cgtctacatc tcggcatcg tcaaggagac ctgcgaagaa    1440
tacggcgtgc cgtaccaggc tgagatcagc ctcttctctg cctatttcaa gatgctgtcg    1500
cacctccgca cgctcggcaa cgaggacctc acggccaggt ccacgtga                1548

<210> SEQ ID NO 15
<211> LENGTH: 1548
<212> TYPE: DNA
<213> ORGANISM: Thraustochytrium aureum

<400> SEQUENCE: 15
atgacggtcg ggtttgacga aacggtgact atggacacgg tccgcaacca caacatgccg    60
gacgacgcct ggtgcgcgat ccacggcacc gtgtacgaca tcaccaagtt cagcaaggtg   120
cacccgggcg gggacatcat catgctggcg gctggcaagg aggccaccat cctgttcgag   180
acgtaccaca tcaagggcgt tccggacgcg gtgctgcgca agtacaaggt cggcaagctc   240
ccccagggca agaagggcga aacgagccac atgcccaccg gctcgactc ggccttctac   300 tactcgtggg acagcgagtt ttacaggtgt ctccgcgagc gcgtcgccaa gaagctggcc   360
gagcccggcc tcatgcagcg cgcgcgcatg gagctctggg ccaaggcgat cttcctcctg   420
gcaggtttct ggggctccct ttacgccatg tgcgtgctag accgcacgg cggtgccatg    480 gtagccgccg ttacgctcgg cgtgttcgct gcctttgtcg aacttgcat ccagcacgac   540 ggcagccacg gcgccttctc caagtcgcga ttcatgaaca aggcggcggg ctggaccctc   600
gacatgatcg gcgcgagcgc gatgacctgg gagatgcagc acgttcttgg ccaccacccg   660
tacaccaacc tcatcgagat ggagaacggt ttggccaagg tcaagggcgc cgacgtcgac   720
ccgaagaagg tcgaccagga gagcgacccg gacgtcttca gtacgtaccc gatgcttcgc   780
ctgcacccgt ggcaccgcca gcggttttac cacaagttcc agcacctgta cgccccgttt   840
atctttgggt ttatgacgat taacaaggtg atttcccagg atgtcggggt tgtgctgcgc   900
aagcgcctgt tccagatcga cgccaactgc cggtatggca gccccctgta cgtggcccgc   960
ttctggatca tgaagctcct caccacgctc tacatggtgg cgcttcccat gtacatgcag   1020
gggcctgctc agggcttgaa gcttttcttc atggcccact tcacctgcgg agaggtcctc   1080
gccaccatgt ttattgtcaa ccacatcatc gagggcgtca gctacgcttc caaggacgcg   1140
gtcaagggcg tcatggctcc gccgcgcact gtgcacggtg tcaccccgat gcaggtgacg   1200
caaaaggcgc tcagtgcggc cgagtcgacc aagtcggacg ccgacaagac gaccatgatc   1260
cccctcaacg actgggccgc tgtgcagtgc cagacctctg tgaactgggc tgtcgggtcg   1320
tggttttgga accactttc gggcggcctc aaccaccaga ttgagcacca ctgcttcccc   1380 caaaacccc acacggtcaa cgtctacatc tcggcatcg tcaaggagac ctgcgaagaa   1440
tacggcgtgc cgtaccaggc tgagatcagc ctcttctctg cctatttcaa gatgctgtcg   1500
cacctccgca cgctcggcaa cgaggacctc acggcctggt ccacgtga               1548

<210> SEQ ID NO 16
<211> LENGTH: 1548
<212> TYPE: DNA
<213> ORGANISM: Thraustochytrium aureum
```

-continued

```
<400> SEQUENCE: 16
atgacggtcg ggtttgacga aacggtgact atggacacgg tccgcaacca caacatgccg      60
gacgacgcct ggtgcgcgat ccacggcacc gtgtacgaca tcaccaagtt cagcaaggtg     120
caccccggcg gggacatcat catgctggcc gctggcaagg aggccaccat cctgttcgag     180
acctaccaca tcaagggcgt cccggacgcg gtgctgcgca agtacaaggt cggcaagctc     240
ccccagggca agaagggcga aacgagccac atgcccaccg ggctcgactc ggcctcctac     300
tactcgtggg acagcgagtt ttacagggtg ctccgcgagc gcgtcgccaa gaagctggcc     360
gagcccggcc tcatgcagcg cgcgcgcatg gagctctggg ccaaggcgat cttcctcctg     420
gcaggtttct ggggctccct ttacgccatg tgcgtgctag acccgcacgg cggtgccatg     480
gtagccgccg ttacgctcgg cgtgttcgct gcctttgtcg aacttgcat ccagcacgac     540 ggcagccacg gcgccttctc caagtcgcga ttcatgaaca aggcggcggg ctggaccctc     600
gacatgatcg gcgcgagcgc gatgacctgg gagatgcagc acgttcttgg tcaccacccg     660
tacaccaacc tcatcgagat ggagaacggt ttggccaagg tcaagggcgc cgacgtcgac     720
ccgaagaagg tcgaccagga gagcgacccg gacgtcttca gtacgtaccc gatgcttcgc     780
ctgcacccgt ggcaccgcca gcggttttac acaagttcc agcacctgta cgccccgctt     840
atctttgggt ttatgacgat taacaaggtg atttcccagg atgtcggggt tgtgctgcgc     900
aagcgcctgt tccagatcga cgccaactgc cggtatggca gcccctggaa cgtggcccgc     960
ttctggatca tgaagctcct caccacgctc tacatggtgg cgcttcccat gtacatgcag    1020
gggcctgctc agggcttgaa gcttttcttc atggcccact tcacctgcgg agaggtcctc    1080
gccaccatgt ttattgtcaa ccacatcatc gagggcgtca gctacgcttc caaggacgcg    1140
gtcaagggcg tcatggctcc gccgcgcact gtgcacggtg tcaccccgat gcaggtgacg    1200
caaaaggcgc tcagtgcggc cgagtcgacc aagtcggacg ccgacaagac gaccatgatc    1260 ccctcaacg actgggccgc tgtgcagtgc cagacctctg tgaactgggc tgtcgggtcg    1320
tggttttgga accactttc gggcggccta aaccaccaga ttgagcacca ctgcttcccc    1380
caaaaccccc acacggtcaa cgtctacatc tcgggcatcg tcaaggagac ctgcgaagaa    1440
tacggcgtgc cgtaccaggc tgagatcagc ctcttctctg cctatttcaa gatgctgtcg    1500
cacctccgca cgctcggcaa cgaggacctc acggcctggt ccacgtga                 1548

<210> SEQ ID NO 17
<211> LENGTH: 1548
<212> TYPE: DNA
<213> ORGANISM: Thraustochytrium aureum

<400> SEQUENCE: 17
atgacggtcg ggtttgacga aacggtgact atggacacgg tccgcaacca caacatgccg      60
gacgacgcct ggtgcgcgat ccacggcacc gtgtacgaca tcaccaagtt cagcaaggtg     120
caccccggcg gggacatcat catgctggcc gctggcaagg aggccaccat cctgttcgag     180
acctaccaca tcaagggcgt cccggacgcg gtgctgcgca agtacaaggt cggcaagctc     240
ccccagggca agaagggcga aacgagccac atgcccaccg ggctcgactc ggcctcctac     300
tactcgtggg acagcgagtt ttacagggtg ctccgcgagc gcgtcgccaa gaagctggcc     360
gagcccggcc tcatgcagcg cgcgcgcatg gagctctggg ccaaggcgat cttcctcctg     420
gcaggtttct ggggctccct ttacgccatg tgcgtgctag acccgcacgg cggtgccatg     480
gtagccgccg ttacgctcgg cgtgttcgct gcctttgtcg aacttgcat ccagcacgac     540
```

```
ggcagccacg cgccttctc caagtcgcga ttcatgaaca aggcggcggg ctggaccctc      600
gacatgatcg gcgcgagtgc gatgacctgg gagatgcagc acgttcttgg ccaccacccg      660
tacaccaacc tcatcgagat ggagaacggt ttggccaagg tcaagggcgc cgacgtcgac      720
ccgaagaagg tcgaccagga gagcgacccg gacgtcttca gtacgtaccc gatgcttcgc      780
ctgcacccgt ggcaccgcca gcggttttac cacaagttcc agcacctgta cgccccgttt      840
atctttgggt ctatgacgat taacaaggtg atttcccagg atgtcggggt tgtgctgcgc      900
aagcgcctgt tccagatcga cgccaactgc cggtatggca gccctggta cgtggcccgc       960 ttctggatca tgaagctcct caccacgctc tacatggtgg cgcttcccat gtacatgcag    1020
gggcctgctc agggcttgaa gcttttcttc atggcccact tcacctgcgg agaggtcctc    1080
gccaccatgt ttattgtcaa ccacatcatc gagggcgtca gctacgcttc caaggacgcg    1140
gtcaagggcg tcatggctcc gccgcgcact gtgcacggtg tcaccccgat gcaggtgacg    1200
caaaaggcgc tcagtgcggc cgagtcggcc aagtcggacg ccgacaagac gaccatgatc    1260
cccctcaacg actgggccgc tgtgcagtgc cagacctctg tgaactgggc tgtcgggtcg    1320
tggttttgga accactttc gggcggcctc aaccaccaga ttgagcacca ctgcttcccc     1380 caaaacccccc acacggtcaa cgtctacatc tcgggcatcg tcaaggagac ctgcgaagaa    1440
tacggcgtgc cgtaccaggc tgagatcagc ctcttctctg cctatttcaa gatgctgtcg    1500
cacctccgca cgctcggcaa cgaggacctc acggcctggt ccacgtga                 1548

<210> SEQ ID NO 18
<211> LENGTH: 515
<212> TYPE: PRT
<213> ORGANISM: Thraustochytrium aureum

<400> SEQUENCE: 18

Met Thr Val Gly Phe Asp Glu Thr Val Thr Met Asp Thr Val Arg Asn
 1               5                  10                  15

His Asn Met Pro Asp Asp Ala Trp Cys Ala Ile His Gly Thr Val Tyr
            20                  25                  30

Asp Ile Thr Lys Phe Ser Lys Val His Pro Gly Gly Asp Ile Ile Met
        35                  40                  45

Leu Ala Ala Gly Lys Glu Ala Thr Ile Leu Phe Glu Thr Tyr His Ile
    50                  55                  60

Lys Gly Val Pro Asp Ala Val Leu Arg Lys Tyr Lys Val Gly Lys Leu
65                  70                  75                  80

Pro Gln Gly Lys Lys Gly Glu Thr Ser His Met Pro Thr Gly Leu Asp
                85                  90                  95

Ser Ala Ser Tyr Tyr Ser Trp Asp Ser Glu Phe Tyr Arg Val Leu Arg
            100                 105                 110

Glu Arg Val Ala Lys Lys Leu Ala Glu Pro Gly Leu Met Gln Arg Ala
        115                 120                 125

Arg Met Glu Leu Trp Ala Lys Ala Ile Phe Leu Leu Ala Gly Phe Trp
    130                 135                 140

Gly Ser Leu Tyr Ala Met Cys Val Leu Asp Pro His Gly Gly Ala Met
145                 150                 155                 160

Val Ala Ala Val Thr Leu Gly Val Phe Ala Ala Phe Val Gly Thr Cys
                165                 170                 175

Ile Gln His Asp Gly Ser His Gly Ala Phe Ser Lys Ser Arg Phe Met
            180                 185                 190
```

```
Asn Lys Ala Ala Gly Trp Thr Leu Asp Met Ile Gly Ala Ser Ala Met
        195                 200                 205

Thr Trp Glu Met Gln His Val Leu Gly His His Pro Tyr Thr Asn Leu
    210                 215                 220

Ile Glu Met Glu Asn Gly Leu Ala Lys Val Lys Gly Ala Asp Val Asp
225                 230                 235                 240

Pro Lys Lys Val Asp Gln Glu Ser Asp Pro Asp Val Phe Ser Thr Tyr
            245                 250                 255

Pro Met Leu Arg Leu His Pro Trp His Arg Gln Arg Phe Tyr His Lys
            260                 265                 270

Phe Gln His Leu Tyr Ala Pro Phe Ile Phe Gly Phe Met Thr Ile Asn
        275                 280                 285

Lys Val Ile Ser Gln Asp Val Gly Val Val Leu Arg Lys Arg Leu Phe
    290                 295                 300

Gln Ile Asp Ala Asn Cys Arg Tyr Gly Ser Pro Trp Tyr Val Ala Arg
305                 310                 315                 320

Phe Trp Ile Met Lys Leu Leu Thr Thr Leu Tyr Thr Val Ala Leu Pro
            325                 330                 335

Met Tyr Met Gln Gly Pro Ala Gln Gly Leu Lys Leu Phe Phe Met Ala
            340                 345                 350

His Phe Thr Cys Gly Glu Val Leu Ala Thr Met Phe Ile Val Asn His
        355                 360                 365

Ile Ile Glu Gly Val Ser Tyr Ala Ser Lys Asp Ala Val Lys Gly Val
    370                 375                 380

Met Ala Pro Pro Arg Thr Val His Gly Val Thr Pro Met Gln Val Thr
385                 390                 395                 400

Gln Lys Ala Leu Ser Ala Ala Glu Ser Thr Lys Ser Asp Ala Asp Lys
            405                 410                 415

Thr Thr Met Ile Pro Leu Asn Asp Trp Ala Ala Val Gln Cys Gln Thr
            420                 425                 430

Ser Val Asn Trp Ala Val Gly Ser Trp Phe Trp Asn His Phe Ser Gly
        435                 440                 445

Gly Leu Asn His Gln Ile Glu His His Cys Phe Pro Gln Asn Pro His
    450                 455                 460

Thr Val Asn Val Tyr Ile Ser Gly Ile Val Lys Glu Thr Cys Glu Glu
465                 470                 475                 480

Tyr Gly Val Pro Tyr Gln Ala Glu Ile Ser Leu Phe Ser Ala Tyr Phe
            485                 490                 495

Lys Met Leu Ser His Leu Arg Thr Leu Gly Asn Glu Asp Leu Thr Ala
            500                 505                 510

Arg Ser Thr
        515

<210> SEQ ID NO 19
<211> LENGTH: 515
<212> TYPE: PRT
<213> ORGANISM: Thraustochytrium aureum

<400> SEQUENCE: 19

Met Thr Val Gly Phe Asp Glu Thr Val Thr Met Asp Thr Val Arg Asn
1               5                   10                  15

His Asn Met Pro Asp Asp Ala Trp Cys Ala Ile His Gly Thr Val Tyr
            20                  25                  30

Asp Ile Thr Lys Phe Ser Lys Val His Pro Gly Gly Asp Ile Ile Met
        35                  40                  45
```

```
Leu Ala Ala Gly Lys Glu Ala Thr Ile Leu Phe Glu Thr Tyr His Ile
 50                  55                  60

Lys Gly Val Pro Asp Ala Val Leu Arg Lys Tyr Lys Val Gly Lys Leu
 65                  70                  75                  80

Pro Gln Gly Lys Lys Gly Glu Thr Ser His Met Pro Thr Gly Leu Asp
                 85                  90                  95

Ser Ala Phe Tyr Tyr Ser Trp Asp Ser Glu Phe Tyr Arg Val Leu Arg
             100                 105                 110

Glu Arg Val Ala Lys Lys Leu Ala Glu Pro Gly Leu Met Gln Arg Ala
         115                 120                 125

Arg Met Glu Leu Trp Ala Lys Ala Ile Phe Leu Leu Ala Gly Phe Trp
     130                 135                 140

Gly Ser Leu Tyr Ala Met Cys Val Leu Asp Pro His Gly Gly Ala Met
145                 150                 155                 160

Val Ala Ala Val Thr Leu Gly Val Phe Ala Ala Phe Val Gly Thr Cys
                 165                 170                 175

Ile Gln His Asp Gly Ser His Gly Ala Phe Ser Lys Ser Arg Phe Met
             180                 185                 190

Asn Lys Ala Ala Gly Trp Thr Leu Asp Met Ile Gly Ala Ser Ala Met
         195                 200                 205

Thr Trp Glu Met Gln His Val Leu Gly His His Pro Tyr Thr Asn Leu
     210                 215                 220

Ile Glu Met Glu Asn Gly Leu Ala Lys Val Lys Gly Ala Asp Val Asp
225                 230                 235                 240

Pro Lys Lys Val Asp Gln Glu Ser Asp Pro Asp Val Phe Ser Thr Tyr
                 245                 250                 255

Pro Met Leu Arg Leu His Pro Trp His Arg Gln Arg Phe Tyr His Lys
             260                 265                 270

Phe Gln His Leu Tyr Ala Pro Phe Ile Phe Gly Phe Met Thr Ile Asn
         275                 280                 285

Lys Val Ile Ser Gln Asp Val Gly Val Val Leu Arg Lys Arg Leu Phe
290                 295                 300

Gln Ile Asp Ala Asn Cys Arg Tyr Gly Ser Pro Trp Tyr Val Ala Arg
305                 310                 315                 320

Phe Trp Ile Met Lys Leu Leu Thr Thr Leu Tyr Met Val Ala Leu Pro
                 325                 330                 335

Met Tyr Met Gln Gly Pro Ala Gln Gly Leu Lys Leu Phe Phe Met Ala
             340                 345                 350

His Phe Thr Cys Gly Glu Val Leu Ala Thr Met Phe Ile Val Asn His
         355                 360                 365

Ile Ile Glu Gly Val Ser Tyr Ala Ser Lys Asp Ala Val Lys Gly Val
     370                 375                 380

Met Ala Pro Pro Arg Thr Val His Gly Val Thr Pro Met Gln Val Thr
385                 390                 395                 400

Gln Lys Ala Leu Ser Ala Ala Glu Ser Thr Lys Ser Asp Ala Asp Lys
                 405                 410                 415

Thr Thr Met Ile Pro Leu Asn Asp Trp Ala Ala Val Gln Cys Gln Thr
             420                 425                 430

Ser Val Asn Trp Ala Val Gly Ser Trp Phe Trp Asn His Phe Ser Gly
         435                 440                 445

Gly Leu Asn His Gln Ile Glu His His Cys Phe Pro Gln Asn Pro His
     450                 455                 460
```

```
Thr Val Asn Val Tyr Ile Ser Gly Ile Val Lys Glu Thr Cys Glu Glu
465                 470                 475                 480

Tyr Gly Val Pro Tyr Gln Ala Glu Ile Ser Leu Phe Ser Ala Tyr Phe
                485                 490                 495

Lys Met Leu Ser His Leu Arg Thr Leu Gly Asn Glu Asp Leu Thr Ala
            500                 505                 510

Trp Ser Thr
        515

<210> SEQ ID NO 20
<211> LENGTH: 515
<212> TYPE: PRT
<213> ORGANISM: Thraustochytrium aureum

<400> SEQUENCE: 20

Met Thr Val Gly Phe Asp Glu Thr Val Thr Met Asp Thr Val Arg Asn
1               5                   10                  15

His Asn Met Pro Asp Asp Ala Trp Cys Ala Ile His Gly Thr Val Tyr
            20                  25                  30

Asp Ile Thr Lys Phe Ser Lys Val His Pro Gly Gly Asp Ile Ile Met
            35                  40                  45

Leu Ala Ala Gly Lys Glu Ala Thr Ile Leu Phe Glu Thr Tyr His Ile
50                  55                  60

Lys Gly Val Pro Asp Ala Val Leu Arg Lys Tyr Lys Val Gly Lys Leu
65                  70                  75                  80

Pro Gln Gly Lys Lys Gly Glu Thr Ser His Met Pro Thr Gly Leu Asp
                85                  90                  95

Ser Ala Ser Tyr Tyr Ser Trp Asp Ser Glu Phe Tyr Arg Val Leu Arg
            100                 105                 110

Glu Arg Val Ala Lys Lys Leu Ala Glu Pro Gly Leu Met Gln Arg Ala
            115                 120                 125

Arg Met Glu Leu Trp Ala Lys Ala Ile Phe Leu Leu Ala Gly Phe Trp
130                 135                 140

Gly Ser Leu Tyr Ala Met Cys Val Leu Asp Pro His Gly Gly Ala Met
145                 150                 155                 160

Val Ala Ala Val Thr Leu Gly Val Phe Ala Ala Phe Val Gly Thr Cys
                165                 170                 175

Ile Gln His Asp Gly Ser His Gly Ala Phe Ser Lys Ser Arg Phe Met
            180                 185                 190

Asn Lys Ala Ala Gly Trp Thr Leu Asp Met Ile Gly Ala Ser Ala Met
            195                 200                 205

Thr Trp Glu Met Gln His Val Leu Gly His His Pro Tyr Thr Asn Leu
210                 215                 220

Ile Glu Met Glu Asn Gly Leu Ala Lys Val Lys Gly Ala Asp Val Asp
225                 230                 235                 240

Pro Lys Lys Val Asp Gln Glu Ser Asp Pro Asp Val Phe Ser Thr Tyr
                245                 250                 255

Pro Met Leu Arg Leu His Pro Trp His Arg Gln Arg Phe Tyr His Lys
            260                 265                 270

Phe Gln His Leu Tyr Ala Pro Leu Ile Phe Gly Phe Met Thr Ile Asn
            275                 280                 285

Lys Val Ile Ser Gln Asp Val Gly Val Leu Arg Lys Arg Leu Phe
290                 295                 300

Gln Ile Asp Ala Asn Cys Arg Tyr Gly Ser Pro Trp Asn Val Ala Arg
305                 310                 315                 320
```

```
Phe Trp Ile Met Lys Leu Leu Thr Thr Leu Tyr Met Val Ala Leu Pro
                325                 330                 335

Met Tyr Met Gln Gly Pro Ala Gln Gly Leu Lys Leu Phe Phe Met Ala
            340                 345                 350

His Phe Thr Cys Gly Glu Val Leu Ala Thr Met Phe Ile Val Asn His
        355                 360                 365

Ile Ile Glu Gly Val Ser Tyr Ala Ser Lys Asp Ala Val Lys Gly Val
    370                 375                 380

Met Ala Pro Pro Arg Thr Val His Gly Val Thr Pro Met Gln Val Thr
385                 390                 395                 400

Gln Lys Ala Leu Ser Ala Ala Glu Ser Thr Lys Ser Asp Ala Asp Lys
                405                 410                 415

Thr Thr Met Ile Pro Leu Asn Asp Trp Ala Ala Val Gln Cys Gln Thr
            420                 425                 430

Ser Val Asn Trp Ala Val Gly Ser Trp Phe Trp Asn His Phe Ser Gly
        435                 440                 445

Gly Leu Asn His Gln Ile Glu His His Cys Phe Pro Gln Asn Pro His
    450                 455                 460

Thr Val Asn Val Tyr Ile Ser Gly Ile Val Lys Glu Thr Cys Glu Glu
465                 470                 475                 480

Tyr Gly Val Pro Tyr Gln Ala Glu Ile Ser Leu Phe Ser Ala Tyr Phe
                485                 490                 495

Lys Met Leu Ser His Leu Arg Thr Leu Gly Asn Glu Asp Leu Thr Ala
            500                 505                 510

Trp Ser Thr
        515

<210> SEQ ID NO 21
<211> LENGTH: 515
<212> TYPE: PRT
<213> ORGANISM: Thraustochytrium aureum

<400> SEQUENCE: 21

Met Thr Val Gly Phe Asp Glu Thr Val Thr Met Asp Thr Val Arg Asn
 1               5                  10                  15

His Asn Met Pro Asp Asp Ala Trp Cys Ala Ile His Gly Thr Val Tyr
            20                  25                  30

Asp Ile Thr Lys Phe Ser Lys Val His Pro Gly Gly Asp Ile Ile Met
        35                  40                  45

Leu Ala Ala Gly Lys Glu Ala Thr Ile Leu Phe Glu Thr Tyr His Ile
    50                  55                  60

Lys Gly Val Pro Asp Ala Val Leu Arg Lys Tyr Lys Val Gly Lys Leu
65                  70                  75                  80

Pro Gln Gly Lys Lys Gly Glu Thr Ser His Met Pro Thr Gly Leu Asp
                85                  90                  95

Ser Ala Ser Tyr Tyr Ser Trp Asp Ser Glu Phe Tyr Arg Val Leu Arg
            100                 105                 110

Glu Arg Val Ala Lys Lys Leu Ala Glu Pro Gly Leu Met Gln Arg Ala
        115                 120                 125

Arg Met Glu Leu Trp Ala Lys Ala Ile Phe Leu Leu Ala Gly Phe Trp
    130                 135                 140

Gly Ser Leu Tyr Ala Met Cys Val Leu Asp Pro His Gly Gly Ala Met
145                 150                 155                 160

Val Ala Ala Val Thr Leu Gly Val Phe Ala Ala Phe Val Gly Thr Cys
```

|     |     |     |     | 165 |     |     |     | 170 |     |     |     | 175 |     |     |
| --- | --- | --- | --- | --- | --- | --- | --- | --- | --- | --- | --- | --- | --- | --- |
| Ile | Gln | His | Asp | Gly | Ser | His | Gly | Ala | Phe | Ser | Lys | Ser | Arg | Phe | Met
|     |     |     | 180 |     |     |     |     | 185 |     |     |     |     | 190 |

Asn Lys Ala Ala Gly Trp Thr Leu Asp Met Ile Gly Ala Ser Ala Met
        195                     200                     205

Thr Trp Glu Met Gln His Val Leu Gly His His Pro Tyr Thr Asn Leu
    210                     215                     220

Ile Glu Met Glu Asn Gly Leu Ala Lys Val Lys Gly Ala Asp Val Asp
225                     230                     235                     240

Pro Lys Lys Val Asp Gln Glu Ser Asp Pro Asp Val Phe Ser Thr Tyr
            245                     250                     255

Pro Met Leu Arg Leu His Pro Trp His Arg Gln Arg Phe Tyr His Lys
                260                     265                     270

Phe Gln His Leu Tyr Ala Pro Phe Ile Phe Gly Ser Met Thr Ile Asn
            275                     280                     285

Lys Val Ile Ser Gln Asp Val Gly Val Val Leu Arg Lys Arg Leu Phe
    290                     295                     300

Gln Ile Asp Ala Asn Cys Arg Tyr Gly Ser Pro Trp Tyr Val Ala Arg
305                     310                     315                     320

Phe Trp Ile Met Lys Leu Leu Thr Thr Leu Tyr Met Val Ala Leu Pro
                325                     330                     335

Met Tyr Met Gln Gly Pro Ala Gln Gly Leu Lys Leu Phe Phe Met Ala
            340                     345                     350

His Phe Thr Cys Gly Glu Val Leu Ala Thr Met Phe Ile Val Asn His
        355                     360                     365

Ile Ile Glu Gly Val Ser Tyr Ala Ser Lys Asp Ala Val Lys Gly Val
    370                     375                     380

Met Ala Pro Pro Arg Thr Val His Gly Val Thr Pro Met Gln Val Thr
385                     390                     395                     400

Gln Lys Ala Leu Ser Ala Ala Glu Ser Ala Lys Ser Asp Ala Asp Lys
                405                     410                     415

Thr Thr Met Ile Pro Leu Asn Asp Trp Ala Ala Val Gln Cys Gln Thr
            420                     425                     430

Ser Val Asn Trp Ala Val Gly Ser Trp Phe Trp Asn His Phe Ser Gly
    435                     440                     445

Gly Leu Asn His Gln Ile Glu His Cys Phe Pro Gln Asn Pro His
    450                     455                     460

Thr Val Asn Val Tyr Ile Ser Gly Ile Val Lys Glu Thr Cys Glu Glu
465                     470                     475                     480

Tyr Gly Val Pro Tyr Gln Ala Glu Ile Ser Leu Phe Ser Ala Tyr Phe
            485                     490                     495

Lys Met Leu Ser His Leu Arg Thr Leu Gly Asn Glu Asp Leu Thr Ala
                500                     505                     510

Trp Ser Thr
        515

<210> SEQ ID NO 22
<211> LENGTH: 879
<212> TYPE: DNA
<213> ORGANISM: Mus musculus

<400> SEQUENCE: 22
atggagcagc tgaaggcctt tgataatgaa gtcaatgctt tcttggacaa catgtttgga     60
ccacgagatt ctcgagttcg cgggtggttc ctgctggact cttaccttcc caccttcatc    120

```
ctcaccatca cgtacctgct ctcgatatgg ctgggtaaca agtacatgaa gaacaggcct    180
gctctgtctc tcagggcat cctcaccttg tataacctcg caatcacact tctttctgcg    240
tatatgctgg tggagctcat cctctccagc tgggaaggag gttacaactt gcagtgtcag    300
aatctcgaca gtgcaggaga aggtgatgtc cgggtagcca aggtcttgtg gtggtactac    360
ttctccaaac tagtggagtt cctggacacg attttctttg ttctacgaaa aaagaccaat    420
cagatcacct tccttcatgt ctatcaccac gcgtccatgt tcaacatctg gtggtgtgtt    480
ttgaactgga taccttgtgg tcaaagcttc tttggaccca ccctgaacag ctttatccac    540
attctcatgt actcctacta cggcctgtct gtgttcccgt ccatgcacaa gtacctttgg    600
tggaagaagt acctcacaca ggctcagctg gtgcagttcg tactcaccat cacgcacacg    660
ctgagtgccg tggtgaagcc ctgtggcttc ccctttggct gtctcatctt ccagtcttcc    720
tatatgatga cgctggtcat cctgttctta aacttctata ttcagacata ccggaaaaag    780
ccagtgaaga aagagctgca agagaaagaa gtgaagaatg gtttccccaa agcccactta    840
attgtggcta atggcatgac ggacaagaag gctcaataa                           879
```

<210> SEQ ID NO 23
<211> LENGTH: 292
<212> TYPE: PRT
<213> ORGANISM: Mus musculus

<400> SEQUENCE: 23

```
Met Glu Gln Leu Lys Ala Phe Asp Asn Glu Val Asn Ala Phe Leu Asp
 1               5                  10                  15

Asn Met Phe Gly Pro Arg Asp Ser Arg Val Arg Gly Trp Phe Leu Leu
            20                  25                  30

Asp Ser Tyr Leu Pro Thr Phe Ile Leu Thr Ile Thr Tyr Leu Leu Ser
        35                  40                  45

Ile Trp Leu Gly Asn Lys Tyr Met Lys Asn Arg Pro Ala Leu Ser Leu
    50                  55                  60

Arg Gly Ile Leu Thr Leu Tyr Asn Leu Ala Ile Thr Leu Leu Ser Ala
65                  70                  75                  80

Tyr Met Leu Val Glu Leu Ile Leu Ser Ser Trp Glu Gly Gly Tyr Asn
                85                  90                  95

Leu Gln Cys Gln Asn Leu Asp Ser Ala Gly Glu Gly Asp Val Arg Val
           100                 105                 110

Ala Lys Val Leu Trp Trp Tyr Tyr Phe Ser Lys Leu Val Glu Phe Leu
       115                 120                 125

Asp Thr Ile Phe Phe Val Leu Arg Lys Lys Thr Asn Gln Ile Thr Phe
   130                 135                 140

Leu His Val Tyr His His Ala Ser Met Phe Asn Ile Trp Trp Cys Val
145                 150                 155                 160

Leu Asn Trp Ile Pro Cys Gly Gln Ser Phe Gly Pro Thr Leu Asn
                165                 170                 175

Ser Phe Ile His Ile Leu Met Tyr Ser Tyr Tyr Gly Leu Ser Val Phe
            180                 185                 190

Pro Ser Met His Lys Tyr Leu Trp Trp Lys Lys Tyr Leu Thr Gln Ala
        195                 200                 205

Gln Leu Val Gln Phe Val Leu Thr Ile Thr His Thr Leu Ser Ala Val
    210                 215                 220

Val Lys Pro Cys Gly Phe Pro Phe Gly Cys Leu Ile Phe Gln Ser Ser
225                 230                 235                 240
```

```
Tyr Met Met Thr Leu Val Ile Leu Phe Leu Asn Phe Tyr Ile Gln Thr
                245                 250                 255

Tyr Arg Lys Lys Pro Val Lys Lys Glu Leu Gln Glu Lys Glu Val Lys
            260                 265                 270

Asn Gly Phe Pro Lys Ala His Leu Ile Val Ala Asn Gly Met Thr Asp
        275                 280                 285

Lys Lys Ala Gln
    290

<210> SEQ ID NO 24
<211> LENGTH: 754
<212> TYPE: DNA
<213> ORGANISM: Schizochytrium aggregatum

<400> SEQUENCE: 24
ccagtgtgct ggaattcagg tactactact acaccatact tacacgaacc tgatcgagat    60
ggagaacggc acccaaaagg tcacccacgc cgacgtcgac cccaagaagg ccgaccagga   120
gagcgacccg gacgtcttca gcacctaccc catgctccgt ctgcacccgt ggcaccgcaa   180
gcgcttctac caccgcttcc agcacctgta cgcgccgctg ctcttcggtt tcatgaccat   240
caacaaggtg atcacccagg atgtgggagt tgtcctcagc aagcgtctgt ttcagatcga   300
tgccaactgc cgttacgcca gcaagtcgta cgttgcgcgc ttctggatca tgaagctgct   360
caccgtcctc tacatggtcg ccctccccgt gtacacccag ggccttgtcg acgggctcaa   420
gctcttcttc atcgcccact tttcgtgcgg cgagctgctg gccaccatgt tcatcgtcaa   480
ccacatcatc gagggcgtct cgtacgcctc caaggactct gtcaagggca ccatggcgcc   540
gccgcgcacg gtgcacggcg tgaccccgat gcatgacacc cgcgacgcgc tcggcaagga   600
gaaggcagcc accaagcacg tgccgctcaa cgactgggcc gcggtccagt gccagacctc   660
ggtcaactgg tcgatcggct cgtggttctg gaaccacttc tccggcgggc tcaaccacca   720
gatcgagcac cacctttttcc ccatgatgat gatg                              754

<210> SEQ ID NO 25
<211> LENGTH: 251
<212> TYPE: PRT
<213> ORGANISM: Schizochytrium aggregatum

<400> SEQUENCE: 25

Gln Cys Ala Gly Ile Gln Val Leu Leu Leu His His Thr Tyr Thr Asn
  1               5                  10                  15

Leu Ile Glu Met Glu Asn Gly Thr Gln Lys Val Thr His Ala Asp Val
                20                  25                  30

Asp Pro Lys Lys Ala Asp Gln Glu Ser Asp Pro Asp Val Phe Ser Thr
            35                  40                  45

Tyr Pro Met Leu Arg Leu His Pro Trp His Arg Lys Arg Phe Tyr His
        50                  55                  60

Arg Phe Gln His Leu Tyr Ala Pro Leu Leu Phe Gly Phe Met Thr Ile
 65                  70                  75                  80

Asn Lys Val Ile Thr Gln Asp Val Gly Val Val Leu Ser Lys Arg Leu
                85                  90                  95

Phe Gln Ile Asp Ala Asn Cys Arg Tyr Ala Ser Lys Ser Tyr Val Ala
            100                 105                 110

Arg Phe Trp Ile Met Lys Leu Leu Thr Val Leu Tyr Met Val Ala Leu
        115                 120                 125
```

```
Pro Val Tyr Thr Gln Gly Leu Val Asp Gly Leu Lys Leu Phe Phe Ile
    130                 135                 140

Ala His Phe Ser Cys Gly Glu Leu Leu Ala Thr Met Phe Ile Val Asn
145                 150                 155                 160

His Ile Ile Glu Gly Val Ser Tyr Ala Ser Lys Asp Ser Val Lys Gly
                165                 170                 175

Thr Met Ala Pro Pro Arg Thr Val His Gly Val Thr Pro Met His Asp
            180                 185                 190

Thr Arg Asp Ala Leu Gly Lys Glu Lys Ala Ala Thr Lys His Val Pro
        195                 200                 205

Leu Asn Asp Trp Ala Ala Val Gln Cys Gln Thr Ser Val Asn Trp Ser
    210                 215                 220

Ile Gly Ser Trp Phe Trp Asn His Phe Ser Gly Gly Leu Asn His Gln
225                 230                 235                 240

Ile Glu His His Leu Phe Pro Met Met Met Met
                245                 250
```

<210> SEQ ID NO 26
<211> LENGTH: 27
<212> TYPE: DNA
<213> ORGANISM: Artificial Sequence
<220> FEATURE:
<223> OTHER INFORMATION: Primer RO1240

<400> SEQUENCE: 26
ccctcgatga tgtggttgac gatgaac                                27

<210> SEQ ID NO 27
<211> LENGTH: 26
<212> TYPE: DNA
<213> ORGANISM: Artificial Sequence
<220> FEATURE:
<223> OTHER INFORMATION: 5' Nested Primer RO1239

<400> SEQUENCE: 27
cggagcatgg ggtaggtgct gaagac                                 26

<210> SEQ ID NO 28
<211> LENGTH: 24
<212> TYPE: DNA
<213> ORGANISM: Artificial Sequence
<220> FEATURE:
<223> OTHER INFORMATION: Primer RO1236

<400> SEQUENCE: 28
ccaactgccg ttacgccagc aagt                                   24

<210> SEQ ID NO 29
<211> LENGTH: 28
<212> TYPE: DNA
<213> ORGANISM: Artificial Sequence
<220> FEATURE:
<223> OTHER INFORMATION: 3' Nested Primer RO1237

<400> SEQUENCE: 29
caagctcttc ttcatcgccc acttttcg                               28

<210> SEQ ID NO 30
<211> LENGTH: 23
<212> TYPE: DNA
<213> ORGANISM: Artificial Sequence
<220> FEATURE:
<223> OTHER INFORMATION: Primer RO1240 and GeneRacer 5' Primer

```
<400> SEQUENCE: 30
cgactggagc acgaggacac tga                                              23

<210> SEQ ID NO 31
<211> LENGTH: 25
<212> TYPE: DNA
<213> ORGANISM: Artificial Sequence
<220> FEATURE:
<223> OTHER INFORMATION: Primer RO1236 and GeneRacer 3' Primer

<400> SEQUENCE: 31
gctgtcaacg atacgctacg taacg                                            25

<210> SEQ ID NO 32
<211> LENGTH: 26
<212> TYPE: DNA
<213> ORGANISM: Artificial Sequence
<220> FEATURE:
<223> OTHER INFORMATION: Nested Primer RO1239 and GeneRacer Nested 5'
      Primer

<400> SEQUENCE: 32
ggacactgac atggactgaa ggagta                                           26

<210> SEQ ID NO 33
<211> LENGTH: 23
<212> TYPE: DNA
<213> ORGANISM: Artificial Sequence
<220> FEATURE:
<223> OTHER INFORMATION: Nested Primer RO1237 and GeneRacer Nested 3'
      Primer

<400> SEQUENCE: 33
cgctacgtaa cggcatgaca gtg                                              23

<210> SEQ ID NO 34
<211> LENGTH: 34
<212> TYPE: DNA
<213> ORGANISM: Artificial Sequence
<220> FEATURE:
<223> OTHER INFORMATION: Primer RO1241

<400> SEQUENCE: 34
gatatcgaat tcatgacggt gggcggcgat gagg                                  34

<210> SEQ ID NO 35
<211> LENGTH: 34
<212> TYPE: DNA
<213> ORGANISM: Artificial Sequence
<220> FEATURE:
<223> OTHER INFORMATION: Primer RO1242

<400> SEQUENCE: 35
gtacttaagc tttcacttgg acttggggtg gtcc                                  34

<210> SEQ ID NO 36
<211> LENGTH: 1530
<212> TYPE: DNA
<213> ORGANISM: Schizochytrium aggregatum

<400> SEQUENCE: 36
atgacggtgg gcggcgatga ggtgtacagc atggcgcagg tgcgcgacca caacaccccg      60
gacgacgcct ggtgcgccat ccacggcgag gtgtacgagc tgaccaagtt cgcccgcacc     120
```

-continued

```
caccccgggg gggacatcat cttgctggcc gccggcaagg aggccaccat cctgttcgag    180
acgtaccacg tgcgcccat ctccgacgcg gtcctgcgca gtaccgcat cggcaagctc     240
gccgccgccg gcaaggatga gccggccaac gacagcacct actacagctg gacagcgac    300
ttttacaagg tgctccgcca gcgtgtcgtg gcgcgcctcg aggagcgcaa gatcgcccgc   360
cgcggcggcc ccgagatctg gatcaaggcc gccatcctcg tcagcggctt ctggtccatg   420
ctctacctca tgtgcaccct ggacccgaac cgcggcgcca tcctggccgc catcgcgctg   480
ggcatcgtcg ccgccttcgt cggcacgtgc attcagcacg acggcaacca cggcgcgttc   540
gccttctctc cgttcatgaa caagctctct ggctggacgc tcgacatgat cggcgccagt   600
gccatgacct gggagatgca gcacgtgctg gccaccacc cgtacaccaa cctgatcgag    660
atggagaacg gcacccaaaa ggtcacccac gccgacgtcg accccaagaa ggccgaccag   720
gagagcgacc cggacgtctt cagcacctac cccatgctcc gtctgcaccc gtggcaccgc   780
aagcgcttct accaccgctt ccagcacctg tacgcgccgc tgctcttcgg tttcatgacc   840
atcaacaagg tgatcaccca ggatgtggga gttgtcctca gcaagcgtct gtttcagatc   900
gatgccaact gccgttacgc cagcaagtcg tacgttgcgc gcttctggat catgaagctg   960
ctcaccgtcc tctacatggt cgccctcccc gtgtacaccc agggccttgt cgacgggctc   1020
aagctcttct tcatcgccca cttttcgtgc ggcgagctgc tggccaccat gttcatcgtc   1080
aaccacatca tcgagggcgt ctcgtacgcc tccaaggact ctgtcaaggg caccatggcg   1140
ccgccgcgca cggtgcacgg cgtgaccccg atgcatgaca cccgcgacgc gctcggcaag   1200
gagaaggcag ccaccaagca cgtgccgctc aacgactggg ccgcggtcca gtgccagacc   1260
tcggtcaact ggtcgatcgg ctcgtggttc tggaaccact ctccggcgg gctcaaccac    1320
cagatcgagc accacctctt ccccggcctc acccacacca cctacgtgta cattcaggat   1380
gtggtgcagg cgacgtgcgc cgagtacggg gtcccgtacc agtcggagca gagcctcttc   1440
tccgcctact tcaagatgct ctcccacctt cgggcgctcg gcaacgagcc gatgccctcg   1500
tgggagaagg accaccccaa gtccaagtga                                    1530
```

<210> SEQ ID NO 37
<211> LENGTH: 509
<212> TYPE: PRT
<213> ORGANISM: Schizochytrium aggregatum

<400> SEQUENCE: 37

```
Met Thr Val Gly Gly Asp Glu Val Tyr Ser Met Ala Gln Val Arg Asp
  1               5                  10                  15

His Asn Thr Pro Asp Asp Ala Trp Cys Ala Ile His Gly Glu Val Tyr
                 20                  25                  30

Glu Leu Thr Lys Phe Ala Arg Thr His Pro Gly Gly Asp Ile Ile Leu
             35                  40                  45

Leu Ala Gly Lys Glu Ala Thr Ile Leu Phe Glu Thr Tyr His Val
         50                  55                  60

Arg Pro Ile Ser Asp Ala Val Leu Arg Lys Tyr Arg Ile Gly Lys Leu
 65                  70                  75                  80

Ala Ala Ala Gly Lys Asp Glu Pro Ala Asn Asp Ser Thr Tyr Tyr Ser
                 85                  90                  95

Trp Asp Ser Asp Phe Tyr Lys Val Leu Arg Gln Arg Val Val Ala Arg
                100                 105                 110

Leu Glu Glu Arg Lys Ile Ala Arg Arg Gly Gly Pro Glu Ile Trp Ile
            115                 120                 125
```

```
Lys Ala Ala Ile Leu Val Ser Gly Phe Trp Ser Met Leu Tyr Leu Met
        130                 135                 140

Cys Thr Leu Asp Pro Asn Arg Gly Ala Ile Leu Ala Ala Ile Ala Leu
145                 150                 155                 160

Gly Ile Val Ala Ala Phe Val Gly Thr Cys Ile Gln His Asp Gly Asn
                    165                 170                 175

His Gly Ala Phe Ala Phe Ser Pro Phe Met Asn Lys Leu Ser Gly Trp
            180                 185                 190

Thr Leu Asp Met Ile Gly Ala Ser Ala Met Thr Trp Glu Met Gln His
        195                 200                 205

Val Leu Gly His His Pro Tyr Thr Asn Leu Ile Glu Met Glu Asn Gly
    210                 215                 220

Thr Gln Lys Val Thr His Ala Asp Val Asp Pro Lys Lys Ala Asp Gln
225                 230                 235                 240

Glu Ser Asp Pro Asp Val Phe Ser Thr Tyr Pro Met Leu Arg Leu His
                    245                 250                 255

Pro Trp His Arg Lys Arg Phe Tyr His Arg Phe Gln His Leu Tyr Ala
            260                 265                 270

Pro Leu Leu Phe Gly Phe Met Thr Ile Asn Lys Val Ile Thr Gln Asp
        275                 280                 285

Val Gly Val Val Leu Ser Lys Arg Leu Phe Gln Ile Asp Ala Asn Cys
    290                 295                 300

Arg Tyr Ala Ser Lys Ser Tyr Val Ala Arg Phe Trp Ile Met Lys Leu
305                 310                 315                 320

Leu Thr Val Leu Tyr Met Val Ala Leu Pro Val Tyr Thr Gln Gly Leu
                    325                 330                 335

Val Asp Gly Leu Lys Leu Phe Phe Ile Ala His Phe Ser Cys Gly Glu
            340                 345                 350

Leu Leu Ala Thr Met Phe Ile Val Asn His Ile Ile Glu Gly Val Ser
        355                 360                 365

Tyr Ala Ser Lys Asp Ser Val Lys Gly Thr Met Ala Pro Pro Arg Thr
    370                 375                 380

Val His Gly Val Thr Pro Met His Asp Thr Arg Asp Ala Leu Gly Lys
385                 390                 395                 400

Glu Lys Ala Ala Thr Lys His Val Pro Leu Asn Asp Trp Ala Ala Val
                    405                 410                 415

Gln Cys Gln Thr Ser Val Asn Trp Ser Ile Gly Ser Trp Phe Trp Asn
            420                 425                 430

His Phe Ser Gly Gly Leu Asn His Gln Ile Glu His His Leu Phe Pro
        435                 440                 445

Gly Leu Thr His Thr Thr Tyr Val Tyr Ile Gln Asp Val Val Gln Ala
    450                 455                 460

Thr Cys Ala Glu Tyr Gly Val Pro Tyr Gln Ser Glu Gln Ser Leu Phe
465                 470                 475                 480

Ser Ala Tyr Phe Lys Met Leu Ser His Leu Arg Ala Leu Gly Asn Glu
                    485                 490                 495

Pro Met Pro Ser Trp Glu Lys Asp His Pro Lys Ser Lys
            500                 505

<210> SEQ ID NO 38
<211> LENGTH: 32
<212> TYPE: DNA
<213> ORGANISM: Artificial Sequence
<220> FEATURE:
```

-continued

<223> OTHER INFORMATION: Primer RO1201

<400> SEQUENCE: 38
cgtgttcgct gcctttgtcg aacttgcat cc                                    32

<210> SEQ ID NO 39
<211> LENGTH: 33
<212> TYPE: DNA
<213> ORGANISM: Artificial Sequence
<220> FEATURE:
<223> OTHER INFORMATION: Primer RO1202

<400> SEQUENCE: 39
ttgacaataa acatggaggc gaggacctct ccg                                   33

<210> SEQ ID NO 40
<211> LENGTH: 30
<212> TYPE: DNA
<213> ORGANISM: Artificial Sequence
<220> FEATURE:
<223> OTHER INFORMATION: Primer RO1210

<400> SEQUENCE: 40
gctggttgga ctttggacat gattggatcc                                       30

<210> SEQ ID NO 41
<211> LENGTH: 30
<212> TYPE: DNA
<213> ORGANISM: Artificial Sequence
<220> FEATURE:
<223> OTHER INFORMATION: Primer RO1211

<400> SEQUENCE: 41
tacattggca ggccaaccat gtagagaacg                                       30

<210> SEQ ID NO 42
<211> LENGTH: 30
<212> TYPE: DNA
<213> ORGANISM: Artificial Sequence
<220> FEATURE:
<223> OTHER INFORMATION: Internal Primer RO1214

<400> SEQUENCE: 42
ggattcaatc atgtccaaag tccaaccagc                                       30

<210> SEQ ID NO 43
<211> LENGTH: 34
<212> TYPE: DNA
<213> ORGANISM: Artificial Sequence
<220> FEATURE:
<223> OTHER INFORMATION: 5' Primer RO1223

<400> SEQUENCE: 43
tctgatgaat tcatgacggc cggatttgaa gaag                                  34

<210> SEQ ID NO 44
<211> LENGTH: 35
<212> TYPE: DNA
<213> ORGANISM: Artificial Sequence
<220> FEATURE:
<223> OTHER INFORMATION: 3' Primer RO1224

<400> SEQUENCE: 44
gtctagctcg agttagttct tgtcccaggc aggca                                 35

<210> SEQ ID NO 45
<211> LENGTH: 1542
<212> TYPE: DNA
<213> ORGANISM: Thraustochytrium aureum

<400> SEQUENCE: 45

```
atgacggccg gatttgaaga agtgatcacc atgaagcagg tgaaggaccg gaatacgccg      60
gacgatgcgt ggtgcgtggt gcatggcaag gtgtacgaca tcaccaagtt caagaacgct     120
caccccggtg gagatataat catgttggcg gctggcaagg acgccaccat cctgttcgag     180
acttaccaca tccgcggtgt gcccgatgcc gtgttgcgca agtatcagat cggcaaactt     240
ccggacggaa agaacaaaga gggcggcaac ggcctcgata gcgcctcgta ctactcctgg     300
gacagcgagt tttaccgcgt ccttcgcgag gcgtcttga agcgcctgaa cgagctcaag     360
ctgtccagac gcggaggctt cgagatttgg gccaaggcta tctttctctt gaccggcttc     420
tggtcttgcc tctacctcat gtgcacactc aacccaaatg gcttgcgat tcctgccgcc     480
atgatgttgg gaatctttgc tgccttcgta ggaacctgca ttcagcacga cgggaatcac     540
ggtgcgttcg cccaatcttc gtggcttaac aaggccgctg ttggactttt ggacatgatt     600
ggatccagcg ccatgaccctg ggagatgcag cacgtgcttg acatcatcc gtacaccaac     660
ttgattgaaa tggagaatgg caatcaaaag gtctccggca agcctgttga caccaagact     720
gtcgaccagg agagcgaccc tgatgtcttt agcacctacc ctatgcttcg ccttcacccct     780
tggcacagca aaaagtggta ccacaaatac cagcacatct atgcaccatt catctttggg     840
ttcatgacca tcaacaaggt cattgcacag gacgttggcg ttatcacacg caagcgtctc     900
ttccagattg acgccaactg ccgctacgct tctccgactt acgtcgctcg cttctggatc     960
atgaaggttc ttaccgttct ctacatggtt ggcctgccaa tgtacatgca aggtccatgg    1020
gagggtctca gttgttctt tattgcgcac tttacttgcg gcgagctgct ggccacaatg    1080
ttcatcgtaa accacatcat cgagggtgtc agctacgcaa gcaaagatgc catcaagggc    1140
gagatggctc caccgaaaac ggtccgcggt gtcaccccaa tgcacgagac gcaaaaggtt    1200
ctcgaccagc gcgagaaaga catggacgaa acttctaaga gagccgcat ccctctcaac    1260
gactgggccg ctgtacagtg ccagaccacc gtgaactggg ctatcggttc ttggttctgg    1320
aaccactttt ccgggggcct caatcatcag attgagcatc atctgttccc cggcttgact    1380
cacaccacct atgttcactt tcacgatgtg gtcaaagata cttgcgctga gtacggggtt    1440
ccataccagc acgaggagag tctatacact gcctacttta agatgttgaa tcatctcaag    1500
acccctaggca acgagccaat gcctgcctgg gacaagaact aa                      1542
```

<210> SEQ ID NO 46
<211> LENGTH: 513
<212> TYPE: PRT
<213> ORGANISM: Thraustochytrium aureum

<400> SEQUENCE: 46

```
Met Thr Ala Gly Phe Glu Glu Val Ile Thr Met Lys Gln Val Lys Asp
  1               5                  10                  15

Arg Asn Thr Pro Asp Asp Ala Trp Cys Val Val His Gly Lys Val Tyr
             20                  25                  30

Asp Ile Thr Lys Phe Lys Asn Ala His Pro Gly Gly Asp Ile Ile Met
         35                  40                  45

Leu Ala Ala Gly Lys Asp Ala Thr Ile Leu Phe Glu Thr Tyr His Ile
     50                  55                  60
```

-continued

```
Arg Gly Val Pro Asp Ala Val Leu Arg Lys Tyr Gln Ile Gly Lys Leu
 65                  70                  75                  80

Pro Asp Gly Lys Asn Lys Glu Gly Gly Asn Gly Leu Asp Ser Ala Ser
                 85                  90                  95

Tyr Tyr Ser Trp Asp Ser Glu Phe Tyr Arg Val Leu Arg Glu Arg Val
            100                 105                 110

Leu Lys Arg Leu Asn Glu Leu Lys Leu Ser Arg Arg Gly Gly Phe Glu
        115                 120                 125

Ile Trp Ala Lys Ala Ile Phe Leu Leu Thr Gly Phe Trp Ser Cys Leu
130                 135                 140

Tyr Leu Met Cys Thr Leu Asn Pro Asn Gly Leu Ala Ile Pro Ala Ala
145                 150                 155                 160

Met Met Leu Gly Ile Phe Ala Ala Phe Val Gly Thr Cys Ile Gln His
                165                 170                 175

Asp Gly Asn His Gly Ala Phe Ala Gln Ser Ser Trp Leu Asn Lys Ala
            180                 185                 190

Ala Gly Trp Thr Leu Asp Met Ile Gly Ser Ser Ala Met Thr Trp Glu
        195                 200                 205

Met Gln His Val Leu Gly His His Pro Tyr Thr Asn Leu Ile Glu Met
210                 215                 220

Glu Asn Gly Asn Gln Lys Val Ser Gly Lys Pro Val Asp Thr Lys Thr
225                 230                 235                 240

Val Asp Gln Glu Ser Asp Pro Asp Val Phe Ser Thr Tyr Pro Met Leu
                245                 250                 255

Arg Leu His Pro Trp His Ser Lys Lys Trp Tyr His Lys Tyr Gln His
            260                 265                 270

Ile Tyr Ala Pro Phe Ile Phe Gly Phe Met Thr Ile Asn Lys Val Ile
        275                 280                 285

Ala Gln Asp Val Gly Val Ile Thr Arg Lys Arg Leu Phe Gln Ile Asp
290                 295                 300

Ala Asn Cys Arg Tyr Ala Ser Pro Thr Tyr Val Ala Arg Phe Trp Ile
305                 310                 315                 320

Met Lys Val Leu Thr Val Leu Tyr Met Val Gly Leu Pro Met Tyr Met
                325                 330                 335

Gln Gly Pro Trp Glu Gly Leu Lys Leu Phe Phe Ile Ala His Phe Thr
            340                 345                 350

Cys Gly Glu Leu Leu Ala Thr Met Phe Ile Val Asn His Ile Ile Glu
        355                 360                 365

Gly Val Ser Tyr Ala Ser Lys Asp Ala Ile Lys Gly Glu Met Ala Pro
370                 375                 380

Pro Lys Thr Val Arg Gly Val Thr Pro Met His Glu Thr Gln Lys Val
385                 390                 395                 400

Leu Asp Gln Arg Glu Lys Asp Met Asp Glu Thr Ser Lys Lys Ser Arg
                405                 410                 415

Ile Pro Leu Asn Asp Trp Ala Ala Val Gln Cys Gln Thr Thr Val Asn
            420                 425                 430

Trp Ala Ile Gly Ser Trp Phe Trp Asn His Phe Ser Gly Gly Leu Asn
        435                 440                 445

His Gln Ile Glu His His Leu Phe Pro Gly Leu Thr His Thr Thr Tyr
450                 455                 460

Val His Phe His Asp Val Val Lys Asp Thr Cys Ala Glu Tyr Gly Val
465                 470                 475                 480

Pro Tyr Gln His Glu Glu Ser Leu Tyr Thr Ala Tyr Phe Lys Met Leu
```

```
                    485              490              495
Asn His Leu Lys Thr Leu Gly Asn Glu Pro Met Pro Ala Trp Asp Lys
            500              505              510
Asn
```

<210> SEQ ID NO 47
<211> LENGTH: 23
<212> TYPE: DNA
<213> ORGANISM: Artificial Sequence
<220> FEATURE:
<223> OTHER INFORMATION: M13 Forward Primer

<400> SEQUENCE: 47
agcggataac aatttcacac agg                                          23

<210> SEQ ID NO 48
<211> LENGTH: 26
<212> TYPE: DNA
<213> ORGANISM: Artificial Sequence
<220> FEATURE:
<223> OTHER INFORMATION: Primer RO1270

<400> SEQUENCE: 48
cacctggctc gagtcgacga tgatgg                                       26

<210> SEQ ID NO 49
<211> LENGTH: 25
<212> TYPE: DNA
<213> ORGANISM: Artificial Sequence
<220> FEATURE:
<223> OTHER INFORMATION: Primer RO1286

<400> SEQUENCE: 49
cgtacccggt gcaatagaag gtgag                                        25

<210> SEQ ID NO 50
<211> LENGTH: 26
<212> TYPE: DNA
<213> ORGANISM: Artificial Sequence
<220> FEATURE:
<223> OTHER INFORMATION: Primer RO1287

<400> SEQUENCE: 50
ccatcatcgt cgactcgagc caggtg                                       26

<210> SEQ ID NO 51
<211> LENGTH: 26
<212> TYPE: DNA
<213> ORGANISM: Artificial Sequence
<220> FEATURE:
<223> OTHER INFORMATION: Primer RO1288

<400> SEQUENCE: 51
tgtggagcca tgtggtgctc gatctg                                       26

<210> SEQ ID NO 52
<211> LENGTH: 42
<212> TYPE: DNA
<213> ORGANISM: Artificial Sequence
<220> FEATURE:
<223> OTHER INFORMATION: Forward Primer RO1400

<400> SEQUENCE: 52
tcaacagaat tcatgtgcaa cgcggcgcag gtcgagacgc ag                     42

<210> SEQ ID NO 53
<211> LENGTH: 42
<212> TYPE: DNA
<213> ORGANISM: Artificial Sequence
<220> FEATURE:
<223> OTHER INFORMATION: Reverse Primer RO1401

<400> SEQUENCE: 53
aaaagaaagc ttttagtccg ccttgaccgt gtcgaccaaa gc                               42

<210> SEQ ID NO 54
<211> LENGTH: 1301
<212> TYPE: DNA
<213> ORGANISM: Isochrysis galbana

<400> SEQUENCE: 54
atgtgcaacg cggcgcaggt cgagacgcag gccttgcgcg ccaaggaggc ggcaaaaccg            60
acgtggacga agattcatgg cgcacagtc gacgtggaga cgttccgcca cccaggcggc           120
aacatcctcg atttgttcct gggcatggag ccacaactgc ctttgagacg ttccacggtc          180
accacaaggg agcatggaag atgctcaaga cgctgcccga aggaggtc gccgccgccg            240 acattcccgc gcagaaggag gagcacgtgg ccgagatgac acgcctcatg gcctcatggc          300
gcgagcgcgg gctgttcaag ccgcgtcccg tcgcctcatc catctatggc ctgtgcgtga          360
tcttcgccat cgcggcatcg gtcgcgtgcg ctccgtacgc gccagtgctg gctggcatcg          420
cggtgggcac ctgctgggct cagtgcggct tcttgcagca catgggcggc caccgggagt          480
gggggcgcac ttggtcgttt gcgtttcagc atctgtttga aggcctgctc aagggcggct          540
cggcctcgtg gtggcgcaac cgccacaaca agcaccatgc caagaccaac gtgctcggcg          600
aggacggcga cctgcgcacc acaccttct tcgcatggga ccctactctg gccaagaaag           660
tgcccgactg gtctctgcgc acgcaagcct tcacctttct gccagcactg ggagcttacg          720
tcttcgtctt tgccttcacg gtacgcaagt acagtgtggt gaagcgtctc tggcacgagg          780
tcgccctgat ggtggcccac tacgctctct tttcctgggc gctcagcgcc gccgcgcct            840 ccctcagctc cggcctcacc ttctattgca ccgggtacgc ctggcagggc atctacctcg          900
gcttcttctt cggcctatcg cactttgcgg tggagcgcgt gccgtcgacc gccacctggc          960
tcgagtcgac gatgatgggc accgttgact ggggcggctc ctccgccttc tgcggctacc         1020
tctccggctt cctcaatatc cagatcgagc accacatggc tccacaaatg ccaatggaga         1080
acctgcgcca gatccgggcc gactgcaagg ccgcggccca caagttcggg ctgccgtacc         1140
gcgagctgac attcgtcgcg gcgaccaagc tcatgatgag cggcctctac cggaccggca         1200
aggacgagct caagctgcgc gcggaccgcc gcaagttcac gagggcacag gcgtacatgg         1260
gcgccgccag cgctttggtc gacacgctca aggcggacta a                             1301

<210> SEQ ID NO 55
<211> LENGTH: 433
<212> TYPE: PRT
<213> ORGANISM: Isochrysis galbana

<400> SEQUENCE: 55

Met Cys Asn Ala Ala Gln Val Glu Thr Gln Ala Leu Arg Ala Lys Glu
 1               5                  10                  15

Ala Ala Lys Pro Thr Trp Thr Lys Ile His Gly Arg Thr Val Asp Val
            20                  25                  30

Glu Thr Phe Arg His Pro Gly Gly Asn Ile Leu Asp Leu Phe Leu Gly

-continued

```
                35                  40                  45
Met Asp Ala Thr Thr Ala Phe Glu Thr Phe His Gly His His Lys Gly
 50                  55                  60
Ala Trp Lys Met Leu Lys Thr Leu Pro Glu Lys Glu Val Ala Ala Ala
 65                  70                  75                  80
Asp Ile Pro Ala Gln Lys Glu His Val Ala Glu Met Thr Arg Leu
                 85                  90                  95
Met Ala Ser Trp Arg Glu Arg Gly Leu Phe Lys Pro Arg Pro Val Ala
                100                 105                 110
Ser Ser Ile Tyr Gly Leu Cys Val Ile Phe Ala Ile Ala Ala Ser Val
                115                 120                 125
Ala Cys Ala Pro Tyr Ala Pro Val Leu Ala Gly Ile Ala Val Gly Thr
130                 135                 140
Cys Trp Ala Gln Cys Gly Phe Leu Gln His Met Gly His Arg Glu
145                 150                 155                 160
Trp Gly Arg Thr Trp Ser Phe Ala Phe Gln His Leu Phe Glu Gly Leu
                165                 170                 175
Leu Lys Gly Gly Ser Ala Ser Trp Trp Arg Asn Arg His Asn Lys His
                180                 185                 190
His Ala Lys Thr Asn Val Leu Gly Glu Asp Gly Asp Leu Arg Thr Thr
                195                 200                 205
Pro Phe Phe Ala Trp Asp Pro Thr Leu Ala Lys Lys Val Pro Asp Trp
210                 215                 220
Ser Leu Arg Thr Gln Ala Phe Thr Phe Leu Pro Ala Leu Gly Ala Tyr
225                 230                 235                 240
Val Phe Val Phe Ala Phe Thr Val Arg Lys Tyr Ser Val Val Lys Arg
                245                 250                 255
Leu Trp His Glu Val Ala Leu Met Val Ala His Tyr Ala Leu Phe Ser
                260                 265                 270
Trp Ala Leu Ser Ala Ala Gly Ala Ser Leu Ser Ser Gly Leu Thr Phe
                275                 280                 285
Tyr Cys Thr Gly Tyr Ala Trp Gln Gly Ile Tyr Leu Gly Phe Phe Phe
                290                 295                 300
Gly Leu Ser His Phe Ala Val Glu Arg Val Pro Ser Thr Ala Thr Trp
305                 310                 315                 320
Leu Glu Ser Thr Met Met Gly Thr Val Asp Trp Gly Gly Ser Ser Ala
                325                 330                 335
Phe Cys Gly Tyr Leu Ser Gly Phe Leu Asn Ile Gln Ile Glu His His
                340                 345                 350
Met Ala Pro Gln Met Pro Met Glu Asn Leu Arg Gln Ile Arg Ala Asp
                355                 360                 365
Cys Lys Ala Ala Ala His Lys Phe Gly Leu Pro Tyr Arg Glu Leu Thr
370                 375                 380
Phe Val Ala Ala Thr Lys Leu Met Met Ser Gly Leu Tyr Arg Thr Gly
385                 390                 395                 400
Lys Asp Glu Leu Lys Leu Arg Ala Asp Arg Lys Phe Thr Arg Ala
                405                 410                 415
Gln Ala Tyr Met Gly Ala Ala Ser Ala Leu Val Asp Thr Leu Lys Ala
                420                 425                 430
Asp
```

<210> SEQ ID NO 56
<211> LENGTH: 14

```
<212> TYPE: PRT
<213> ORGANISM: Artificial Sequence
<220> FEATURE:
<223> OTHER INFORMATION: Protein Motif #1

<400> SEQUENCE: 56

Val Tyr Asp Val Thr Glu Trp Val Lys Arg His Pro Gly Gly
 1               5                  10

<210> SEQ ID NO 57
<211> LENGTH: 15
<212> TYPE: PRT
<213> ORGANISM: Artificial Sequence
<220> FEATURE:
<223> OTHER INFORMATION: Protein Motif #2

<400> SEQUENCE: 57

Gly Ala Ser Ala Asn Trp Trp Lys His Gln His Asn Val His His
 1               5                  10                  15

<210> SEQ ID NO 58
<211> LENGTH: 12
<212> TYPE: PRT
<213> ORGANISM: Artificial Sequence
<220> FEATURE:
<223> OTHER INFORMATION: Protein Motif #3

<400> SEQUENCE: 58

Asn Tyr Gln Ile Glu His His Leu Phe Pro Thr Met
 1               5                  10

<210> SEQ ID NO 59
<211> LENGTH: 6
<212> TYPE: PRT
<213> ORGANISM: Thraustochytrium aureum

<400> SEQUENCE: 59

Gln His Asp Gly Ser His
 1               5

<210> SEQ ID NO 60
<211> LENGTH: 7
<212> TYPE: PRT
<213> ORGANISM: Thraustochytrium aureum

<400> SEQUENCE: 60

Gln His Val Leu Gly His His
 1               5

<210> SEQ ID NO 61
<211> LENGTH: 4
<212> TYPE: PRT
<213> ORGANISM: Thraustochytrium aureum

<400> SEQUENCE: 61

His Pro Trp His
 1

<210> SEQ ID NO 62
<211> LENGTH: 5
<212> TYPE: PRT
<213> ORGANISM: Thraustochytrium aureum

<400> SEQUENCE: 62

His Lys Phe Gln His
 1               5
```

```
<210> SEQ ID NO 63
<211> LENGTH: 6
<212> TYPE: PRT
<213> ORGANISM: Thraustochytrium aureum

<400> SEQUENCE: 63

His Gln Ile Glu His His
 1               5

<210> SEQ ID NO 64
<211> LENGTH: 7
<212> TYPE: PRT
<213> ORGANISM: Dictyostelium discoideum

<400> SEQUENCE: 64

Gln His Val Ile Gly His His
 1               5

<210> SEQ ID NO 65
<211> LENGTH: 6
<212> TYPE: PRT
<213> ORGANISM: Dictyostelium discoideum

<400> SEQUENCE: 65

His Gln Val Val His His
 1               5

<210> SEQ ID NO 66
<211> LENGTH: 7
<212> TYPE: PRT
<213> ORGANISM: Mortierella alpina

<400> SEQUENCE: 66

Gln His Met Leu Gly His His
 1               5

<210> SEQ ID NO 67
<211> LENGTH: 6
<212> TYPE: PRT
<213> ORGANISM: Unknown
<220> FEATURE:
<223> OTHER INFORMATION: Synechocytis (species unknown)

<400> SEQUENCE: 67

His Gln Val Thr His His
 1               5

<210> SEQ ID NO 68
<211> LENGTH: 335
<212> TYPE: PRT
<213> ORGANISM: Schizochytrium aggregatum
<220> FEATURE:
<221> NAME/KEY: VARIANT
<222> LOCATION: (335)...(335)
<223> OTHER INFORMATION: Xaa = Unknown or other at position 335

<400> SEQUENCE: 68

Ser His Gly Ala Phe Ser Lys Ser Arg Phe Met Asn Lys Ala Ala Gly
 1               5                  10                  15

Trp Thr Leu Asp Met Ile Gly Ala Ser Ala Met Thr Trp Glu Met Gln
                20                  25                  30

His Val Leu Gly His His Pro Tyr Thr Asn Leu Ile Glu Met Glu Asn
            35                  40                  45
```

-continued

```
Gly Leu Ala Lys Val Lys Gly Ala Asp Val Asp Pro Lys Val Asp
 50                  55                  60
Gln Glu Ser Asp Pro Asp Val Phe Ser Thr Tyr Pro Met Leu Arg Leu
 65                  70                  75                  80
His Pro Trp His Arg Gln Arg Phe Tyr His Lys Phe Gln His Leu Tyr
                 85                  90                  95
Ala Pro Leu Ile Phe Gly Phe Met Thr Ile Asn Lys Val Ile Ser Gln
                100                 105                 110
Asp Val Gly Val Leu Arg Lys Arg Leu Phe Gln Ile Asp Ala Asn
                115                 120                 125
Cys Arg Tyr Gly Ser Pro Trp Asn Val Ala Arg Phe Trp Ile Met Lys
130                 135                 140
Leu Leu Thr Thr Leu Tyr Met Val Ala Leu Pro Met Tyr Met Gln Gly
145                 150                 155                 160
Pro Ala Gln Gly Leu Lys Leu Phe Phe Met Ala His Phe Thr Cys Gly
                165                 170                 175
Glu Val Leu Ala Thr Met Phe Ile Val Asn His Ile Ile Glu Gly Val
                180                 185                 190
Ser Tyr Ala Ser Lys Asp Ala Val Lys Gly Val Met Ala Pro Pro Arg
                195                 200                 205
Thr Val His Gly Val Thr Pro Met Gln Val Thr Gln Lys Ala Leu Ser
210                 215                 220
Ala Ala Glu Ser Thr Lys Ser Asp Ala Asp Lys Thr Thr Met Ile Pro
225                 230                 235                 240
Leu Asn Asp Trp Ala Ala Val Gln Cys Gln Thr Ser Val Asn Trp Ala
                245                 250                 255
Val Gly Ser Trp Phe Trp Asn His Phe Ser Gly Gly Leu Asn His Gln
                260                 265                 270
Ile Glu His His Cys Phe Pro Gln Asn Pro His Thr Val Asn Val Tyr
                275                 280                 285
Ile Ser Gly Ile Val Lys Glu Thr Cys Glu Glu Tyr Gly Val Pro Tyr
290                 295                 300
Gln Ala Glu Ile Ser Leu Phe Ser Ala Tyr Phe Lys Met Leu Ser His
305                 310                 315                 320
Leu Arg Thr Leu Gly Asn Glu Asp Leu Thr Ala Trp Ser Thr Xaa
                325                 330                 335

<210> SEQ ID NO 69
<211> LENGTH: 430
<212> TYPE: PRT
<213> ORGANISM: Isochrysis galbana

<400> SEQUENCE: 69

Met Cys Asn Ala Ala Gln Val Glu Thr Gln Ala Leu Arg Ala Lys Glu
  1               5                  10                  15
Ala Ala Lys Pro Thr Trp Thr Lys Ile His Gly Arg Thr Val Asp Val
                 20                  25                  30
Glu Thr Phe Arg His Pro Gly Gly Asn Ile Leu Asp Leu Phe Leu Gly
                 35                  40                  45
Met Asp Ala Thr Thr Ala Phe Glu Thr Phe His Gly His Lys Gly
 50                  55                  60
Ala Trp Lys Met Leu Lys Thr Leu Pro Glu Lys Val Ala Ala
 65                  70                  75                  80
Asp Ile Pro Ala Gln Lys Glu Glu His Val Ala Glu Met Thr Arg Leu
                 85                  90                  95
```

-continued

```
Met Ala Ser Trp Arg Glu Arg Gly Leu Phe Lys Pro Arg Pro Val Ala
                100                 105                 110
Ser Ser Ile Tyr Gly Leu Cys Val Ile Phe Ala Ile Ala Ala Ser Val
            115                 120                 125
Ala Cys Ala Pro Tyr Ala Pro Val Leu Ala Gly Ile Ala Val Gly Thr
        130                 135                 140
Cys Trp Ala Gln Cys Gly Phe Leu Gln His Met Gly His Arg Glu
145                 150                 155                 160
Trp Gly Arg Thr Trp Ser Phe Ala Phe Gln His Leu Phe Glu Gly Leu
                165                 170                 175
Leu Lys Gly Gly Ser Ala Ser Trp Trp Arg Asn Arg His Asn Lys His
            180                 185                 190
His Ala Lys Thr Asn Val Leu Gly Glu Asp Gly Asp Leu Arg Thr Thr
        195                 200                 205
Pro Phe Phe Ala Trp Asp Pro Thr Leu Ala Lys Lys Val Pro Asp Trp
    210                 215                 220
Ser Leu Arg Thr Gln Ala Phe Thr Phe Leu Pro Ala Leu Gly Ala Tyr
225                 230                 235                 240
Val Phe Val Phe Ala Phe Thr Val Arg Lys Tyr Ser Val Val Lys Arg
                245                 250                 255
Leu Trp His Glu Val Ala Leu Met Val Ala His Tyr Ala Leu Phe Ser
            260                 265                 270
Trp Ala Leu Ser Ala Ala Gly Ala Ser Leu Ser Ser Gly Leu Thr Phe
        275                 280                 285
Tyr Cys Thr Gly Tyr Ala Trp Gln Gly Ile Tyr Leu Gly Phe Phe Phe
    290                 295                 300
Gly Leu Ser His Phe Ala Val Glu Arg Val Pro Ser Thr Ala Thr Trp
305                 310                 315                 320
Leu Glu Ser Thr Met Met Gly Thr Val Asp Trp Gly Gly Ser Ser Ala
                325                 330                 335
Phe Cys Gly Tyr Leu Ser Gly Phe Leu Asn Ile Gln Ile Glu His His
            340                 345                 350
Met Ala Pro Gln Met Pro Met Glu Asn Leu Arg Gln Ile Arg Ala Asp
        355                 360                 365
Cys Lys Ala Ala His Lys Phe Gly Leu Pro Tyr Arg Glu Leu Thr
    370                 375                 380
Phe Val Ala Ala Thr Lys Leu Met Met Ser Gly Leu Tyr Arg Thr Gly
385                 390                 395                 400
Lys Asp Glu Leu Lys Leu Arg Ala Asp Arg Arg Lys Phe Thr Arg Ala
                405                 410                 415
Gln Ala Tyr Met Gly Ala Ala Ser Ala Leu Val Asp Thr Leu
            420                 425                 430
```

<210> SEQ ID NO 70
<211> LENGTH: 515
<212> TYPE: PRT
<213> ORGANISM: Thraustochytrium aureum

<400> SEQUENCE: 70

```
Met Thr Val Gly Phe Asp Glu Thr Val Thr Met Asp Thr Val Arg Asn
1               5                   10                  15
His Asn Met Pro Asp Asp Ala Trp Cys Ala Ile His Gly Thr Val Tyr
                20                  25                  30
Asp Ile Thr Lys Phe Ser Lys Val His Pro Gly Gly Asp Ile Ile Met
```

-continued

```
                35                  40                  45
Leu Ala Ala Gly Lys Glu Ala Thr Ile Leu Phe Glu Thr Tyr His Ile
 50                  55                  60
Lys Gly Val Pro Asp Ala Val Leu Arg Lys Tyr Lys Val Gly Lys Leu
 65                  70                  75                  80
Pro Gln Gly Lys Lys Gly Glu Thr Ser His Met Pro Thr Gly Leu Asp
                 85                  90                  95
Ser Ala Ser Tyr Tyr Ser Trp Asp Ser Glu Phe Tyr Arg Val Leu Arg
                100                 105                 110
Glu Arg Val Ala Lys Lys Leu Ala Glu Pro Gly Leu Met Gln Arg Ala
                115                 120                 125
Arg Met Glu Leu Trp Ala Lys Ala Ile Phe Leu Leu Ala Gly Phe Trp
130                 135                 140
Gly Ser Leu Tyr Ala Met Cys Val Leu Asp Pro His Gly Gly Ala Met
145                 150                 155                 160
Val Ala Ala Val Thr Leu Gly Val Phe Ala Ala Phe Val Gly Thr Cys
                165                 170                 175
Ile Gln His Asp Gly Ser His Gly Ala Phe Ser Lys Ser Arg Phe Met
                180                 185                 190
Asn Lys Ala Ala Gly Trp Thr Leu Asp Met Ile Gly Ala Ser Ala Met
                195                 200                 205
Thr Trp Glu Met Gln His Val Leu Gly His His Pro Tyr Thr Asn Leu
210                 215                 220
Ile Glu Met Glu Asn Gly Leu Ala Lys Val Lys Gly Ala Asp Val Asp
225                 230                 235                 240
Pro Lys Lys Val Asp Gln Glu Ser Asp Pro Asp Val Phe Ser Thr Tyr
                245                 250                 255
Pro Met Leu Arg Leu His Pro Trp His Arg Gln Arg Phe Tyr His Lys
                260                 265                 270
Phe Gln His Leu Tyr Ala Pro Leu Ile Phe Gly Phe Met Thr Ile Asn
                275                 280                 285
Lys Val Ile Ser Gln Asp Val Gly Val Val Leu Arg Lys Arg Leu Phe
290                 295                 300
Gln Ile Asp Ala Asn Cys Arg Tyr Gly Ser Pro Trp Asn Val Ala Arg
305                 310                 315                 320
Phe Trp Ile Met Lys Leu Leu Thr Thr Leu Tyr Met Val Ala Leu Pro
                325                 330                 335
Met Tyr Met Gln Gly Pro Ala Gln Gly Leu Lys Leu Phe Phe Met Ala
                340                 345                 350
His Phe Thr Cys Gly Glu Val Leu Ala Thr Met Phe Ile Val Asn His
                355                 360                 365
Ile Ile Glu Gly Val Ser Tyr Ala Ser Lys Asp Ala Val Lys Gly Val
370                 375                 380
Met Ala Pro Pro Arg Thr Val His Gly Val Thr Pro Met Gln Val Thr
385                 390                 395                 400
Gln Lys Ala Leu Ser Ala Ala Glu Ser Thr Lys Ser Asp Ala Asp Lys
                405                 410                 415
Thr Thr Met Ile Pro Leu Asn Asp Trp Ala Ala Val Gln Cys Gln Thr
                420                 425                 430
Ser Val Asn Trp Ala Val Gly Ser Trp Phe Trp Asn His Phe Ser Gly
                435                 440                 445
Gly Leu Asn His Gln Ile Glu His His Cys Phe Pro Gln Asn Pro His
 450                 455                 460
```

-continued

```
Thr Val Asn Val Tyr Ile Ser Gly Ile Val Lys Glu Thr Cys Glu Glu
465                 470                 475                 480

Tyr Gly Val Pro Tyr Gln Ala Glu Ile Ser Leu Phe Ser Ala Tyr Phe
                485                 490                 495

Lys Met Leu Ser His Leu Arg Thr Leu Gly Asn Glu Asp Leu Thr Ala
                500                 505                 510

Trp Ser Thr
        515

<210> SEQ ID NO 71
<211> LENGTH: 5
<212> TYPE: PRT
<213> ORGANISM: Artificial Sequence
<220> FEATURE:
<223> OTHER INFORMATION: Histidine-Rich Motif

<400> SEQUENCE: 71

His Met Gly Gly His
1               5

<210> SEQ ID NO 72
<211> LENGTH: 5
<212> TYPE: PRT
<213> ORGANISM: Artificial Sequence
<220> FEATURE:
<223> OTHER INFORMATION: Histidine-Rich Motif

<400> SEQUENCE: 72

His Asn Lys His His
1               5

<210> SEQ ID NO 73
<211> LENGTH: 5
<212> TYPE: PRT
<213> ORGANISM: Artificial Sequence
<220> FEATURE:
<223> OTHER INFORMATION: Histidine-Rich Motif

<400> SEQUENCE: 73

Gln Ile Glu His His
1               5
```